US009090898B2

(12) United States Patent
Farmer et al.

(10) Patent No.: US 9,090,898 B2
(45) Date of Patent: Jul. 28, 2015

(54) GREEN PROCESS AND COMPOSITIONS FOR PRODUCING POLY(5HV) AND 5 CARBON CHEMICALS

(75) Inventors: William R. Farmer, Concord, MA (US); Jeff Bickmeier, Arlington, MA (US); Chenfeng Lu, Watertown, MA (US); Dong-Eun Chang, Newton, MA (US); Frank Skraly, Watertown, MA (US); Thomas Martin Ramseier, Newton, MA (US)

(73) Assignee: Metabolix, Inc., Cambridge, MA (US)

( * ) Notice: Subject to any disclaimer, the term of this patent is extended or adjusted under 35 U.S.C. 154(b) by 671 days.

(21) Appl. No.: 12/637,706

(22) Filed: Dec. 14, 2009

(65) Prior Publication Data

US 2010/0168481 A1     Jul. 1, 2010

Related U.S. Application Data

(60) Provisional application No. 61/122,250, filed on Dec. 12, 2008.

(51) Int. Cl.
| *C12N 1/20* | (2006.01) |
| *C12N 1/32* | (2006.01) |
| *C12P 7/18* | (2006.01) |
| *C12P 13/08* | (2006.01) |
| *C12P 7/62* | (2006.01) |
| *C12P 7/46* | (2006.01) |
| *C07H 21/04* | (2006.01) |
| *C07C 31/18* | (2006.01) |
| *C12N 15/52* | (2006.01) |
| *C12N 9/04* | (2006.01) |
| *C12N 9/02* | (2006.01) |
| *C12N 9/10* | (2006.01) |
| *C12N 9/80* | (2006.01) |
| *C12N 9/88* | (2006.01) |
| *C12N 9/00* | (2006.01) |
| *C12P 7/04* | (2006.01) |
| *C12P 7/42* | (2006.01) |
| *C12P 7/44* | (2006.01) |

(52) U.S. Cl.
CPC .............. *C12N 15/52* (2013.01); *C12N 9/0006* (2013.01); *C12N 9/0008* (2013.01); *C12N 9/0069* (2013.01); *C12N 9/10* (2013.01); *C12N 9/1029* (2013.01); *C12N 9/1096* (2013.01); *C12N 9/80* (2013.01); *C12N 9/88* (2013.01); *C12N 9/93* (2013.01); *C12P 7/04* (2013.01); *C12P 7/18* (2013.01); *C12P 7/42* (2013.01); *C12P 7/44* (2013.01); *C12P 7/625* (2013.01)

(58) Field of Classification Search
CPC ............ C12P 7/18; C12P 7/42; C12P 13/005; C12P 7/40; C12P 7/625; C12N 15/52; C12N 15/70; C12N 9/0008; C12N 15/63; C12N 9/0004; C12N 9/001; C12N 9/0036; C12N 9/10; F28B 1/06; F28F 19/06; F28F 1/126; F28F 21/089; F28F 2245/00
See application file for complete search history.

(56) References Cited

U.S. PATENT DOCUMENTS

| 5,000,000 | A | 3/1991 | Ingram |
| 5,102,797 | A | 4/1992 | Tucker |
| 5,470,727 | A | 11/1995 | Mascarenhas |
| 5,480,794 | A | 1/1996 | Peoples |
| 5,595,889 | A | 1/1997 | Richaud |
| 6,040,160 | A | 3/2000 | Kojima |
| 6,117,658 | A | 9/2000 | Dennis |
| 6,316,262 | B1 | 11/2001 | Huisman |
| 6,323,010 | B1 | 11/2001 | Skraly |
| 6,689,589 | B2 | 2/2004 | Huisman |
| 6,759,219 | B2 | 7/2004 | Hein |
| 6,979,560 | B1 | 12/2005 | Livshits |
| 7,081,357 | B2 | 7/2006 | Huisman |
| 7,229,804 | B2 | 6/2007 | Huisman |

(Continued)

FOREIGN PATENT DOCUMENTS

| JP | 848842 | 2/1996 |
| WO | 9914313 | 3/1999 |

(Continued)

OTHER PUBLICATIONS

Vrljic et al. A new type of transporter with a new type of cellular function: L-lysine export from *Corynebacterium glutamicum*, Molecular Microbiology (1996), 22(5): 815-826.*

(Continued)

*Primary Examiner* — Iqbal H Chowdhury
(74) *Attorney, Agent, or Firm* — Pabst Patent Group LLP

(57) ABSTRACT

Recombinant hosts for producing polyhydroxyalkanoates and methods of producing polyhydroxyalkanoates from renewable carbon substrates are provided. Certain recombinant hosts that produce 5 carbon chemicals such as 5-aminopentanoate (5AP), 5-hydroxyvalerate (5HV), glutarate, and 1,5 pentanediol (PDO) are also provided. One embodiment provides a recombinant host expressing a gene encoding a heterologous enzyme selected from the group consisting of a polyhydroxyalkanoate synthase and a 5-hydroxyvalerate-CoA (5HV-CoA) transferase, wherein the host produces a polymer containing 5-hydroxyvalerate. Preferably, the host expresses both a polyhydroxyalkanoate synthase and a 5HV-CoA transferase. The host can be prokaryotic or eukaryotic. A preferred prokaryotic host is *E. coli*. The polymers produced by the recombinant hosts can be homopolymers or copolymers of 5-hydroxyvalerate. A preferred copolymer is poly(3-hydroxybutyrate-co-5-hydroxyvalerate).

36 Claims, 9 Drawing Sheets

(56) References Cited

U.S. PATENT DOCUMENTS

| | | | |
|---|---|---|---|
| 2002/0055154 A1* | 5/2002 | Mockel et al. | 435/115 |
| 2004/0033572 A1 | 2/2004 | Skraly | |
| 2004/0253693 A1 | 12/2004 | Hein | |
| 2006/0117401 A1 | 6/2006 | Schmitz | |

FOREIGN PATENT DOCUMENTS

| | | |
|---|---|---|
| WO | 0240690 | 5/2002 |
| WO | 2004024876 | 3/2004 |

OTHER PUBLICATIONS

Alexeyev, et al., "New mini-Tn5 derivatives for insertion mutagenesis and genetic engineering in gram-negative bacteria", Can. J. Microbiol. 41:1053-1055 (1995).

Andi, et al., "Kinetic mechanism of histidine-tagged homocitrate synthase from *Saccharomyces cerevisiae*", Biochem., 43:11790-11795 (2004).

Behshad, at al., "Enantiomeric free radicals and enzymatic control of stereochemistry in a radical mechanism: the case of lysine 2,3-aminomutases", Biochemistry, 45(42):12639-46 (2006).

Breitkreuz, et al. "Novel gamma-hydroxybutyrate dehydrogenase: identification and expression of an *Arabidopsis* DNA and potential role under oxygen deficiency", J. Biol. Chem. 278:41552-41556 (2003).

Cevallos, et al., "Genetic and physiological characterization of a *Rhizobium etli* mutant strain unable to synthesize poly-beta-hydroxybutyrate", J. Bacterial., 178 (6):1646-54 (1996).

Chang and Cohen, "Construction and characterization of amplifiable multicopy DNA cloning vehicles derived from the P15A cryptic miniplasmid", J. Bacterial., 134:1141-1156 (1978).

Datsenko and Wanner, "One-step inactivation of chromosomal genes in *Escherichia coli* K-12 using PCR products", Proc. Natl. Acad. Sci. U S A., 97:6640-6645 (2000).

De Lorenzo and Timmis, "Analysis and construction of stable phenotypes in gram-negative bacteria with Tn5- and Tn10-derived minitransposons", Methods Enzymol., 235:386-405 (1994).

De Lorenzo, et al.,"Mini-Tn5 transposon derivatives for insertion mutagenesis, promoter probing, and chromosomal insertion of cloned DNA in gram-negative eubacteria", J. Bacterial, 172:6568 (1990).

Eikmanns and Buckel, "Properties of 5-hydroxyvalerate CoA-transferase from *Clostridium aminovalericum*", Biol. Chem. Hoppe-Seyler, 371:1077-1082 (1990).

Espinosa-Urgel and Ramos, "Expression of a *Pseudomonas putida* aminotransferase involved in lysine catabolism is induced in the rhizosphere", Appl. Environ. Microbial., 67 (11):5219-5224 (2001).

Flashner and Massey, "Purification and properties of L-lysine monooxygenase from *Pseudomonas fluorescens*", J. Biol. Chem., 249:2 579-2586 (1974).

Fouts, et al., "Complete genome sequence of the N2-fixing broad host range endophyte *Klebsiella pneumoniae* 342 and virulence predictions verified in mice", PLoS Genet., 4 (7):E1000141 (2008).

Franke, et al., "YfiK from *Escherichia coli* promotes export of O-acetylserine and cysteine", J. Bacterial., 185:1161-1166 (2003).

Fuhrer, et al., "Computational prediction and experimental verification of the gene encoding the NAD+/NADP+-dependent succinate semialdehyde dehydrogenase in *Escherichia coli*", J Bacteriol., 189(22):8073-8 (2007).

Fukui and Doi, "Cloning and analysis of the poly(3-hydroxybutyrate-co-3-hydroxyhexanoate) biosynthesis genes of *Aeromonas caviae*", J. Bacteriol., 179:4821-30 (1997).

Fukui, et al., "Purification and characterization of NADP-linked acetoacetyl-CoA reductase from *Zoogloea ramigera* I-16-M", Biochim. Biophys. Acta, 917:365-371 (1987).

Gerhardt, et al., "Fermentation of 4-aminobutyrate by *Clostridium aminobutyricum*: cloning of two genes involved in the formation and dehydration of 4-hydroxybutyryl-CoA", Arch Microbiol, 174:189-199 (2000).

Gerngross, et al., "Overexpression and purification of the soluble polyhydroxyalkanoate synthase from *Alcaligenes eutrophus*: evidence for a required posttranslational modification for catalytic activity", Biochemistry, 33:9311-9320 (1994).

Gowrishankar, "Evidence for an arginine exporter encoded by yggA (argO) that is regulated by the LysR-type transcriptional regulator ArgP in *Escherichia coli*", J. Bacteriol. 186:3539-3546 (2004).

Hamilton, et al. "New method for generating deletions and gene replacements in *Escherichia coli*", J. Bacteriol., 171(9):4617-4622 (1989).

Hayaishi, "Crystalline oxygenases of *Pseudomonads*", Bacteriol. Rev., 30:720-731 (1966).

Herrero, et al., "Transposon vectors containing non-antibiotic resistance selection markers for cloning and stable chromosomal insertion of foreign genes in gram-negative bacteria", J. Bacteriol., 172:6557-6567 (1990).

Hinshelwood, et al., "Characterisation of a novel mouse liver aldo-keto reductase AKR7A5", FEBS Letters, 523:213-218 (2002).

Ho, et al., Site-directed mutagenesis by overlap extension using the polymerase chain reaction, Gene, 77(1):51-9 (1989).

Huisman, et al "Metabolism of poly(3-hydroxyalkanoates) (PHAs) by *Pseudomonas oleovorans*. Identification and sequences of genes and function of the encoded proteins in the synthesis and degradation of PHA", J. Biol. Chem., 266(4):2191-2198 (1991.

Hsiao, et al., "High-frequency transformation of yeast by plasmids containing the cloned yeast ARG4 gene", Proc. Natl. Aced. Sci. (USA), 76:3829 (1979).

Hustede and Steinbüchel, "Characterization of the polyhydroxyalkanoate synthase gene locus of *Rhodobacter sphaeroides*", Biotechnol. Lett. , 15:709-14 (1993.

Hustede et. al "Cloning of poly(3-hydroxybutieric acid) s ynthase genes of *Rhodobacter sphaenaides* and *Rhodospirillum rubrum* and heterologous expression in *Alcaligenes eutrophus*", FEMS Microbiol. Lett, 93: 285-90 (1992).

Ischihara, et al., "Metabolism of L-lysine by bacterial enzymes. V. glutaric semialdehyde dehydrogenase", J. Biochem., 49:154-167 (1961).

Jensen, "The *Escherichia coli* K-12 "wild types" W3110 and MG1655 have an rph frameshift mutation that leads to pyrimidine starvation due to low pyrE expression levels", J. Bacteriol. 175(11):3401-3407 (1993).

Jia, et al., "Kinetics and product analysis of the reaction catalysed by recombinant homoaconitase from *Thermus thermophilus*", Biochem. J., 396:479-485 (2006).

Jo, et. al., Production system for biodegradable polyester polyhydroxybutyrate by *Corynebacterium glutamicum*\,J. Biosci. And Bioeng., 102: 233-236 (2006.

Kaneko, et al, "Sequence analysis of the genome of the unicellular *Cyanobacterium Synechocysti s* sp. strain PCC6803. II. Sequence determination of the entire genome and assignment of potential protein-coding regions", DNA Res 3(3):109-36 (1996).

Kutukova, et al., "The yeaS (leuE) gene of *Escherichia coli* encodes an exporter of leucine, and the Lrp protein regulates its expression", FEBS Lett. 579 (21):4629-34 (2005).

Kutukova, et al., "Expression of the genes encoding RhtB family proteins depends on global regulator Lrp", Mol. Biol. (Mosk.) 39(3):374-378 (2005). Article is in Russia, English abstract.

Leal, et al., "PduP is a coenzyme-a-acylating proplonaldehyde dehydrogenase associated with the polyhedral bodies involved in B12-dependent 1,2-propanediol degradation by *Salmonella* enterica serovar Typhimurlum LT2", Arch. Microbial., 180:353-361 (2003).

Liebergesell and Steinbuchel, "Cloning and molecular analysis of the poly(3-hydroxybutyric acid) biosynthetic genes of *Thiocystis violacea*", Appl Microbiol Biotechnol., 38(4):493-501 (1993).

Liebergesell and Steinbuchel, "Cloning and nucleotide sequences of genes relevant for biosynthesis of poly(3-hydroxybutyric acid) in *Chromatium vinosum* strain D", Eur. J. Biochem. , 209:135-150 (1992).

Madison and Huisman, "Metabolic engineering of poly(3-hydroxyalkanoates): from DNA to plastic," Microbiology and Molecular Biology Reviews, 63:21-53 (1999).

McClelland, et al., "Complete genome sequence of *Salmonella enterica* serovar Typhimurium LT2", Nature, 413:852-856 (2001).

(56) References Cited

OTHER PUBLICATIONS

McCool & Cannon, PhaC and PhaR are required for polyhydroxyalkanoic acid synthase activity in *Bacillus megaterium*\, J. Bacteriol.,183(14):4235-4243 (2001).

Meng and Bennett, "Nucleotide sequence of the *Escherichia coli* cad operon: a system for neutralization of low extracellular pH", J. Bacteria, 174 (8):2659-2669 (1992).

Metcalf, et al., "Conditionally Replicative and Conjugative Plasmids CarryinglacZ± for Cloning, Mutagenesis, and Allele Replacement in Bacteria", Plasmid, 35:1-13 (1996).

Miller and Mekalanos, A novel suicide vector and its use in construction of insertion mutations: osmoregulation of outer membrane proteins and virulence determinants in *Vibrio cholerae* requires toxR\, J. Bacteriol. 170(6):2675-2583 (1988).

Miyazaki, et al, "Characterization of homoisocltrate dehydrogenase involved in lysine biosynthesis of an extremely *Thermophilic bacterium*, Thermus Ihermophilus HB27, and evolutionary implication of beta-decarboxylating dehydrogenase", J. Biol. Chem., 278:1864-1871 (2003).

Nandineni and Gowrishankar, Evidence for an arginine exporter encoded by yggA (argO) that is regulated by the LysR-type transcriptional regulator ArgP in *Escherichia coli*\, J. Bacteriol., 186:3539-3546 (2004).

Nishimura, et al, "Purification and properties of beta-ketothiolase from *Zoogloea ramigera*", Arch. Microbiol., 116:21-27 (1978).

Panke, et al., "Engineering of quasi-natural *Pseudomonas putida* strains for toluene metabolism through an ortho-cleavage degradation pathway", Appl. Enviro. Microbiol. 64:748-751 (1998).

Peoples and Sinskey, "Poly-beta-hydroxybutyrate (PHB) biosynthesis in *Alcaligenes eutrophus* H16. Identification and characterization of the PHB polymerase gene (phbC)", J Biol Chem. 264(26):15293-7 (1989).

Peoples and Sinskey, "Poly-beta-hydroxybutyrate biosynthesis in *Alcaligenes eutrophus* H16. Characterization of the genes encoding beta-ketothiolase and acetoacetyl-CoA reductase", J. Biol. Chem., 264:15298-15303 (1989).

Peoples, et al. "Biosynthetic Thiolase from *Zoogloea ramigera*", J. Biol. Chem., 262(1):97-102 (1987).

Peredelchuk and Bennett, "A method for construction of *E. coli* strains with multiple DNA insertions in the chromosome", Gene, 187(2):231-238 (1997).

Pieper and Steinbuchel, "Identification, cloning an d sequence analysis of the poly(3-hydroxyalkanoic acid) synthase gene of the gram-positive bacterium Rhodococcus rubber", FEMS Microbiol. Lett., 96(1):73-80 (1992).

Pohlmann, et al., "Genome sequence of the bioplastic-producing "Knaligas" bacterium *Ralstonia eutropha* H16", Nature Biotech, 24(10)1257-1262 (2006).

Reiser, et al., "Characterization and cloning of an (R)-specific trans-2,3-enoylacyl-CoA hydratase from *Rhodospirillum rubrum* and use of this enzyme for PHA production in *Escherichia coli*", Appl. Microbial. Blotechnol 53(4209-218 (2000).

Reitz and Rodweli, Delta-aminovaleramidase of *Pseudomonas putida*\, J. Biol. Chem., 245:3091-3096 (1970).

Reitz, et al., "Synthesis of delta-aminovaleramide", Anal. Biochem., 28:269-272 (1969).

Revelles, et al, "The davDT operon of *Pseudomonas putida*, involved in lysine catabolism, is induced in response to the pathway intermediate delta-aminovaleric acid", J. Bacteriol., 186:3439-3446 (2004).

Revelles, et al., "Multiple and interconnected pathways for L-lysine catabolism in *Pseudomonas putida* KT2440", J. Bacteriol., 187:7500-7510 (2005).

Riley, et al., "*Escherichia coli* K-12: a cooperatively developed annotation snapshot" 2005, Nucleic Acids Res., 34 (1):1-9 (2006).

Schembri, et al., "Phosphate concentration regulates transcription of the Acinetobacter polyhydroxyalkanoic acid biosynthetic genes", J. Bacteriol. 177 (15):4501-7 (1995).

Slater, et al., "Multiple beta-ketothiolases mediate poly(beta-hydroxyalkanoate) copolymer synthesis in *Ralstonia eutropha*", J. Bacteriol., 180(8):1979-87 (1998).

Söhling & Gottschalk, "Molecular analysis of the anaerobic succinate degradation pathway in *Clostridium kluyveri*," J. Bacteriol. 178:871-880 (1996).

Spratt, et al., "Isolation and genetic characterization of *Escherichia coli* mutants defective in propionate metabolism", J. Bacteriol., 146(3):1166-1169 (1981).

Steffes, et al., "The lysP gene encodes the lysine-specific permease", J Bacteriol., 174(10):3242-9 (1992).

Steinbüchel, et al, "Molecular basis for biosynthesis and accumulation of polyhydroxyalkanoic acids in bacteria," FEMS Microbiol Rev., 9(2-4):217-30 (1992).

Takeda, "Crystalline L-lysine oxygenase", J. Biol. Chem., 241:2733-2736 (1966).

Thompson, et al., "The CLUSTAL_X windows interface: flexible strategies for multiple sequence alignment aided by quality analysis tools", Nucleic Acids Res., 25:4876-4882 (1997).

Timm and Steinbuchel, "Cloning and molecular analysis of the poly(3- hydroxyalkanoic acid) gene locus of *Pseudomonas aeruginosa* PAO1", Eur. J. Biochem., 209:15-30 (1992).

Tombolini, et al.' "Poly-beta-hydroxybutyrate (PHB) biosynthetic genes in *Rhizobium meliloti* 41", Microbiology., 141 ( Pt 10):2553-9 (1995).

Tong, et al., "1,3-Propanediol production by *Escherichia coli* expressing genes from the *Klebsiella pneumoniae* dha regulon", Appl. Environ. Microbiol., 57 (12):3541-3546 (1991).

Ueda, et al., "Molecular analysis of the poly(3-hydroxyalkanoate) synthase gene from a methylotrophic bacterium, *Paracoccus denitrificans*", J Bacteriol., 178 (3):774-9 (1996).

Valentin, et al., "Cloning and characterization of the *Methylobacterium extorquens* polyhydroxyalkanoic-acid-synthase structural gene", Appl Microbial Biotechnol., 39(3):309-17 (1993).

Van Beilen, et al., "DNA sequence determination and functional characterization of the OCT-plasmid-encoded alkJKL genes of *Pseudomonas oleovorans*," Mol. Microbiol. 6: 3121-36 (1992).

Van Solingen, et al., "Fusion of yeast spheroplasts", J. Bacteriol., 130:946-7 (1977).

Vrljic, et al., "A new type of transporter with a new type of cellular function: L-lysine export from *Corynebacterium glutamicum*", Mol. Microbiol. 22(5):815-826 (1996).

Wendisch, et al., "Metabolic engineering of *Escherichia coli* and *Corynebacterium glutamicum* for biotechnological production of organic acids and amino acids", Curr. Opin. Miorobiol 9:268-274 (2007).

Xu, et al., "The alpha-aminoadipate pathway for lysine biosynthesis in fungi", Cell Biochem. Biophys., 46:43-64 (2006).

Yasutani, et al., "Analysis of beta-ketothiolase and acetoacetyl-CoA reductase genes of a methylotrophic bacterium, *Paracoccus denitrificans*, and their expression in *Escherichia coli*", FEMS Microbiol. Lett. 133(1-2):85-90 (1995).

Yamanishi, et al., "Prediction of missing enzyme genes in a bacterial metabolic network—Reconstruction of the lysine-degradation pathway of *Pseudomonas aeruginosa*", Febs. Journal, 274(9):2262-2273 (2007).

Zakataeva, et al., "The novel transmembrane *Escherichia coli* proteins involved in the amino acid efflux", FEBS Lett. 452(3):228-32 (1999).

* cited by examiner

SEQUENCE LISTING

<160> NUMBER OF SEQ ID NOS: 65

<210> SEQ ID NO 1
<211> LENGTH: 45
<212> TYPE: DNA
<213> ORGANISM: Artificial Sequence
<220> FEATURE:
<223> OTHER INFORMATION: Synthetic FS-E5' primer

<400> SEQUENCE: 1
ggaattcagg aggttttttat gaacgatacg gccaacaaga ccagc          45

<210> SEQ ID NO 2
<211> LENGTH: 44
<212> TYPE: DNA
<213> ORGANISM: Artificial Sequence
<220> FEATURE:
<223> OTHER INFORMATION: Synthetic FS-E3' Primer

<400> SEQUENCE: 2
ggggtacctc actggccggt ggtgggcttg gtggtcttgc ggcg             44

<210> SEQ ID NO 3
<211> LENGTH: 45
<212> TYPE: DNA
<213> ORGANISM: Artificial Sequence
<220> FEATURE:
<223> OTHER INFORMATION: Synthetic FS-C5' Primer

<400> SEQUENCE: 3
ggggtaccag gaggttttta tgtccccatt cccgatcgac atccg            45

<210> SEQ ID NO 4
<211> LENGTH: 43
<212> TYPE: DNA
<213> ORGANISM: Artificial Sequence
<220> FEATURE:
<223> OTHER INFORMATION: Synthetic FS-C3' Primer

<400> SEQUENCE: 4
cgggatcctc agccgcgttc gttcagccag cggccgatcg ccg              43

<210> SEQ ID NO 5
<211> LENGTH: 47
<212> TYPE: DNA
<213> ORGANISM: Artificial Sequence
<220> FEATURE:
<223> OTHER INFORMATION: Synthetic K5-1 5' Primer

<400> SEQUENCE: 5
gctgaggatc caggaggttt ttatgttagg tcagatgatg cgtaatc          47

<210> SEQ ID NO 6
<211> LENGTH: 36
<212> TYPE: DNA
<213> ORGANISM: Artificial Sequence
<220> FEATURE:
<223> OTHER INFORMATION: Synthetic Primer K3-1

<400> SEQUENCE: 6
ctagaggatc cttattcaca gacagaagaa ctactg                      36

<210> SEQ ID NO 7
<211> LENGTH: 41
<212> TYPE: DNA
<213> ORGANISM: Artificial Sequence

```
<220> FEATURE:
<223> OTHER INFORMATION: Synthetic Primer K5-2

<400> SEQUENCE: 7
aattcaggag gttttatgt taggtcagat gatgcgtaat c                    41

<210> SEQ ID NO 8
<211> LENGTH: 30
<212> TYPE: DNA
<213> ORGANISM: Artificial Sequence
<220> FEATURE:
<223> OTHER INFORMATION: Synthetic Primer K3-2

<400> SEQUENCE: 8
gatccttatt cacagacaga agaactactg                               30

<210> SEQ ID NO 9
<211> LENGTH: 45
<212> TYPE: DNA
<213> ORGANISM: Artificial Sequence
<220> FEATURE:
<223> OTHER INFORMATION: Synthetic Primer Posynrbs.c

<400> SEQUENCE: 9
ggaattcagg aggttttat gttaggtcag atgatgcgta atcag               45

<210> SEQ ID NO 10
<211> LENGTH: 35
<212> TYPE: DNA
<213> ORGANISM: Artificial Sequence
<220> FEATURE:
<223> OTHER INFORMATION: Synthetic Primer Posynrbs.r

<400> SEQUENCE: 10
cgggatcctt attcacagac agaagaacta ctgcg                         35

<210> SEQ ID NO 11
<211> LENGTH: 43
<212> TYPE: DNA
<213> ORGANISM: Artificial Sequence
<220> FEATURE:
<223> OTHER INFORMATION: Synthetic  Primer A.eut.PhaG.c

<400> SEQUENCE: 11
ggaattcgga tcccaagtac cttgccgaca tctatgcgct ggc                43

<210> SEQ ID NO 12
<211> LENGTH: 35
<212> TYPE: DNA
<213> ORGANISM: Artificial Sequence
<220> FEATURE:
<223> OTHER INFORMATION: Synthetic Primer A.eut.EcoRI.r

<400> SEQUENCE: 12
ggaattcccg gctccgggat tgccctggcc ggact                         35

<210> SEQ ID NO 13
<211> LENGTH: 47
<212> TYPE: DNA
<213> ORGANISM: Artificial Sequence
<220> FEATURE:
<223> OTHER INFORMATION: Synthetic Primer MS069

<400> SEQUENCE: 13
ggtggatcct taagaggagg ttttatgac gcgtgaagtg gtagtgg             47
```

<210> SEQ ID NO 14
<211> LENGTH: 31
<212> TYPE: DNA
<213> ORGANISM: Artificial Sequence
<220> FEATURE:
<223> OTHER INFORMATION: Synthetic Primer MS070

<400> SEQUENCE: 14
ggtgctagct cagatacgct cgaagatggc g                           31

<210> SEQ ID NO 15
<211> LENGTH: 47
<212> TYPE: DNA
<213> ORGANISM: Artificial Sequence
<220> FEATURE:
<223> OTHER INFORMATION: Synthetic Primer MS071

<400> SEQUENCE: 15
ggtcctaggt taagaggagg tttttatgac aacattacaa ggtaaag          47

<210> SEQ ID NO 16
<211> LENGTH: 35
<212> TYPE: DNA
<213> ORGANISM: Artificial Sequence
<220> FEATURE:
<223> OTHER INFORMATION: Synthetic Primer MS072

<400> SEQUENCE: 16
ggtgcggccg cttacatgta taagccgccg ttaat                       35

<210> SEQ ID NO 17
<211> LENGTH: 31
<212> TYPE: DNA
<213> ORGANISM: Artificial Sequence
<220> FEATURE:
<223> OTHER INFORMATION: Synthetic Primer JB123b

<400> SEQUENCE: 17
ttatttcatg aaccctcgaa ttgacgcgct c                           31

<210> SEQ ID NO 18
<211> LENGTH: 31
<212> TYPE: DNA
<213> ORGANISM: Artificial Sequence
<220> FEATURE:
<223> OTHER INFORMATION: Synthetic Primer JB124a

<400> SEQUENCE: 18
ttatttcatg agcttatcga taccgtcgac c                           31

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer JB134

<400> SEQUENCE: 19
tgagcggata acaatttcac                                        20

<210> SEQ ID NO 20
<211> LENGTH: 31
<212> TYPE: DNA
<213> ORGANISM: Artificial Sequence
<220> FEATURE:
<223> OTHER INFORMATION: Synthetic Primer JB135

<400> SEQUENCE: 20
aataacacgt caacgcaaaa aggccatccg t                                           31

<210> SEQ ID NO 21
<211> LENGTH: 42
<212> TYPE: DNA
<213> ORGANISM: Artificial Sequence
<220> FEATURE:
<223> OTHER INFORMATION: Synthetic Primer JB136

<400> SEQUENCE: 21
tttttcatat gaggaggttt ttatgaacaa gaagaaccgc ca                               42

<210> SEQ ID NO 22
<211> LENGTH: 31
<212> TYPE: DNA
<213> ORGANISM: Artificial Sequence
<220> FEATURE:
<223> OTHER INFORMATION: Synthetic Primer JB137

<400> SEQUENCE: 22 tttttttgtac atcagccttt acgcaggtgc a                                          31

<210> SEQ ID NO 23
<211> LENGTH: 42
<212> TYPE: DNA
<213> ORGANISM: Artificial Sequence
<220> FEATURE:
<223> OTHER INFORMATION: Synthetic Primer JB138

<400> SEQUENCE: 23
tatatactag taggaggata atatgagcaa aaccaacgaa tc                               42

<210> SEQ ID NO 24
<211> LENGTH: 31
<212> TYPE: DNA
<213> ORGANISM: Artificial Sequence
<220> FEATURE:
<223> OTHER INFORMATION: Synthetic Primer JB139

<400> SEQUENCE: 24
tttttgtgca ctcaggcgat ttcagcgaag c                                           31

<210> SEQ ID NO 25
<211> LENGTH: 42
<212> TYPE: DNA
<213> ORGANISM: Artificial Sequence
<220> FEATURE:
<223> OTHER INFORMATION: Synthetic Primer JB145

<400> SEQUENCE: 25
tttttagatc taggaggttt ttatgctgcg tgctgcttct cg                               42

<210> SEQ ID NO 26
<211> LENGTH: 31
<212> TYPE: DNA
<213> ORGANISM: Artificial Sequence
<220> FEATURE:
<223> OTHER INFORMATION: Synthetic primer JB146

<400> SEQUENCE: 26
tttttagatc tttagcggaa atagtttgga c                                           31

<210> SEQ ID NO 27

```
<211> LENGTH: 109
<212> TYPE: DNA
<213> ORGANISM: Artificial Sequence
<220> FEATURE:
<223> OTHER INFORMATION: Synthetic Primer RF314

<400> SEQUENCE: 27
gcaagccaga gtaaccccgg acgcacgctg cgagcggcac gtagtgtgga tgccttacac      60
gccgcattta atcaataacc ttgagcgatt gtgtaggctg agctgctt                  109

<210> SEQ ID NO 28
<211> LENGTH: 110
<212> TYPE: DNA
<213> ORGANISM: Artificial Sequence
<220> FEATURE:
<223> OTHER INFORMATION: Synthetic Primer RF315

<400> SEQUENCE: 28
gaatttgccc aacgccacgg ggaatcgcct gactgcggcg ctgcattaac tctttattgc      60
tgttcattcg cattctccag atgggaatta gccatggtcc atatgaatat               110

<210> SEQ ID NO 29
<211> LENGTH: 73
<212> TYPE: DNA
<213> ORGANISM: Artificial Sequence
<220> FEATURE:
<223> OTHER INFORMATION: Synthetic  Primer MS220

<400> SEQUENCE: 29
gcaagagtaa atctgcgtat cttcatacca tgactcataa aggagatacc ccggtgtagg      60
ctggagctgc ttc                                                         73

<210> SEQ ID NO 30
<211> LENGTH: 71
<212> TYPE: DNA
<213> ORGANISM: Artificial Sequence
<220> FEATURE:
<223> OTHER INFORMATION: Synthetic Primer MS217

<400> SEQUENCE: 30
accgcaggtc tgaaaagacc tgcgagtata tcagagctga atatgtcgcg catatgaata      60
tcctccttag t                                                           71

<210> SEQ ID NO 31
<211> LENGTH: 61
<212> TYPE: DNA
<213> ORGANISM: Artificial Sequence
<220> FEATURE:
<223> OTHER INFORMATION: Synthetic Primer MS223

<400> SEQUENCE: 31
tcgattcgtg aataagtggc ttaatattat tcattttaaa gcaagagtaa atctgcgtat      60
c                                                                      61

<210> SEQ ID NO 32
<211> LENGTH: 57
<212> TYPE: DNA
<213> ORGANISM: Artificial Sequence
<220> FEATURE:
<223> OTHER INFORMATION: Synthetic Primer MS224

<400> SEQUENCE: 32
gccactttct actcctggac cgcaggtctg aaaagacctg cgagtatatc agagctg        57
```

<210> SEQ ID NO 33
<211> LENGTH: 58
<212> TYPE: DNA
<213> ORGANISM: Artificial Sequence
<220> FEATURE:
<223> OTHER INFORMATION: Synthetic Primer DE081

<400> SEQUENCE: 33
aaaagaattc ttaattaatt ctagaaggag gtttcatatg ttcacgggaa gtattgtc        58

<210> SEQ ID NO 34
<211> LENGTH: 33
<212> TYPE: DNA
<213> ORGANISM: Artificial Sequence
<220> FEATURE:
<223> OTHER INFORMATION: Synthetic Primer DE082

<400> SEQUENCE: 34
agcgatggct ttgaaatact gatacaaacc ttc                                   33

<210> SEQ ID NO 35
<211> LENGTH: 33
<212> TYPE: DNA
<213> ORGANISM: Artificial Sequence
<220> FEATURE:
<223> OTHER INFORMATION: Synthetic Primer DE083

<400> SEQUENCE: 35
gaaggtttgt atcagtattt caaagccatc gct                                   33

<210> SEQ ID NO 36
<211> LENGTH: 54
<212> TYPE: DNA
<213> ORGANISM: Artificial Sequence
<220> FEATURE:
<223> OTHER INFORMATION: Synthetic primer DE084

<400> SEQUENCE: 36
cccgagctcg tttaaactta attaagacta gttttacagc aaaccggcat gctt            54

<210> SEQ ID NO 37
<211> LENGTH: 63
<212> TYPE: DNA
<213> ORGANISM: Artificial Sequence
<220> FEATURE:
<223> OTHER INFORMATION: Synthetic DNA fragment

<400> SEQUENCE: 37
tttttctaga ttgacagcta gctcagtcct aggtataatg ctagcactag tgtttaaacc      60
ccc                                                                    63

<210> SEQ ID NO 38
<211> LENGTH: 65
<212> TYPE: DNA
<213> ORGANISM: Artificial Sequence
<220> FEATURE:
<223> OTHER INFORMATION: Synthetic Primer DE118

<400> SEQUENCE: 38
tgtcccatgt gttgggaggg gccttttta cctggagata tgactgtgta ggctggagct       60
gcttc                                                                  65

<210> SEQ ID NO 39

<211> LENGTH: 65
<212> TYPE: DNA
<213> ORGANISM: Artificial Sequence
<220> FEATURE:
<223> OTHER INFORMATION: Synthetic Primer DE119

<400> SEQUENCE: 39
tgtcccatgt gttgggaggg gccttttttta cctggagata tgactgtgta ggctggagct    60
gcttc    65

<210> SEQ ID NO 40
<211> LENGTH: 65
<212> TYPE: DNA
<213> ORGANISM: Artificial Sequence
<220> FEATURE:
<223> OTHER INFORMATION: Synthetic Primer DE122

<400> SEQUENCE: 40
gtttgagcag gctatgatta aggaaggatt ttccaggagg aacacgtgta ggctggagct    60
gcttc    65

<210> SEQ ID NO 41
<211> LENGTH: 65
<212> TYPE: DNA
<213> ORGANISM: Artificial Sequence
<220> FEATURE:
<223> OTHER INFORMATION: Synthetic Primer  DE123

<400> SEQUENCE: 41
tatttgttaa cagcacgtta ctcgcccgga agccgctctg gcaagatggg aattagccat    60
ggtcc    65

<210> SEQ ID NO 42
<211> LENGTH: 65
<212> TYPE: DNA
<213> ORGANISM: Artificial Sequence
<220> FEATURE:
<223> OTHER INFORMATION: Synthetic Primer DE106

<400> SEQUENCE: 42
gtgttttctt attactttca aggtcttgca cttggggcgg ctatggtgta ggctggagct    60
gcttc    65

<210> SEQ ID NO 43
<211> LENGTH: 65
<212> TYPE: DNA
<213> ORGANISM: Artificial Sequence
<220> FEATURE:
<223> OTHER INFORMATION: Synthetic Primer DE107

<400> SEQUENCE: 43
ctaactgaac aaggcttgtg catgagcaat accgtctctc gccagatggg aattagccat    60
ggtcc    65

<210> SEQ ID NO 44
<211> LENGTH: 71
<212> TYPE: DNA
<213> ORGANISM: Artificial Sequence
<220> FEATURE:
<223> OTHER INFORMATION: Synthetic Primer MS286

<400> SEQUENCE: 44
ccgtttatgt tgccagacag cgctactgat taagcggatt ttttcgcttt catatgaata    60

```
tcctccttag t                                                          71
```

<210> SEQ ID NO 45
<211> LENGTH: 70
<212> TYPE: DNA
<213> ORGANISM: Artificial Sequence
<220> FEATURE:
<223> OTHER INFORMATION: Synthetic Primer MS287

<400> SEQUENCE: 45

```
cgagcagatg atttactaaa aaagtttaac attatcagga gagcattatg gtgtaggctg    60
gagctgcttc                                                            70
```

<210> SEQ ID NO 46
<211> LENGTH: 70
<212> TYPE: DNA
<213> ORGANISM: Artificial Sequence
<220> FEATURE:
<223> OTHER INFORMATION: Synthetic Primer MS289

<400> SEQUENCE: 46

```
tggctccctg acgttttttt agccacgtat caattatagg tacttccatg gtgtaggctg    60
gagctgcttc                                                            70
```

<210> SEQ ID NO 47
<211> LENGTH: 71
<212> TYPE: DNA
<213> ORGANISM: Artificial Sequence
<220> FEATURE:
<223> OTHER INFORMATION: Synthetic Primer MS290

<400> SEQUENCE: 47

```
gcagcgcaaa gctgcggatg atgacgagat tactgctgct gtgcagactg catatgaata    60
tcctccttag t                                                          71
```

<210> SEQ ID NO 48
<211> LENGTH: 71
<212> TYPE: DNA
<213> ORGANISM: Artificial Sequence
<220> FEATURE:
<223> OTHER INFORMATION: Synthetic Primer MS292

<400> SEQUENCE: 48

```
ctcccctgga atgcagggga gcggcaagat taaaccagtt cgttcgggca catatgaata    60
tcctccttag t                                                          71
```

<210> SEQ ID NO 49
<211> LENGTH: 70
<212> TYPE: DNA
<213> ORGANISM: Artificial Sequence
<220> FEATURE:
<223> OTHER INFORMATION: Synthetic Primer MS293

<400> SEQUENCE: 49

```
tatttttagt agcttaaatg tgattcaaca tcactggaga aagtcttatg gtgtaggctg    60
gagctgcttc                                                            70
```

<210> SEQ ID NO 50
<211> LENGTH: 48
<212> TYPE: DNA
<213> ORGANISM: Artificial Sequence
<220> FEATURE:

<223> OTHER INFORMATION: Synthetic Primer FS011

<400> SEQUENCE: 50
tcccctagga ttcaggaggt ttttatggag tgggaagaga tatataaa         48

<210> SEQ ID NO 51
<211> LENGTH: 38
<212> TYPE: DNA
<213> ORGANISM: Artificial Sequence
<220> FEATURE:
<223> OTHER INFORMATION: Synthetic Primer FS008

<400> SEQUENCE: 51
ccttaagtcg acaaattcta aatctctttt ttaaattc                    38

<210> SEQ ID NO 52
<211> LENGTH: 39
<212> TYPE: DNA
<213> ORGANISM: Artificial Sequence
<220> FEATURE:
<223> OTHER INFORMATION: Synthetic Primer JRG047

<400> SEQUENCE: 52
ttcaggatcc tgcgcatgct agctatagtt ctagaggta                   39

<210> SEQ ID NO 53
<211> LENGTH: 53
<212> TYPE: DNA
<213> ORGANISM: Artificial Sequence
<220> FEATURE:
<223> OTHER INFORMATION: Synthetic Primer JRG048

<400> SEQUENCE: 53
catacgatag ctcataaaaa cctcctcgca gttagcgaat agaaaagccg ttg   53

<210> SEQ ID NO 54
<211> LENGTH: 55
<212> TYPE: DNA
<213> ORGANISM: Artificial Sequence
<220> FEATURE:
<223> OTHER INFORMATION: Syntheti Primer JRG049

<400> SEQUENCE: 54
gaggaggttt ttatgagcta tcgtatgagc tatcgtatgt ttgattatct ggtgc  55

<210> SEQ ID NO 55
<211> LENGTH: 35
<212> TYPE: DNA
<213> ORGANISM: Artificial Sequence
<220> FEATURE:
<223> OTHER INFORMATION: Synthetic Primer JRG050

<400> SEQUENCE: 55
tctttcatga actcagaatg cctggcggaa aatcg                       35

<210> SEQ ID NO 56
<211> LENGTH: 1053
<212> TYPE: DNA
<213> ORGANISM: Aspergillus terreus

<400> SEQUENCE: 56
atgccactgg ttgctcaaaa tccactgcca cgtgctattc tgggtctgat gactttcggt    60
ccgagcgaaa gcaaaggtgc gcgtatcact tccctggatg agtttaacaa gtgcctggat   120
tacttccagc agcagggctt ccaggaaatc gataccgcgc gcatctacgt cggcggtgaa   180

```
caggaggcat tcacggcgca ggcaaagtgg aaagaacgcg gcctgacgct ggcgactaag      240
tggtatccgc agtacccggg tgcgcacaaa ccgatgtcc tgcgtcagaa cctggagctg       300
tccctgaaag aactgggcac gaaccaggtc gatatcttct atctgcacgc cgcggatcgt      360
tctgtgccgt tcgcggaaac tctggaaact gttaacgaac tgcacaaaga aggcaaattt      420
gttcagctgg gtctgtctaa ctacaccgct ttcgaagtag ctgaaatcgt gaccctgtgt      480
aacgagcgtg gttgggttcg tccgactatc taccaggcga tgtataacgc tatcacccgt      540
aacatcgaaa ctgaactgat cccggcgtgc aagcgttacg gtattgacat tgttatctac      600
aacccactgg cgggtggcct gttcagcggc aaatacaaag cacaggacat cccggctgaa      660
ggtcgttaca gcgaccaatc ttccatgggc cagatgtacc gcaaccgtta ctttaaggac      720
gcaacctttg acgctctgcg cctgatcgaa ccggttgttg cgaagcacgg cctgacgatg      780
ccggaaaccg cgttccgctg gtccaccac cactccgcac tgaacatgga agatggcggc      840
cgtgacggca tcattctggg tgtaagcagc ctggctcagc tggaaaacaa cctgaaagac      900
attcagaaag gtccgctgcc gcaggaggtt gtagacgtcc tggatcaggc ttggctggtg      960
gctaagccga cggctccaaa ctactggcat ctggacctga atacacgta cgacacccag     1020 gaagctctgt tcaaaccgaa atctaaggcg taa                                  1053
```

<210> SEQ ID NO 57
<211> LENGTH: 350
<212> TYPE: PRT
<213> ORGANISM: Aspergillus terreus

<400> SEQUENCE: 57

Met Pro Leu Val Ala Gln Asn Pro Leu Pro Arg Ala Ile Leu Gly Leu
1               5                   10                  15

Met Thr Phe Gly Pro Ser Glu Ser Lys Gly Ala Arg Ile Thr Ser Leu
            20                  25                  30

Asp Glu Phe Asn Lys Cys Leu Asp Tyr Phe Gln Gln Gly Phe Gln
        35                  40                  45

Glu Ile Asp Thr Ala Arg Ile Tyr Val Gly Gly Glu Gln Glu Ala Phe
    50                  55                  60

Thr Ala Gln Ala Lys Trp Lys Glu Arg Gly Leu Thr Leu Ala Thr Lys
65                  70                  75                  80

Trp Tyr Pro Gln Tyr Pro Gly Ala His Lys Pro Asp Val Leu Arg Gln
                85                  90                  95

Asn Leu Glu Leu Ser Leu Lys Glu Leu Gly Thr Asn Gln Val Asp Ile
            100                 105                 110

Phe Tyr Leu His Ala Ala Asp Arg Ser Val Pro Phe Ala Glu Thr Leu
        115                 120                 125

Glu Thr Val Asn Glu Leu His Lys Glu Gly Lys Phe Val Gln Leu Gly
    130                 135                 140

Leu Ser Asn Tyr Thr Ala Phe Glu Val Ala Glu Ile Val Thr Leu Cys
145                 150                 155                 160

Asn Glu Arg Gly Trp Val Arg Pro Thr Ile Tyr Gln Ala Met Tyr Asn
                165                 170                 175

Ala Ile Thr Arg Asn Ile Glu Thr Glu Leu Ile Pro Ala Cys Lys Arg
            180                 185                 190

Tyr Gly Ile Asp Ile Val Ile Tyr Asn Pro Leu Ala Gly Gly Leu Phe
        195                 200                 205

Ser Gly Lys Tyr Lys Ala Gln Asp Ile Pro Ala Glu Gly Arg Tyr Ser

Asp Gln Ser Ser Met Gly Gln Met Tyr Arg Asn Arg Tyr Phe Lys Asp
225                 230                 235                 240

Ala Thr Phe Asp Ala Leu Arg Leu Ile Glu Pro Val Val Ala Lys His
            245                 250                 255

Gly Leu Thr Met Pro Glu Thr Ala Phe Arg Trp Val His His Ser
        260                 265                 270

Ala Leu Asn Met Glu Asp Gly Gly Arg Asp Gly Ile Ile Leu Gly Val
            275                 280                 285

Ser Ser Leu Ala Gln Leu Glu Asn Asn Leu Lys Asp Ile Gln Lys Gly
        290                 295                 300

Pro Leu Pro Gln Glu Val Val Asp Val Leu Asp Gln Ala Trp Leu Val
305                 310                 315                 320

Ala Lys Pro Thr Ala Pro Asn Tyr Trp His Leu Asp Leu Lys Tyr Thr
                325                 330                 335

Tyr Asp Thr Gln Glu Ala Leu Phe Lys Pro Lys Ser Lys Ala
            340                 345                 350

<210> SEQ ID NO 58
<211> LENGTH: 870
<212> TYPE: DNA
<213> ORGANISM: Arabidopsis thaliana

<400> SEQUENCE: 58
atggaagtag gttttctggg tctgggcatt atgggtaaag ctatgtccat gaacctgctg      60
aaaaacggtt tcaaagttac cgtgtggaac cgcactctgt ctaaatgtga tgaactggtt     120
gaacacggtg caagcgtgtg cgagtctccg gctgaggtga tcaagaaatg caaatacacg     180
atcgcgatgc tgagcgatcc gtgtgcagct ctgtctgttg ttttcgataa aggcggtgtt     240
ctggaacaga tctgcgaggg taagggctac atcgacatgt ctaccgtcga cgcggaaact     300
agcctgaaaa ttaacgaagc gatcacgggc aaaggtggcc gttttgtaga aggtcctgtt     360
agcggttcca aaaagccggc agaagacggc cagctgatca tcctggcagc aggcgacaaa     420
gcactgttcg aggaatccat cccggccttt gatgtactgg caaacgttc cttttatctg     480
ggtcaggtgg gtaacggtgc gaaaatgaaa ctgattgtta acatgatcat gggttctatg     540
atgaacgcgt ttagcgaagg tctggtactg cagataaaa gcggtctgtc tagcgacacg     600
ctgctggata ttctggatct gggtgctatg acgaatccga tgttcaaagg caaaggtccg     660
tccatgacta atccagctac cccaccggct ttcccgctga acaccagca gaaagacatg     720
cgtctggctc tggctctggg cgacgaaaac gctgttagca tgccggtcgc tgcggctgcg     780
aacgaagcct tcaagaaagc ccgtagcctg ggcctgggcg atctggactt ttctgctgtt     840
atcgaagcgg taaaattctc tcgtgaataa                                     870

<210> SEQ ID NO 59
<211> LENGTH: 289
<212> TYPE: PRT
<213> ORGANISM: Arabidopsis thaliana

<400> SEQUENCE: 59

Met Glu Val Gly Phe Leu Gly Leu Gly Ile Met Gly Lys Ala Met Ser
1               5                   10                  15

Met Asn Leu Leu Lys Asn Gly Phe Lys Val Thr Val Trp Asn Arg Thr
            20                  25                  30

Leu Ser Lys Cys Asp Glu Leu Val Glu His Gly Ala Ser Val Cys Glu

|   |   | 35 |   |   | 40 |   |   |   | 45 |   |   |   |
|---|---|---|---|---|---|---|---|---|---|---|---|---|
| Ser | Pro | Ala | Glu | Val | Ile | Lys | Lys | Cys | Lys | Tyr | Thr | Ile | Ala | Met | Leu |
| 50 |   |   |   | 55 |   |   |   |   | 60 |   |   |   |

Ser Pro Ala Glu Val Ile Lys Lys Cys Lys Tyr Thr Ile Ala Met Leu
50                    55                       60

Ser Asp Pro Cys Ala Ala Leu Ser Val Val Phe Asp Lys Gly Gly Val
65                    70                  75                     80

Leu Glu Gln Ile Cys Glu Gly Lys Gly Tyr Ile Asp Met Ser Thr Val
                85                      90                    95

Asp Ala Glu Thr Ser Leu Lys Ile Asn Glu Ala Ile Thr Gly Lys Gly
                100                 105                  110

Gly Arg Phe Val Glu Gly Pro Val Gly Ser Lys Lys Pro Ala Glu
            115                 120                125

Asp Gly Gln Leu Ile Ile Leu Ala Ala Gly Asp Lys Ala Leu Phe Glu
            130                 135                 140

Glu Ser Ile Pro Ala Phe Asp Val Leu Gly Lys Arg Ser Phe Tyr Leu
145                 150                 155                    160

Gly Gln Val Gly Asn Gly Ala Lys Met Lys Leu Ile Val Asn Met Ile
                165                 170                 175

Met Gly Ser Met Met Asn Ala Phe Ser Glu Gly Leu Val Leu Ala Asp
            180                 185                 190

Lys Ser Gly Leu Ser Ser Asp Thr Leu Leu Asp Ile Leu Asp Leu Gly
        195                 200                 205

Ala Met Thr Asn Pro Met Phe Lys Gly Lys Gly Pro Ser Met Thr Lys
210                 215                 220

Ser Ser Tyr Pro Pro Ala Phe Pro Leu Lys His Gln Gln Lys Asp Met
225                 230                 235                 240

Arg Leu Ala Leu Ala Leu Gly Asp Glu Asn Ala Val Ser Met Pro Val
            245                 250                 255

Ala Ala Ala Ala Asn Glu Ala Phe Lys Lys Ala Arg Ser Leu Gly Leu
                260                 265                 270

Gly Asp Leu Asp Phe Ser Ala Val Ile Glu Ala Val Lys Phe Ser Arg
        275                 280                 285

Glu

<210> SEQ ID NO 60
<211> LENGTH: 1680
<212> TYPE: DNA
<213> ORGANISM: Artificial Sequence
<220> FEATURE:
<223> OTHER INFORMATION: Synthetic Pseudomonas putida/Zoogloea ramigera polyhydroxyalkanoate synthase fusion gene phaC3/C5

<400> SEQUENCE: 60

```
atgagtaaca agaacaacga tgagctgcag tggcaatcct ggttcagcaa ggcgcccacc      60
accgaggcga acccgatggc caccatgttg caggatatcg gcgttgcgct caaaccggaa     120
gcgatggagc agctgaaaaa cgattatctg cgtgacttca ccgcgttgtg gcaggatttt     180
ttggctggca aggcgccagc cgtcagcgac cgccgcttca gctcggcagc ctggcagggc     240
aatccgatgt cggccttcaa tgccgcatct tacctgctca acgccaaatt cctcagtgcc     300
atggtggagg cggtggacac cgcaccccag caaaagcaga aaatacgctt tgccgtgcag     360
caggtgattg atgccatgtc gcccgcgaac ttcctcgcca ccaacccgga agcgcagcaa     420
aaactgattg aaaccaaggg cgagagcctg acgcgtggcc tggtcaatat gctgggcgat     480
atcaacaagg ccatatctc gctgtcggac gaatcggcct ttgaagtggg ccgcaacctg     540
gccattaccc cgggcaccgt gatttacgaa atccgctgt tccagctgat ccagtacacg     600
```

```
ccgaccacgc cgacggtcag ccagcgcccg ctgttgatgg tgccgccgtg catcaacaag    660
ttctacatcc tcgacctgca accggaaaat tcgctggtgc gctacgcggt ggagcagggc    720
aacaccgtgt tcctgatctc gtggagcaat ccggacaagt cgctggccgg caccacctgg    780
gacgactacg tggagcaggg cgtgatcgaa gcgatccgca tcgtccagga cgtcagcggc    840
caggacaagc tgaacatgtt cggcttctgc gtgggcggca ccatcgttgc caccgcactg    900
gcggtactgg cggcgcgtgg ccagcacccg cggccagcc tgaccctgct gaccaccttc    960
ctcgacttca gcgacaccgg cgtgctcgac gtcttcgtcg atgaaaccca ggtcgcgctg   1020
cgtgaacagc aattgcgcga tggcggcctg atgccgggcc gtgacctggc ctcgaccttc   1080
tcgagcctgc gtccgaacga cctggtatgg aactatgtgc agtcgaacta cctcaaaggc   1140
aatgagccgg cggcgtttga cctgctgttc tggaattcgg acagcaccaa tttgccgggc   1200
ccgatgttct gctggtacct cgcaacacc tacctggaaa acagcctgaa agtgccgggc   1260
aagctgacgg tggccggcga aaagatcgac ctcggcctga tcgacgcccc ggccttcatc   1320
tacggttcgc gcgaagacca catcgtgccg tggatgtcgg cgtacggttc gctcgacatc   1380
ctcaaccagg gcaagccggg cgccaaccgc ttcgtgctgg gcgcgtccgg ccatatcgcc   1440
ggcgtgatca actcggtggc caagaacaag cgcagctact ggatcaacga cggtggcgcc   1500
gccgatgccc aggcctggtt cgatggcgcg caggaagtgc cgggcagctg gtggccgcaa   1560
tgggccgggt tcctgaccca gcatggcggc aagaaggtca gcccaaggc caagcccggc   1620
aacgcccgct acaccgcgat cgaggcggcg cccggccgtt acgtcaaagc caagggctga   1680
```

<210> SEQ ID NO 61
<211> LENGTH: 559
<212> TYPE: PRT
<213> ORGANISM: Artificial Sequence
<220> FEATURE:
<223> OTHER INFORMATION: Synthetic Amino Acid Sequence: Pseudomonas
putida/Zoogloea ramigera polyhydroxyalkanoate synthase fusion
gene PhaC3/C5

<400> SEQUENCE: 61

```
Met Ser Asn Lys Asn Asn Asp Glu Leu Gln Trp Gln Ser Trp Phe Ser
 1               5                  10                  15

Lys Ala Pro Thr Thr Glu Ala Asn Pro Met Ala Thr Met Leu Gln Asp
            20                  25                  30

Ile Gly Val Ala Leu Lys Pro Glu Ala Met Glu Gln Leu Lys Asn Asp
        35                  40                  45

Tyr Leu Arg Asp Phe Thr Ala Leu Trp Gln Asp Phe Leu Ala Gly Lys
    50                  55                  60

Ala Pro Ala Val Ser Asp Arg Arg Phe Ser Ala Ala Trp Gln Gly
65                  70                  75                  80

Asn Pro Met Ser Ala Phe Asn Ala Ala Ser Tyr Leu Leu Asn Ala Lys
                85                  90                  95

Phe Leu Ser Ala Met Val Glu Ala Val Asp Thr Ala Pro Gln Gln Lys
            100                 105                 110

Gln Lys Ile Arg Phe Ala Val Gln Gln Val Ile Asp Ala Met Ser Pro
        115                 120                 125

Ala Asn Phe Leu Ala Thr Asn Pro Glu Ala Gln Gln Lys Leu Ile Glu
    130                 135                 140

Thr Lys Gly Glu Ser Leu Thr Arg Gly Leu Val Asn Met Leu Gly Asp
145                 150                 155                 160
```

Ile Asn Lys Gly His Ile Ser Leu Ser Asp Glu Ser Ala Phe Glu Val
            165                 170                 175

Gly Arg Asn Leu Ala Ile Thr Pro Gly Thr Val Ile Tyr Glu Asn Pro
        180                 185                 190

Leu Phe Gln Leu Ile Gln Tyr Thr Pro Thr Pro Thr Val Ser Gln
        195                 200                 205

Arg Pro Leu Leu Met Val Pro Pro Cys Ile Asn Lys Phe Tyr Ile Leu
210                 215                 220

Asp Leu Gln Pro Glu Asn Ser Leu Val Arg Tyr Ala Val Glu Gln Gly
225                 230                 235                 240

Asn Thr Val Phe Leu Ile Ser Trp Ser Asn Pro Asp Lys Ser Leu Ala
                245                 250                 255

Gly Thr Thr Trp Asp Asp Tyr Val Glu Gln Gly Val Ile Glu Ala Ile
                260                 265                 270

Arg Ile Val Gln Asp Val Ser Gly Gln Asp Lys Leu Asn Met Phe Gly
            275                 280                 285

Phe Cys Val Gly Gly Thr Ile Val Ala Thr Ala Leu Ala Val Leu Ala
    290                 295                 300

Ala Arg Gly Gln His Pro Ala Ala Ser Leu Thr Leu Thr Thr Phe
305                 310                 315                 320

Leu Asp Phe Ser Asp Thr Gly Val Leu Asp Val Phe Val Asp Glu Thr
                325                 330                 335

Gln Val Ala Leu Arg Glu Gln Leu Arg Asp Gly Leu Met Pro
            340                 345                 350

Gly Arg Asp Leu Ala Ser Thr Phe Ser Ser Leu Arg Pro Asn Asp Leu
        355                 360                 365

Val Trp Asn Tyr Val Gln Ser Asn Tyr Leu Lys Gly Asn Glu Pro Ala
    370                 375                 380

Ala Phe Asp Leu Leu Phe Trp Asn Ser Asp Ser Thr Asn Leu Pro Gly
385                 390                 395                 400

Pro Met Phe Cys Trp Tyr Leu Arg Asn Thr Tyr Leu Glu Asn Ser Leu
                405                 410                 415

Lys Val Pro Gly Lys Leu Thr Val Ala Gly Glu Lys Ile Asp Leu Gly
                420                 425                 430

Leu Ile Asp Ala Pro Ala Phe Ile Tyr Gly Ser Arg Glu Asp His Ile
            435                 440                 445

Val Pro Trp Met Ser Ala Tyr Gly Ser Leu Asp Ile Leu Asn Gln Gly
    450                 455                 460

Lys Pro Gly Ala Asn Arg Phe Val Leu Gly Ala Ser Gly His Ile Ala
465                 470                 475                 480

Gly Val Ile Asn Ser Val Ala Lys Asn Lys Arg Ser Tyr Trp Ile Asn
                485                 490                 495

Asp Gly Gly Ala Ala Asp Ala Gln Ala Trp Phe Asp Gly Ala Gln Glu
            500                 505                 510

Val Pro Gly Ser Trp Trp Pro Gln Trp Ala Gly Phe Leu Thr Gln His
    515                 520                 525

Gly Gly Lys Lys Val Lys Pro Lys Ala Lys Pro Gly Asn Ala Arg Tyr
530                 535                 540

Thr Ala Ile Glu Ala Ala Pro Gly Arg Tyr Val Lys Ala Lys Gly
545                 550                 555

<210> SEQ ID NO 62
<211> LENGTH: 1152
<212> TYPE: DNA

<213> ORGANISM: Thiocapsa phenigii

<400> SEQUENCE: 62

```
atggctggtg accacgtcgt ggaatgcctt cgaattcagg aggttttat gaacgatacg      60
gccaacaaga ccagcgactg gctggacatc caacgcaagt actgggagac ctggtcggag    120
ctcggccgca agaccttggg tctggagaag accccggcca atccttgggc cggcgccctc    180
gatcattggt ggcagacggt ctcgcccgcc gccccaacg acctggttcg cgacttcatg     240
gagaagctcg ccgagcaggg caaggccttc ttcggcctca ccgactactt cacgaagggc    300
ctcggcggca gtagcggtac gcagggctgg gacaccctct cgaagaccat cgacgacatg    360
caaaaggcct tcgccagcgg ccggatcgaa ggcgacgaga ccttccgccg cctgatggcc    420
ttctgggaga tgccgctcga caactggcag cgcaccatgt cctcgctgtc cccggtgccc    480
ggcgacctgc tgcgcaacat gccgcacgac caagtcaggg acagcgtcga ccgcatcctc    540
tcggcacccg ggctcggcta cacgcgcgag gagcaggccc gctaccagga tctgatccgc    600
cgctcgctgg agtaccagtc ggccctgaac gaatacaacg gcttcttcgg ccagctcggt    660
gtcaagtccc tcgagcggat gcgcgccttc ctgcagggac aggccgagaa gggcgtcgcc    720
atcgagtcgg cgcgcaccct ctacgacgcc tgggtcggct gctgcgaaga ggtctatgcc    780
gaggaggtca gctccgccga ctacgcgcac atccacggcc gcctcgtcaa cgcccagatg    840
gccctcaagc agcgcatgtc gaccatggtc gacgaggtcc tcggcgcgat gccgctgccg    900
acccgcagcg agctgcgcac gctccaggat cggctccagg agtcgcgcgg cgagggcaag    960
cgccagcgca agagatcga gacgctgaag cggcaggtcg cggccttggc cggcggcgcc   1020
cagcccgcgc cccaggcctc cgcccagccc agcacccggc ccgcgccggc gacggccccg   1080
gcggcgagcg cggcgcccaa gcgcagcacc acgacccgcc gcaagaccac caagcccacc   1140
accggccagt ga                                                       1152
```

<210> SEQ ID NO 63
<211> LENGTH: 367
<212> TYPE: PRT
<213> ORGANISM: Thiocapsa phenigii

<400> SEQUENCE: 63

```
Met Asn Asp Thr Ala Asn Lys Thr Ser Asp Trp Leu Asp Ile Gln Arg
1               5                   10                  15

Lys Tyr Trp Glu Thr Trp Ser Glu Leu Gly Arg Lys Thr Leu Gly Leu
            20                  25                  30

Glu Lys Thr Pro Ala Asn Pro Trp Ala Gly Ala Leu Asp His Trp Trp
        35                  40                  45

Gln Thr Val Ser Pro Ala Ala Pro Asn Asp Leu Val Arg Asp Phe Met
    50                  55                  60

Glu Lys Leu Ala Glu Gln Gly Lys Ala Phe Phe Gly Leu Thr Asp Tyr
65                  70                  75                  80

Phe Thr Lys Gly Leu Gly Gly Ser Ser Gly Thr Gln Gly Trp Asp Thr
            85                  90                  95

Leu Ser Lys Thr Ile Asp Asp Met Gln Lys Ala Phe Ala Ser Gly Arg
            100                 105                 110

Ile Glu Gly Asp Glu Thr Phe Arg Arg Leu Met Ala Phe Trp Glu Met
        115                 120                 125

Pro Leu Asp Asn Trp Gln Arg Thr Met Ser Ser Leu Ser Pro Val Pro
    130                 135                 140
```

```
Gly Asp Leu Leu Arg Asn Met Pro His Asp Gln Val Arg Asp Ser Val
145                 150                 155                 160

Asp Arg Ile Leu Ser Ala Pro Gly Leu Gly Tyr Thr Arg Glu Glu Gln
            165                 170                 175

Ala Arg Tyr Gln Asp Leu Ile Arg Arg Ser Leu Glu Tyr Gln Ser Ala
        180                 185                 190

Leu Asn Glu Tyr Asn Gly Phe Phe Gly Gln Leu Gly Val Lys Ser Leu
    195                 200                 205

Glu Arg Met Arg Ala Phe Leu Gln Gly Gln Ala Glu Lys Gly Val Ala
210                 215                 220

Ile Glu Ser Ala Arg Thr Leu Tyr Asp Ala Trp Val Gly Cys Cys Glu
225                 230                 235                 240

Glu Val Tyr Ala Glu Glu Val Ser Ser Ala Asp Tyr Ala His Ile His
            245                 250                 255

Gly Arg Leu Val Asn Ala Gln Met Ala Leu Lys Gln Arg Met Ser Thr
        260                 265                 270

Met Val Asp Glu Val Leu Gly Ala Met Pro Leu Pro Thr Arg Ser Glu
    275                 280                 285

Leu Arg Thr Leu Gln Asp Arg Leu Gln Glu Ser Arg Gly Glu Gly Lys
290                 295                 300

Arg Gln Arg Gln Glu Ile Glu Thr Leu Lys Arg Gln Val Ala Ala Leu
305                 310                 315                 320

Ala Gly Gly Ala Gln Pro Ala Pro Gln Ala Ser Ala Gln Pro Ser Thr
            325                 330                 335

Arg Pro Ala Pro Ala Thr Ala Pro Ala Ala Ser Ala Ala Pro Lys Arg
        340                 345                 350

Ser Thr Thr Thr Arg Arg Lys Thr Thr Lys Pro Thr Thr Gly Gln
    355                 360                 365

<210> SEQ ID NO 64
<211> LENGTH: 1074
<212> TYPE: DNA
<213> ORGANISM: Thiocapsa phenigii

<400> SEQUENCE: 64
atgtccccat tcccgatcga catccggccc gacaagctga ccgaggagat gctggagtac    60
agccgcaagc tcggcgaggg tatgcagaac ctgctcaagg ccgaccagat cgacacaggc   120
gtcaccccca aggacgtcgt ccaccgcgag acaagctgg tcctctaccg ctaccggcgc    180
ccggcgcagg tggcgaccca gacgatcccg ctgctgatcg tctacgccct cgtcaatcgg   240
ccctacatga ccgacatcca ggaggatcgc tcgacgatca agggcctgct cgccaccggt   300
caggacgtct atctgatcga ctggggctac ccggatcagg ccgaccgggc gctgaccctc   360
gatgactaca tcaacggcta catcgaccgc tgcgtcgact acctgcgcga cccacggc    420 gtcgaccagg tcaacctgct cgggatctgc cagggcgggg ccttcagcct ctgctacacg   480
gccctgcact ccgagaaggt caaaaacctc gtcaccatgg tcacgccggt cgacttccag   540
accccgggca acctgctctc ggcctgggtc agaacgtcg acgtcgacct ggccgtcgac   600
accatgggca catcccgg cgaactgctc aactggacct tcctgtcgct caagcccttc    660
agcctgaccg ccagaagta cgtcaacatg gtcgacctgc tcgacgacga ggacaaggtc   720
aagaacttcc tgcggatgga gaagtggatc ttcgacagcc ggaccaggc cggcgagacc    780 ttccgccagt tcatcaagga cttctaccag cgcaacggct tcatcaacgg cggcgtcctg   840
atcggcgatc aggaggtcga cctgcgcaac atccgctgcc cggtcctgaa catctacccg   900
```

```
atgcaggacc acctggtgcc gccggatgcc tccaaggccc tcgcgggact gacctccagc    960
gaggactaca cggagctcgc cttccccggc gggcacatcg gcatctacgt cagcggcaag   1020
gcgcaggaag gagtcacccc ggcgatcggc cgctggctga acgaacgcgg ctga         1074
```

<210> SEQ ID NO 65
<211> LENGTH: 357
<212> TYPE: PRT
<213> ORGANISM: Thiocapsa phenigii

<400> SEQUENCE: 65

| | | | | | | | | | | | | | | |
|---|---|---|---|---|---|---|---|---|---|---|---|---|---|---|
| Met | Ser | Pro | Phe | Pro | Ile | Asp | Ile | Arg | Pro | Asp | Lys | Leu | Thr | Glu | Glu |
| 1 | | | | 5 | | | | | 10 | | | | | 15 | |
| Met | Leu | Glu | Tyr | Ser | Arg | Lys | Leu | Gly | Glu | Gly | Met | Gln | Asn | Leu | Leu |
| | | | 20 | | | | | 25 | | | | | 30 | | |
| Lys | Ala | Asp | Gln | Ile | Asp | Thr | Gly | Val | Thr | Pro | Lys | Asp | Val | Val | His |
| | | 35 | | | | | 40 | | | | | 45 | | | |
| Arg | Glu | Asp | Lys | Leu | Val | Leu | Tyr | Arg | Tyr | Arg | Pro | Ala | Gln | Val | |
| | 50 | | | | | 55 | | | | | 60 | | | | |
| Ala | Thr | Gln | Thr | Ile | Pro | Leu | Ile | Val | Tyr | Ala | Leu | Val | Asn | Arg | |
| 65 | | | | | 70 | | | | | 75 | | | | | 80 |
| Pro | Tyr | Met | Thr | Asp | Ile | Gln | Glu | Asp | Arg | Ser | Thr | Ile | Lys | Gly | Leu |
| | | | | 85 | | | | | 90 | | | | | 95 | |
| Leu | Ala | Thr | Gly | Gln | Asp | Val | Tyr | Leu | Ile | Asp | Trp | Gly | Tyr | Pro | Asp |
| | | | 100 | | | | | 105 | | | | | 110 | | |
| Gln | Ala | Asp | Arg | Ala | Leu | Thr | Leu | Asp | Asp | Tyr | Ile | Asn | Gly | Tyr | Ile |
| | | 115 | | | | | 120 | | | | | 125 | | | |
| Asp | Arg | Cys | Val | Asp | Tyr | Leu | Arg | Glu | Thr | His | Gly | Val | Asp | Gln | Val |
| 130 | | | | | 135 | | | | | 140 | | | | | |
| Asn | Leu | Leu | Gly | Ile | Cys | Gln | Gly | Gly | Ala | Phe | Ser | Leu | Cys | Tyr | Thr |
| 145 | | | | | 150 | | | | | 155 | | | | | 160 |
| Ala | Leu | His | Ser | Glu | Lys | Val | Lys | Asn | Leu | Val | Thr | Met | Val | Thr | Pro |
| | | | | 165 | | | | | 170 | | | | | 175 | |
| Val | Asp | Phe | Gln | Thr | Pro | Gly | Asn | Leu | Leu | Ser | Ala | Trp | Val | Gln | Asn |
| | | | 180 | | | | | 185 | | | | | 190 | | |
| Val | Asp | Val | Asp | Leu | Ala | Val | Asp | Thr | Met | Gly | Asn | Ile | Pro | Gly | Glu |
| | | 195 | | | | | 200 | | | | | 205 | | | |
| Leu | Leu | Asn | Trp | Thr | Phe | Leu | Ser | Leu | Lys | Pro | Phe | Ser | Leu | Thr | Gly |
| | 210 | | | | | 215 | | | | | 220 | | | | |
| Gln | Lys | Tyr | Val | Asn | Met | Val | Asp | Leu | Leu | Asp | Glu | Asp | Lys | Val | |
| 225 | | | | | 230 | | | | | 235 | | | | | 240 |
| Lys | Asn | Phe | Leu | Arg | Met | Glu | Lys | Trp | Ile | Phe | Asp | Ser | Pro | Asp | Gln |
| | | | | 245 | | | | | 250 | | | | | 255 | |
| Ala | Gly | Glu | Thr | Phe | Arg | Gln | Phe | Ile | Lys | Asp | Phe | Tyr | Gln | Arg | Asn |
| | | | 260 | | | | | 265 | | | | | 270 | | |
| Gly | Phe | Ile | Asn | Gly | Gly | Val | Leu | Ile | Gly | Asp | Gln | Glu | Val | Asp | Leu |
| | | 275 | | | | | 280 | | | | | 285 | | | |
| Arg | Asn | Ile | Arg | Cys | Pro | Val | Leu | Asn | Ile | Tyr | Pro | Met | Gln | Asp | His |
| | 290 | | | | | 295 | | | | | 300 | | | | |

```
Leu Val Pro Pro Asp Ala Ser Lys Ala Leu Ala Gly Leu Thr Ser Ser
305                 310                 315                 320

Glu Asp Tyr Thr Glu Leu Ala Phe Pro Gly Gly His Ile Gly Ile Tyr
                325                 330                 335

Val Ser Gly Lys Ala Gln Glu Gly Val Thr Pro Ala Ile Gly Arg Trp
                340                 345                 350

Leu Asn Glu Arg Gly
            355
```

GREEN PROCESS AND COMPOSITIONS FOR PRODUCING POLY(5HV) AND 5 CARBON CHEMICALS

CROSS REFERENCE TO RELATED APPLICATION

This application claims benefit of and priority to U.S. Provisional Patent Application No. 61/122,250 filed on Dec. 12, 2008, and where permissible is incorporated by reference in its entirety.

FIELD OF THE INVENTION

The invention is generally related to transgenic organisms that produce polyhydroxyalkanoates and co-polymers thereof containing 5-hydroxyvalerate and chemical intermediates containing five carbon atoms (C5 chemicals).

BACKGROUND OF THE INVENTION

Polyhydroxyalkanoates (PHAs) are biodegradable plastics which can be used to make, without limitation, films (e.g., packaging films, agricultural films, mulch film), golf tees, caps and closures, agricultural supports and stakes, paper and board coatings (e.g., for cups, plates, boxes, etc), thermoformed products (e.g., trays, containers, yogurt pots, plant pots, noodle bowls, moldings, etc.), housings (e.g., for electronic items) bags (e.g., trash bags, grocery bags, food bags, compost bags, etc.), hygiene articles (e.g., diapers, feminine hygiene products, incontinence products, disposable wipes, etc.) and coatings for pelleted products (e.g., pelleted fertilizer, herbicides, pesticides, seeds, etc.). PHAs have also been used to develop biomedical devices including sutures, repair devices, repair patches, slings, cardiovascular patches, orthopedic pins, adhesion barriers, stents, guided tissue repair/regeneration devices, articular cartilage repair devices, nerve guides, tendon repair devices, bone marrow scaffolds, and wound dressings.

Polyhydroxyalkanoates can be produced by a fermentation process. Existing fermentation methods for producing polyhydroxyalkanoates utilize wild-type or transgenic microorganisms cultured on specific substrates to produce the desired PHA polymer composition. In many cases the polymers of interest are copolymers of the (D)-isomer of 3-hydroxybutyrate copolymerized with one other 3, 4 or 5-hydroxyacids. These copolymers are produced as granular inclusions inside the cells and are random copolymers. The copolymer poly(3-hydroxybutyrate-co-5-hydroxyvalerate) (PHB5HV) and the homopolymer poly(5-hydroxyvalerate) (P5HV) are industrially useful as materials and plastics with the advantage that they are biodegradable and bioresorbable materials. To date these materials have been produced by feeding petroleum derived 5-carbon substrates like 5-hydroxyvaleric acid (5HV) or 1,5-pentanediol to a microorganism which has the capability to metabolize these substrates to the activated monomer 5HV-Coenzyme A and polymerize it by the action of a PHA polymerase to form the PHB5HV or P5HV polymers, PHB5HV and P5HV polymers produced by these methods are only partly made from renewable resources and expensive due to the high cost of the 5-carbon petroleum substrates. It is highly desirable to use non-petroleum renewable carbon substrates as feedstock for the production of PHV5HV and P5HV polymers both to lower cost and to provide materials that are made entirely from renewable resources. It is also desirable to develop processes for the production of these polymers which reduce the production of greenhouse gasses.

Suitable renewable resources include carbohydrate feedstocks available from agriculture including one or more feedstocks selected from: starch, sucrose, glucose, lactose, fructose, xylose, maltose, arabinose and amino acid feedstocks including lysine and proline.

Therefore, it is an object of the invention to provide recombinant organisms and processes whereby genes can be introduced in wild-type or genetically engineered polyhydroxyalkanoate producers to create new strains that synthesize monomers, such as 5-hydroxyvalerate, that are produced from substrates that are not derived from petroleum.

A further object of the invention is to provide techniques and procedures to stably engineer recombinant organisms that synthesize PHAs containing 5-hydroxyvalerate either as sole constituent or as a co-monomer.

It is another object of the invention to provide techniques and procedures to stably engineer recombinant organisms that synthesize 5 carbon chemicals such as 5-aminopentanoate (5AP), glutarate, and 1,5 pentanediol (PDO).

SUMMARY OF THE INVENTION

HV Containing PHA Biopolymers

Recombinant hosts for producing polyhydroxyalkanoates (PHAs) comprising 5-hydroxyvalerate (5HV) monomers and methods of producing PHAs comprising 5HV monomers from renewable carbon substrates are provided. Certain recombinant hosts that produce 5 carbon chemicals such as 5-aminopentanoate (5AP), 5HV, glutarate, and 1,5 pentanediol (PDO) are also provided.

One embodiment provides a recombinant host expressing genes encoding a polyhydroxyalkanoate (PHA) synthase and a 5-hydroxyvalerate-CoA (5HV-CoA) transferase or 5HV-CoA synthetase and at least one transgene encoding a heterologous enzyme involved in lysine catabolic pathways wherein the host produces a PHA polymer containing 5HV monomers when the organism is provided with a renewable carbon substrate selected from: lysine, starch, sucrose, glucose, lactose, frucrose, xylose, maltose, arabinose or combinations thereof and the level of SHY monomer produced is higher than in the absence of expression of said transgene(s). An exemplary host expresses one or more genes encoding lysine 2-monooxygenase, 5-aminopentanamidase, 5-aminopetanoate transaminase, glutarate semialdehyde reductase, 5-hydroxyvalerate CoA-transferase, and polyhydroxyalkanoate synthase to produce a PHA polymer containing 5HV monomers. Preferably the host has deletions or mutations in genes encoding glutarate semialdehyde dehydrogenase and/or lysine exporter encoding genes. Particularly suitable hosts also have the ability to overproduce lysine and are resistant to toxic lysine analogs, like S-(2-aminoethyl) cysteine.

In a further embodiment one or more of the genes encoding PHA synthase, 5HV-CoA transferase or 5HV-CoA synthetase is also expressed from a transgene.

In another embodiment the recombinant organism is fed lysine in combination with one or more renewable carbon substrates selected from: starch, sucrose, glucose, lactose, frucrose, xylose, maltose, arabinose or combinations thereof such that the 5HV containing PHA polymer is produced and the polymer is recovered from the cells.

In another embodiment the recombinant organism is fed one or more renewable carbon substrates selected from: starch, sucrose, glucose, lactose, fructose, xylose, maltose, arabinose or combinations thereof such that the 5HV containing PHA polymer is produced and the polymer is recovered from the cells.

The polymers produced by the recombinant hosts can be homopolymers or copolymers of 5HV monomers. A preferred copolymer is PHB5HV. Other useful polymers produced by the recombinant hosts are the copolymers poly(3-hydroxypropionate-co-5-hydroxyvalerate) and poly(4-hydroxybutyrate-co-5-hydroxyvalerate) and the homopolymer P5HV.

The host can be prokaryotic or eukaryotic. Preferred prokaryotic hosts are *E. coli, Ralstonia eutropha, Alcaligenes latus* and *C. glutamicum*.

Recombinant hosts for producing PHA polymers from lysine, or one or more renewable carbon substrate selected from starch, sucrose, glucose, lactose, fructose, xylose, maltose, arabinose or a combinations thereof are also provided. An exemplary host expresses lysine 2-monooxygenase, 5-aminopentanamidase, 5-aminopetanoate transaminase, glutarate semialdehyde reductase, 5-hydroxyvalerate CoA-transferase, and polyhydroxyalkanoate synthase to produce a polymer including 5HV. The polymer is produced using lysine and one or more renewable carbon substrate selected from starch, sucrose, glucose, lactose, fructose, xylose, maltose and arabinose as a feedstock. Preferably the host has deletions in glutarate semialdehyde dehydrogenase and lysine export encoding genes.

1,5-Pentanediol Production

Another recombinant host is genetically engineered to overexpress 5-hydroxyvalerate CoA transferase, CoA dependent propionaldehyde dehydrogenase, and 1,3-propanediol dehydrogenase to produce 1,5 pentanediol. 1,5 pentanediol is produced using 5-hydroxyvalerate, lysine starch, sucrose, glucose, lactose, frucrose, xylose, maltose and arabinose alone or in combinations as feedstock. Preferably the recombinant host has deletions in adhE, ldhA, and ackA-pta and expresses lysine 2-monooxygenase, 5-aminopentanamidase, 5-aminopetanoate transaminase and one or more glutarate or succinate semialdehyde reductase encoding genes. Particularly suitable hosts have the ability to overproduce lysine and are resistant to toxic lysine analogs, like S-(2-aminoethyl) cysteine. Preferably, the organism has a reduced or no glutarate semialdehyde dehydrogenase activity.

A method for producing 1,5-pentanediol from renewable carbon substrates is provided where a recombinant organism is fed a renewable carbon substrate and 1,5-pentanediol is produced, secreted to the medium and recovered therefrom.

In another embodiment the invention provides 1,5-pentandiol produced from renewable resources.

Glutaric Acid Production

Recombinant hosts for overproducing glutarate (glutaric acid) from lysine, or one or more renewable carbon substrate selected from starch, sucrose, glucose, lactose, fructose, xylose, maltose and arabinose, or a combination thereof are also provided. An exemplary host expresses lysine 2-monooxygenase, 5-aminopentanamidase, 5-aminopetanoate transaminase and one or more glutarate semialdehyde dehydrogenase encoding genes. Particularly suitable hosts have the ability to overproduce lysine and are resistant to toxic lysine analogs, like S-(2-aminoethyl) cysteine.

A method for overproducing glutarate from renewable carbon substrates is provided where a recombinant organism is fed a renewable carbon substrate selected from lysine, starch, sucrose, glucose, lactose, frucrose, xylose, maltose and arabinose, or combinations thereof and glutarate is overproduced, secreted to the medium and recovered therefrom.

BRIEF DESCRIPTIONS OF THE DRAWINGS

FIG. 1 is a schematic diagram showing the various 5-carbon molecules that can be produced biologically from renewable resources in some instances these renewable resource based molecules can be interconverted using standard chemistry and used to make polymers etc. by chemical polymerization processes.

FIG. 2A is a schematic diagram showing biochemical pathways to 5-hydroxyvalerate containing polyhydroxyalkanoate polymers, and 5-carbon chemicals such as 5-aminopentanoate (5-APO), glutarate, δ-valerolactone (DVL) and 1,5 pentanediol. Also shown are competing metabolic pathways that may have to be removed or the activities reduced (as indicated by a cross (X)) to achieve optimal carbon flux to the desired products listed above. FIG. 2B shows enzymes catalyzing the biosynthetic reactions: (1) lysine 2-monooxygenase, EC 1.13.12.2; (2) 5-aminopentanamidase (a.k.a. δ-aminovaleramidase), EC 3.5.1.30; (3) 5-aminopentanoate transaminase (a.k.a. δ-aminovalerate transaminase), EC 2.6.1.48; (4) succinate semialdehyde reductase (a.k.a. 5-oxopentanoate reductase), EC 1.1.1.61; (5) CoA-transferase, EC 2.8.3.n; (6) Acyl-CoA synthetase, EC 6.2.1.3; (7) PHA synthase, EC 2.3.1.n; (8) β-ketoacyl-CoA thiolase, EC 2.3.1.9; (9) acetoacetyl-CoA reductase, EC 1.1.1.36; (10) glutarate-semialdehyde dehydrogenase, EC 1.2.1.20.

DETAILED DESCRIPTION OF THE INVENTION

I. Definitions

A number of terms used herein are defined and clarified in the following section.

The term "PHA copolymer" refers to a polymer composed of at least two different hydroxyalkanoic acid monomers.

The term "PHA homopolymer" refers to a polymer that is composed of a single hydroxyalkanoic acid monomer.

As used herein, a "vector" is a replicon, such as a plasmid, phage, or cosmid, into which another DNA segment may be inserted so as to bring about the replication of the inserted segment. The vectors can be expression vectors.

As used herein, an "expression vector" is a vector that includes one or more expression control sequences.

As used herein, an "expression control sequence" is a DNA sequence that controls and regulates the transcription and/or translation of another DNA sequence.

As used herein, "operably linked" means incorporated into a genetic construct so that expression control sequences effectively control expression of a coding sequence of interest.

As used herein, "transformed" and "transfected" encompass the introduction of a nucleic acid into a cell by a number of techniques known in the art.

As used herein "overproduced" means that the particular compound is produced at a higher quantity in the engineered organism as compared to the non-engineered organism.

As used herein the terms "renewable feedstock", "renewable carbon substrate" and "renewable substrate" are all used interchangeably.

"Plasmids" are designated by a lower case "p" preceded and/or followed by capital letters and/or numbers.

As used herein the term "heterologous" means from another host. The other host can be the same or different species.

II. Metabolic Pathways for Producing Polyhydroxyalkanoates and 5 Carbon Chemicals Recombinant organisms having enzymes for the biochemical pathways for production of 5-hydroxyvalerate containing polyhydroxyalkanoate polymers, and 5-carbon chemicals such as 5-aminopentanoate (5AP), 5-hydroxyvalerate (5HV), glutarate, and 1,5 pentanediol (PDO) are provided. Prokaryotic or eukaryotic hosts are genetically engineered to express the enzymes needed to produce 5-hydroxyvalerate, polymers thereof, or the disclosed 5-carbon chemicals from renewable resource based feedstocks. The enzymatic pathways for producing the desired products are provided below.

Figure 2A:
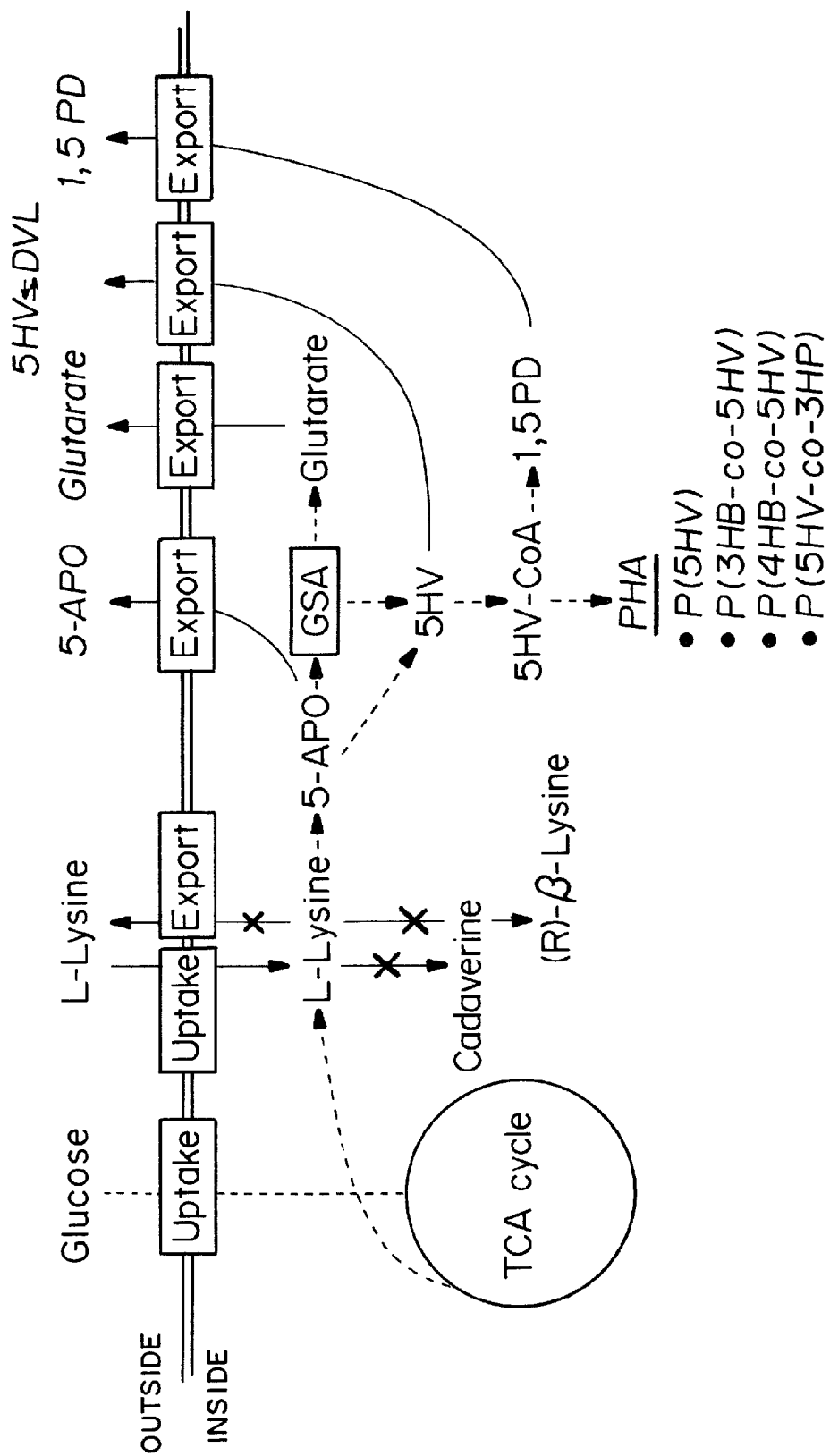

A. 5-aminopentanoate 5-aminopentanoate (5AP) can be produced in two enzymatic steps from L-lysine, an α-amino acid, with 5-aminopentanamide as the intermediate (FIG. 2). The first of these enzymes, lysine 2-monooxygenase is the first enzymatic step in the lysine degradation pathway of various pseudomonad strains (Takeda and Hayaishi, J. Biol. Chem. 241:2733-2736; (1966); Hayaishi, Bacteriol. Rev. 30:720-731 (1966); Reitz and Rodwell, J. Biol. Chem. 245: 3091-3096 (1970); Flashner and Massey, J. Biol. Chem. 249: 2579-2586 (1974)). The gene encoding lysine 2-monooxygenase was identified in *Pseudomonas putida* and called davB (Revelles et al., J. Bacteriol. 187:7500-7510 (2005)). The second enzymatic step converts 5-aminopentanamide to 5AP and is catalyzed by 5-aminopentanamidase (Reitz et al., Anal. Biochem. 28:269-272 (1969); Reitz and Rodwell, J. Biol. Chem. 245: 3091-3096 (1970)), which is encoded by davA in *P. putida* (Revelles et al., J. Bacteriol. 187:7500-7510 (2005)).

Figure 3:
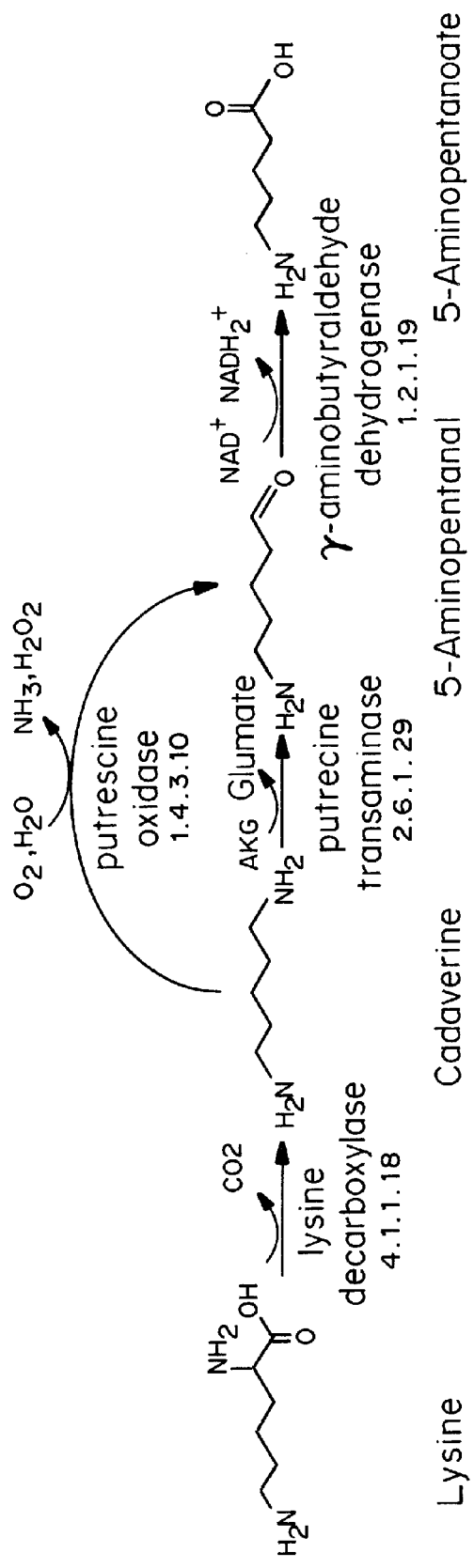
FIG. 3 is a schematic diagram showing biochemical pathways of an alternate route from L-lysine to 5-aminopentanoate via cadaverine and 5-aminopentanal.
Figure 4:
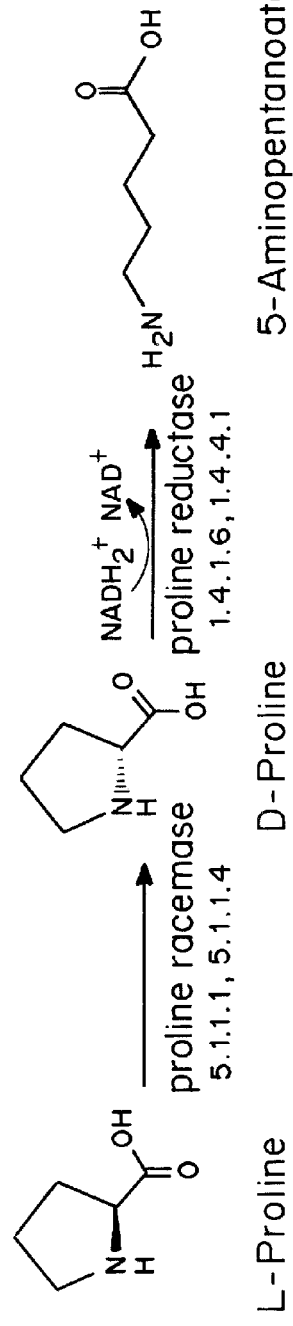
FIG. 4 is a schematic diagram showing biochemical pathways from L-proline to 5-aminopentanoate.

As shown in FIG. 3, an alternate pathway can be utilized to convert L-lysine to 5AP in three enzymatic reactions which include a lysine decarboxylase to produce cadaverine, a putrescine transaminase to form 5-aminopentenal, and a γ-aminobutyraldehyde dehydrogenase to biosynthesize 5AP. As outlined in FIG. 4, 5AP may also be produced from L-proline, instead of L-lysine, in two enzymatic reactions which include a proline racemase to biosynthesize D-proline and a proline reductase to form 5AP.

B. 5-hydroxyvalerate

Biosynthesis of another 5-carbon chemical, 5HV, can occur from 5AP with 2 enzymatic steps as outlined in FIG. 2. 5AP is converted to glutarate semialdehyde by 5AP transaminase (Reitz and Rodwell, J. Biol. Chem. 245: 3091-3096 (1970)) and a gene from *P. putida* which was identified and named davT (Espinosa-Urgel and Ramos, Appl. Environ. Microbiol. 67:5219-5224 (2001)). As outlined in Example 7, several recombinant semialdehyde reductase genes were cloned and tested to investigate which encoded enzyme efficiently converted glutarate semialdehyde to 5HV. The hypothetical protein ATEG_00539 was discovered to efficiently catalyze this reaction and was hence renamed gsaR for glutarate semialdehyde reductase.

Figure 5:
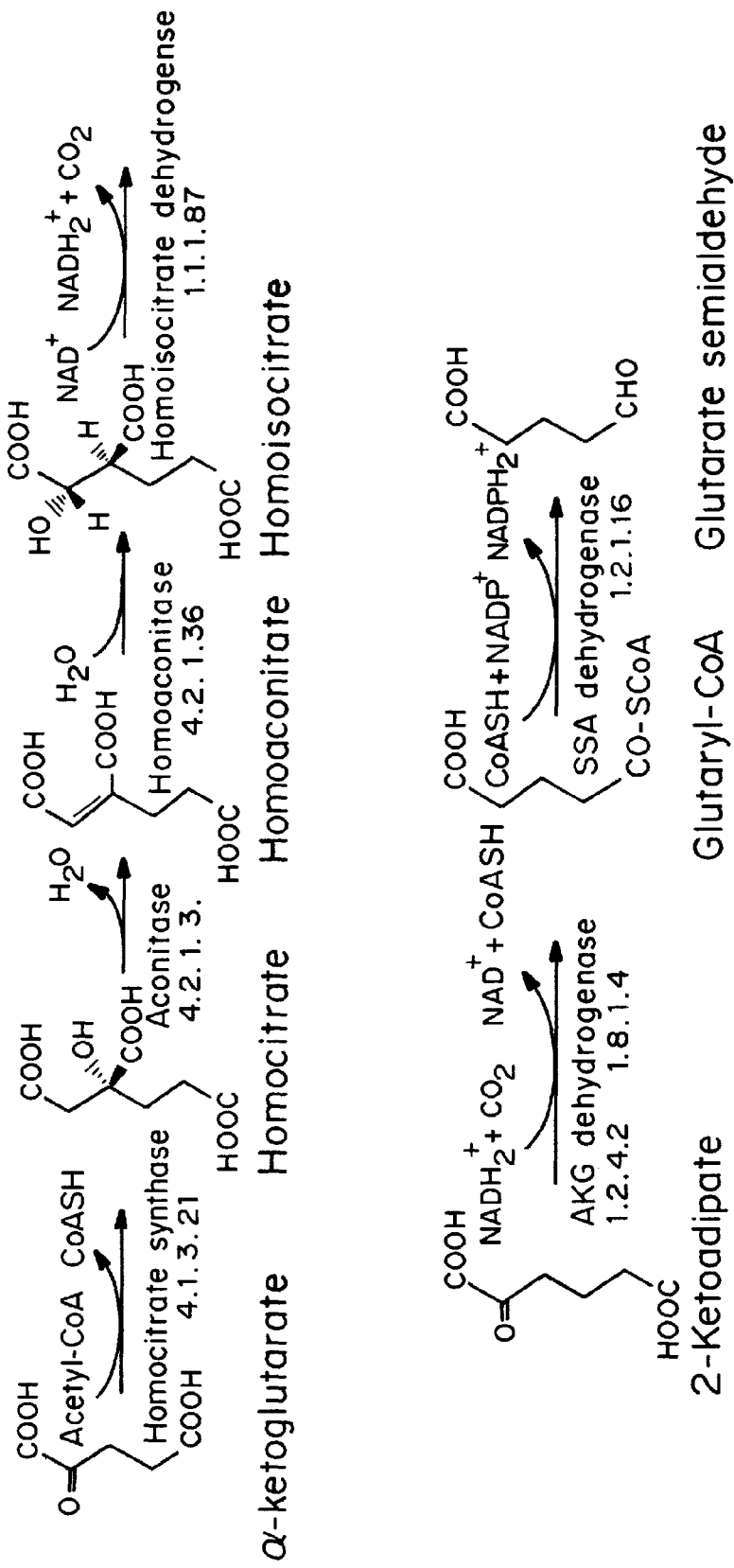
FIG. 5 is a schematic diagram showing biochemical pathways from alpha-ketoglutarate to glutarate semialdehyde, a metabolic intermediate to produce 5-hydroxyvalerate and its derivatives, and glutarate.

In some thermophilic bacteria and lower fungi including yeasts, lysine is synthesized via the α-aminoketoadipate pathway (Xu, Cell Biochem. Biophys. 46:43-64 (2006)) in which 2-ketoadipate is the fourth intermediate and therefore a potential precursor for C5 chemicals such as glutarate and 5HV, as well as for 5HV-containing PHA polymers. This pathway starts from α-ketoglutarate and acetyl-CoA to biosynthesize 2-ketoadipate as shown in FIG. 5. Recombinant *E. coli* host strains expressing these four enzymes were shown to produce 2-ketoadipate (Andi et al., Biochem. 43:11790-11795 (2004); Jia et al., Biochem. J. 396:479-485 (2006); Miyazaki et al., J. Biol. Chem. 278:1864-1871 (2003)). 2-Ketoadipate may be converted by an α-ketoglutarate dehydrogenase to glutaryl-CoA due to the structural similarity of α-ketoglutarate and 2-ketoadipate. Glutaryl-CoA may be converted by an succinic semialdehyde (SSA) dehydrogenase such as succinyl-CoA synthetase (SucD) (Söhling and Gottschalk J. Bacteriol. 178:871-880 (1996)), again due to the structural similarity of succinyl-CoA and glutaryl-CoA.

C. Glutarate

Biosynthesis of the 5-carbon chemical, glutarate, proceeds from glutarate semialdehyde via a dehydrogenase reaction (Ischihara et al., J. Biochem. (Tokyo) 49:154-157 (1961); Reitz and Rodwell, J. Biol. Chem. 245: 3091-3096 (1970)) as outlined in FIG. 2. The davD gene was identified to encode such a glutarate semialdehyde dehydrogenase activity in *P. putida* (Espinosa-Urgel and Ramos, Appl. Environ. Microbiol. 67:5219-5224 (2001); Revelles et al., J. Bacteriol. 186: 3439-3446 (2004)). Glutarate is useful for the production of polymers such as polyesters, polyester polyols and polyamides. The odd number of carbon atoms (i.e. 5) is useful in for example decreasing polymer elasticity. In addition, 1,5-pentanedial is a common plasticizer and precursor to polyesters that is manufactured by hydrogenation of glutarate and its derivatives (Werle and Morawietz, "Alcohols, Polyhydric" in: Ullmann's Encyclopedia of Industrial Chemistry: 2002, Wiley-VCH: Weinheim. DOI 10.1002/14356007.a01_305).

D. poly(5-hydroxyvalerate)

Biosynthesis of a homopolymer consisting of poly(5-hydroxyvalerate) P(5HV)) PHA can proceed from 5HV via 5-hydroxyvalerate-CoA. Two different enzymatic reactions may catalyze the first step, i.e. either by a CoA-transferase as described by Huisman et al. (U.S. Pat. No. 7,229,804), Söhling and Gottschalk (J. Bacteriol. 178:871-880 (1996)), and Eikmanns and Buckel (Biol. Chem. Hoppe-Seyler 371: 1077-1082 (1990)), or by a CoA-synthetase as described by van Beilen et al. (Malec. Microbiol. 6:3121-3136 (1992)). Polymerization of 5-hydroxyvalerate-CoA may be catalyzed by PHA polymerase such as encoded by the *Ralstonia eutropha* phaC1 (Peoples and Sinskey, J. Biol. Chem. 264:15298-

15303 (1989)). Alternatively, the PhaC3/C5 synthase fusion protein may be employed as described by Huisman et al. (U.S. Pat. No. 6,316,262).

E. poly(3-hydroxybutyrate-co-5-hydroxyvalerate)

Biosynthesis of a copolymer including poly(3-hydroxybutyrate-co-5-hydroxyvalerate) (a.k.a. P(3HB-co-5HV)) can occur by supplying 3-hydroxybutyryl-CoA (3HB-CoA) and 5-HV-CoA monomer precursor molecules. As outlined in FIG. 2, 3HB-CoA can be biosynthesized from acetyl-CoA via 2 enzymatic steps: (i.) a β-ketoacyl-CoA thiolase reaction that converts acetyl-CoA to acetoacetyl-CoA (Nishimura et al., J. Biol. Chem. 116:21-27 (1978)) using suitable genes such as, but not limited to, bktB from *Ralstonia eutropha* (Slater et al., J. Bacteriol. 180(8):1979-1987 (1998)) and (ii.) an acetoacetyl-CoA reductase reaction that converts acetoacetyl-CoA to 3HB-CoA (Fukui et al., Biochim. Biophys. Acta 917:365-371 (1987)) using suitable genes such as, but not limited to, phaB from *Bacillus megaterium* (McCool and Cannon, J. Bacteriol. 181(2):585-592 (1999)). As outlined above, PHA copolymer can by synthesized by various PHA synthases.

F. Lysine

Figure 6:
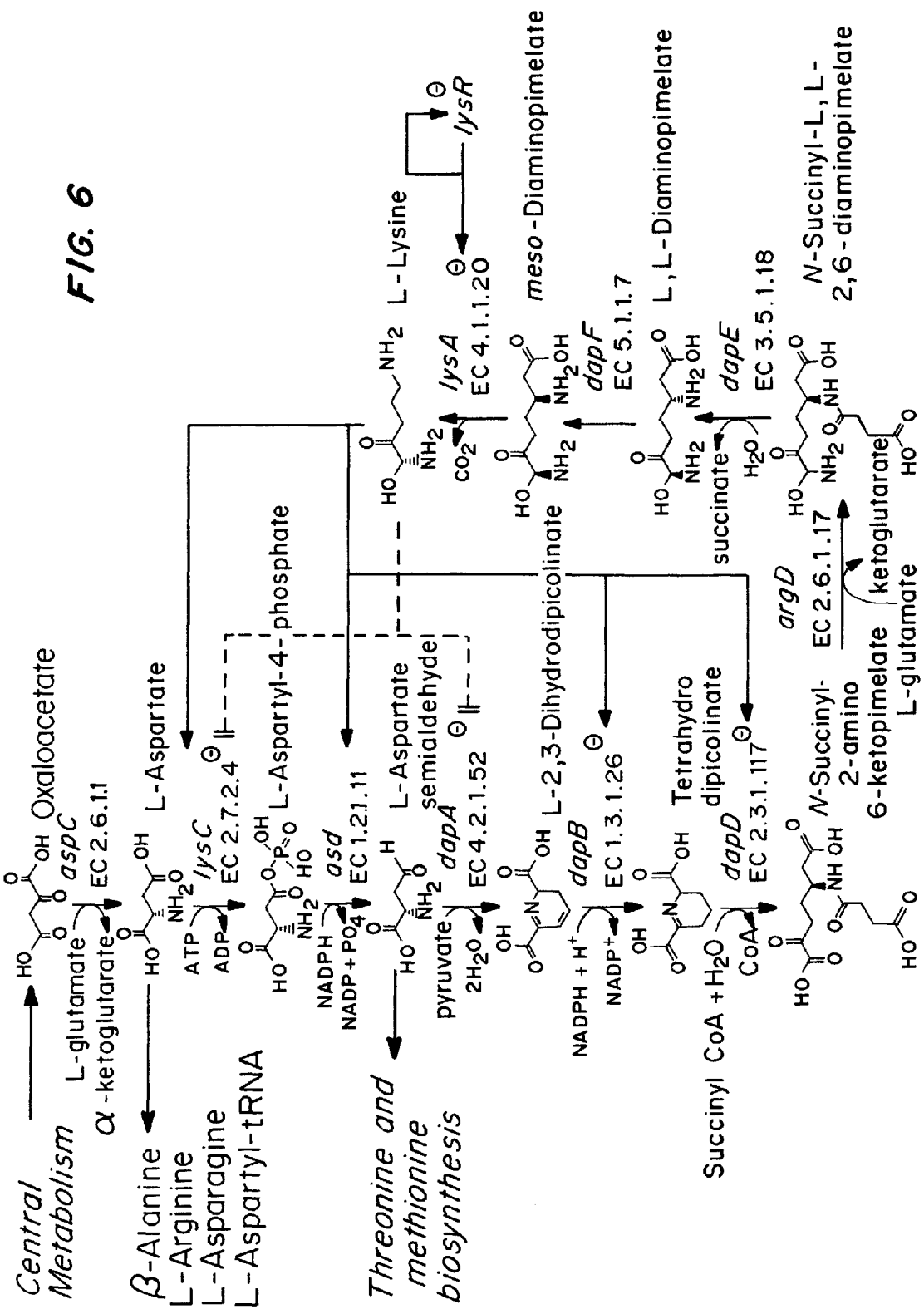
FIG. 6 is a schematic diagram showing biochemical pathways from oxaloacetate, an intermediate of the TCA cycle, to L-lysine.

FIG. 6 outlines the biosynthetic pathway of lysine metabolism in *E. coli*. Dotted and solid lines in the center of the diagram indicate allosteric feedback inhibition and transcriptional repression by L-lysine, respectively, which provide targets for genetic modifications necessary to increase L-lysine production in recombinant host cells such as *E. coli*.

G. 1,5-pentanedial

Figure 7:
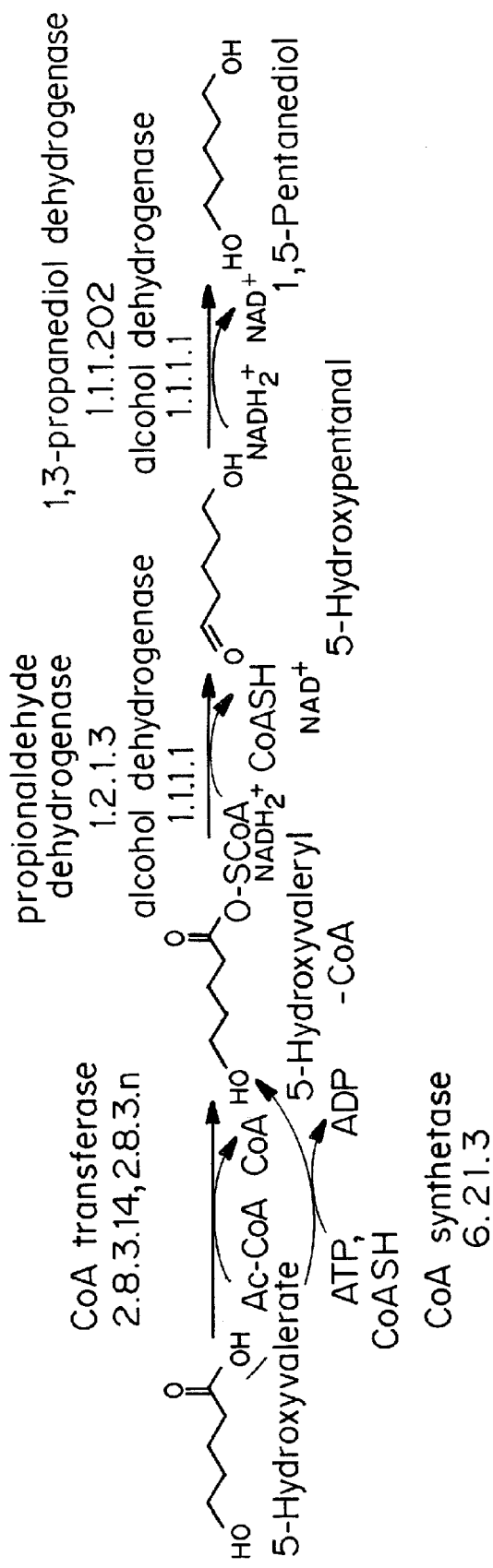
FIG. 7 is a schematic diagram showing biochemical pathways to 1,5 pentanediol.

FIG. 7 provides an overview of the production of 1,5-pentanediol (PDO) from 5HV. 5HV may be converted to 5HV-CoA by a CoA-transferase as described by Huisman et al. (U.S. Pat. No. 7,229,804), Söhling and Gottschalk (J. Bacteriol. 178:871-880 (1996)), and Eikmanns and Buckel (Biol. Chem. Hoppe-Seyler 371:1077-1082 (1990)), or by a CoA-synthetase as described by van Beilen et al. (Molec. Microbiol. 6:3121-3136 (1992)). 5HV may be converted to 5-hydroxypentenal by a propionaldehyde dehydrogenase or alcohol dehydrogenase such as pduP from *Salmonella typhimurium* (Leal, Arch. Microbiol. 180:353-361 (2003)) or eutE from *E. coli* (Skraly, WO Patent No. 2004/024876). 5-Hydroxypentenal may be converted to PDO by 1,3-propanediol dehydrogenase or alcohol dehydrogenase such as dhaT from *Klebsiella pneumoniae* (Tong et al., Appl. Environ. Microbiol. 57(12):3541-3546 (1991)).

H. 5-hydroxyvalerate-co-3-hydroxypropionate

A copolymer containing 5-hydroxyvalerate-co-hydroxyproprionate can be produced from 5HV. *E. coli* K12 strains that were either fadE (repressed fatty acid degradation (FAD)) or fadR⁻ (constitutive FAD) are transfected with nucleic acids expressing polyhydroxyalkanoate and 5-hydroxyvalerate CoA transferase. Preferred *E. coli* strains include MG1655 and LS5218 (Sprat et al., J. Bacteria 146(3):1166-1169 (1981)). As shown in Table 6, GC-FID analysis indicated that LS5218 [pMS93] produced 6.4% dcw PHA, with a polymer composition of 52% 5HV and 48% 3HP. MG1655 [pMS93], on the other hand, made 63.1% dcw PHA that consisted only of 51-1V. Furthermore, GC-MS analysis of LS5218 [pMS93] confirmed the presence of 3HP in the polymer sample. Thus, the active FAD system in LS5218 is able to synthesize 3HP from Na5HV.

III. Production of Transgenic Organisms for Producing Polyhydroxyalkanoates and 5 Carbon Chemicals Transgenic organisms for producing polyhydroxyalkanoates and 5 carbon chemicals are produced using conventional techniques known in the art.

A. Genes for Producing Transgenic P(5HV) Producers

The genes cloned and/or assessed for host strains producing 5HV-containing PHA and 5-carbon chemicals are presented below in Table 1A, along with the appropriate Enzyme Commission number (EC number) and references. As discussed further below, some genes were synthesized for codon optimization while others were cloned via PCR from the genomic DNA of the native or wild-type organism.

TABLE 1A

Genes in microbial host strains producing 5HV-containing PHA and 5-carbon chemicals.

Figure 1:
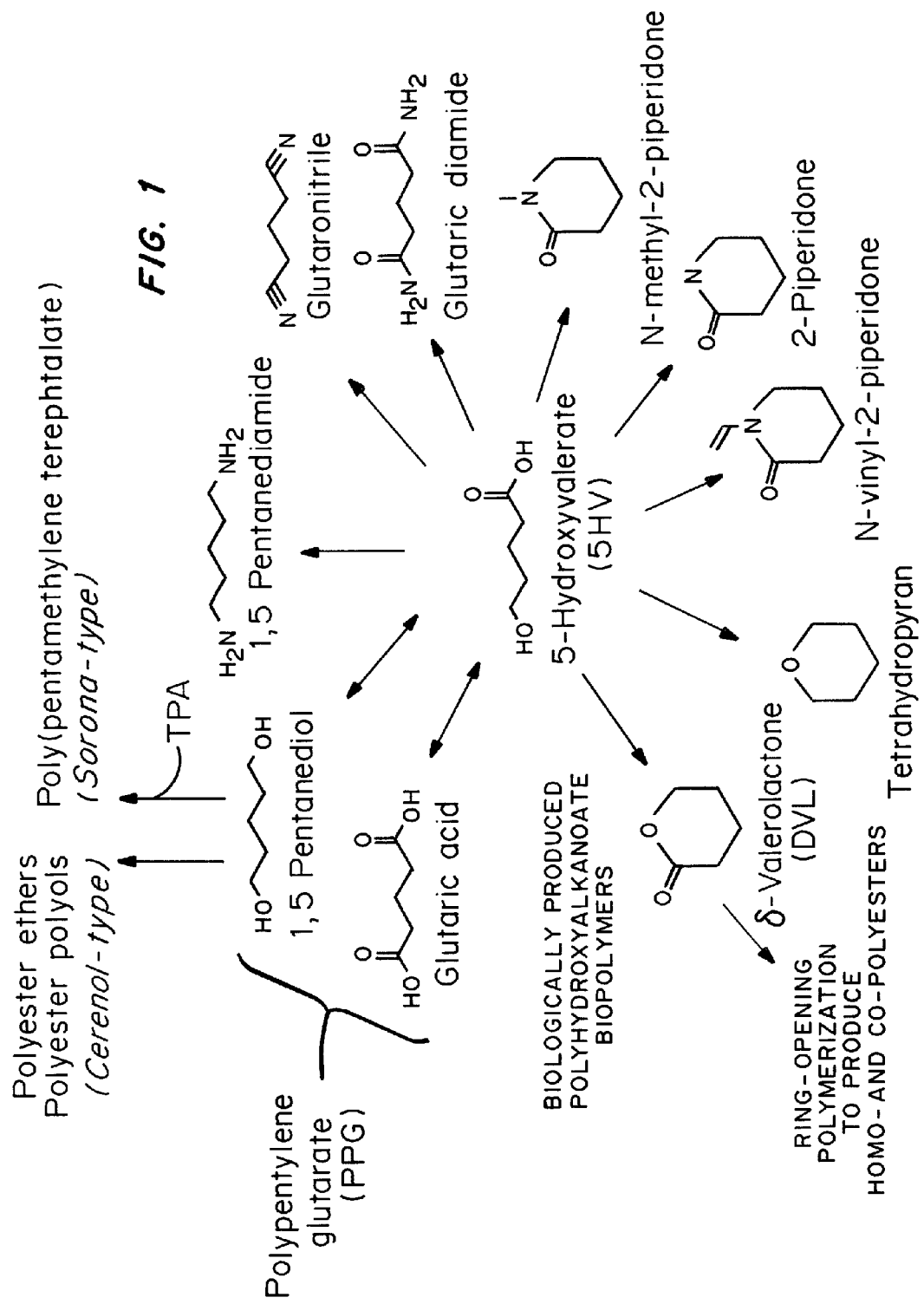

| Reaction number (FIG. 1B) | Gene Name | Enzyme Name | EC Number | Protein Accession No. |
|---|---|---|---|---|
| 1 | davB | lysine 2-monooxygenase | 1.13.12.2 | BAG54787 |
| 2 | davA | 5-aminopentanamidase | 3.5.1.30 | BAG54788 |
| 3 | davT | 5-aminopentanoate transaminase | 2.6.1.48 | AAK97868 |
| 3 | gabT | 4-aminobutyrate transaminase | 2.6.1.19 | NP_417148 |
| 4 | gsaR$_{At2}$ | glutarate semialdehyde reductase | 1.1.1.61 | Gene/Protein ID 1; XP_001210625 |
| 4 | gsaR$_{At}$ | glutarate semialdehyde reductase | 1.1.1.61 | Gene/Protein ID 2; AAK94781 |
| 5 | orfZ | CoA-transferase | 2.8.3.n | AAA92344 |
| 5 |  | 5-hydroxypentanoate CoA-transferase | 2.8.3.14 |  |
| 6 | alkK | acyl-CoA synthetase | 6.2.1.3 | Q00594 |
| 7 | phaC | polyhydroxyalkanoate synthase | 2.3.1.n | YP_725940 |

TABLE 1A-continued

Genes in microbial host strains producing 5HV-containing PHA and 5-carbon chemicals.

| Reaction number (FIG. 1B) | Gene Name | Enzyme Name | EC Number | Protein Accession No. |
|---|---|---|---|---|
| 7 | phaC3/C5 | polyhydroxyalkanoate synthase fusion protein | 2.3.1.n | Gene/Protein ID 3 |
| 7 | phaEC | polyhydroxyalkanoate synthase | 2.3.1.n | Gene/Protein ID 4 and 5 |
| 8 | bktB (phaA) | β-ketoacyl-CoA thiolase | 2.3.1.9 | CAJ92573 |
| 9 | phaB | acetoacetyl-CoA reductase | 1.1.1.36 | AAD05259 |
| 10 | davD | glutarate-semialdehyde dehydrogenase | 1.2.1.20 | NP_742381 |
| 10 | gabD | succinate-semialdehyde dehydrogenase, NADP+-dependent | 1.2.120 | NP_417147 |
| 10 | yneI | succinate-semialdehyde dehydrogenase, NAD+-dependent | 1.2.1.20 | NP_416042 |
|  | pduP | CoA-dependent propionaldehyde dehydrogenase | 1.2.1.3 | NP_460996 |
|  | eutE | predicted aldehyde dehydrogenase in ethanolamine utilization | 1.2.1.3 | NP_416950 |
|  | dhaT | 1,3-propanediol dehydrogenase | 1.1.1.202 | YP_002236499 |
|  | eutG | predicted alcohol dehydrogenase, ethanolamine utilization protein | 1.1.1.202 | AP_003038 |
|  | argO (yggA) | arginine export protein |  | NP_417398 |
|  | lysE | lysine efflux permease |  | NP_600485 |
|  | lysP | LysP lysine APC transporter |  | NP_416661 |
|  | cadA | lysine decarboxylase 1 | 4.1.1.18 | AAC77092 |
|  | ldcC | lysine decarboxylase 2 | 4.1.1.18 | AAC73297 |
|  | yjeK | lysine 2,3-aminomutase | 5.4.3.— | AAC77106 |

Other proteins capable of catalyzing the reactions listed in Table 1A can be discovered by consulting the scientific literature, patents or by BLAST searches against e.g. nucleotide or protein database at NCBI (www.ncbi.nlm.nih.gov/). Synthetic genes can then be created to provide an easy path from sequence databases to physical DNA. Such synthetic genes are designed and fabricated from the ground up, using codons to enhance heterologous protein expression, optimizing characteristics needed for the expression system and host. Companies such as e.g. DNA 2.0 (Menlo Park, Calif. 94025, USA) will provide such routine service. Proteins that may catalyze the biochemical reactions listed in Table 1A are provided in Tables 1B-1AA.

TABLE 1B

Suitable homologues for the DavB protein (lysine 2-monooxygenase, from *Pseudomonas putida* KT2440, EC No. 1.13.12.2, which acts on L-lysine to produce 5-aminopentanamide; protein acc. no. BAG54787 (Revelles et al., J Bacteriol. 187: 7500-10 (2005))).

| Protein Name | Protein Accession No. |
|---|---|
| amine oxidase | YP_001265764 |
| amine oxidase | YP_001666658 |
| amine oxidase | YP_001751665 |
| amino oxidase | YP_606177 |
| amine oxidase, flavin-containing | YP_262728 |

TABLE 1B-continued

Suitable homologues for the DavB protein (lysine 2-monooxygenase, from *Pseudomonas putida* KT2440, EC No. 1.13.12.2, which acts on L-lysine to produce 5-aminopentanamide; protein acc. no. BAG54787 (Revelles et al., J Bacteriol. 187: 7500-10 (2005))).

| Protein Name | Protein Accession No. |
|---|---|
| tryptophan 2-monooxygenase | YP_350882 |
| tryptophan 2-monooxygenase | ZP_04590895 |
| tryptophan 2-monooxygenase | NP_790366 |
| tryptophan 2-monooxygenase | ZP_02189967 |

TABLE 1C

Suitable homologues for the DavA protein (5-aminopentanamidase, from *Pseudomonas putida* KT2440, EC No. 3.5.1.30, which acts on 5-aminopentanamide to produce 5-aminopentanoate, protein acc. no. BAG54788 (Revelles et al., J Bacteriol. 187: 7500-10 (2005))).

| Protein Name | Protein Accession No. |
|---|---|
| Nitrilase/cyanide hydratase and apolipoprotein N-acyltransferase | YP_001265763 |

TABLE 1C-continued

Suitable homologues for the DavA protein (5-aminopentanamidase, from *Pseudomonas putida* KT2440, EC No. 3.5.1.30, which acts on 5-aminopentanamide to produce 5-aminopentanoate, protein acc. no. BAG54788 (Revelles et al., J Bacteriol. 187: 7500-10 (2005))).

| Protein Name | Protein Accession No. |
| --- | --- |
| Nitrilase/cyanide hydratase and apolipoprotein N-acyltransferase | YP_001666657 |
| Nitrilase/cyanide hydratase and apolipoprotein N-acyltransferase | YP_001751666 |
| amidohydrolase | YP_606176 |
| carbon-nitrogen family hydrolase | NP_790365 |
| carbon-nitrogen family hydrolase | ZP_04590894 |
| putative hydrolase | YP_002875091 |
| Nitrilase/cyanide hydratase and apolipoprotein N-acyltransferase | YP_350883 |
| nitrilase | YP_703491 |

TABLE 1D

Suitable homologues for the DavT protein (5-aminopentanoate transaminase, from *Pseudomonas putida* KT2440, EC No. 2.6.1.48, which acts on 5-aminopentanoate to produce glutarate semialdehyde; Protein acc. no. AAK97868 (Espinosa-Urgel and Ramos, Appl. Environ. Microbiol. 67 (11), 5219-5224 (2001))).

| Protein Name | Protein Accession No. |
| --- | --- |
| 4-aminobutyrate aminotransferase | YP_788435 |
| 4-aminobutyrate aminotransferase | YP_002294190 |
| 4-aminobutyrate aminotransferase | YP_345921 |
| 4-aminobutyrate transaminase | YP_002801747 |
| 4-aminobutyrate aminotransferase | YP_001333938 |
| 4-aminobutyrate aminotransferase | NP_790151 |
| 4-aminobutyrate aminotransferase, PLP-dependent | NP_417148 |
| 4-aminobutyrate aminotransferase | YP_311652 |
| 4-aminobutyrate aminotransferase | YP_257332 |

TABLE 1E

Suitable homologues for the GabT protein (4-aminobutyrate transaminase, from *Escherichia coli* str. K-12 substr. MG1655, EC No. 2.6.1.48 (or EC No. 2.6.1.19), which acts on 5-aminopentanoate (or 4 aminobutyrate) to produce glutarate semialdehyde (succinic semialdehyde); Protein Acc. No. NP_417148 (Riley et al., Nucleic Acids Res. 34 (1), 1-9 (2006))).

| Protein Name | Protein Accession No. |
| --- | --- |
| 4-aminobutyrate aminotransferase | ZP_05433421 |
| 4-aminobutyrate aminotransferase | YP_002381614 |

TABLE 1E-continued

Suitable homologues for the GabT protein (4-aminobutyrate transaminase, from *Escherichia coli* str. K-12 substr. MG1655, EC No. 2.6.1.48 (or EC No. 2.6.1.19), which acts on 5-aminopentanoate (or 4 aminobutyrate) to produce glutarate semialdehyde (succinic semialdehyde); Protein Acc. No. NP_417148 (Riley et al., Nucleic Acids Res. 34 (1), 1-9 (2006))).

| Protein Name | Protein Accession No. |
| --- | --- |
| hypothetical protein CIT292_04138 | ZP_03838094 |
| 4-aminobutyrate aminotransferase | YP_001333938 |
| 4-aminobutyrate aminotransferase | NP_461718 |
| 4-aminobutyrate aminotransferase | NP_248957 |
| 4-aminobutyrate aminotransferase | YP_964435 |
| 4-aminobutyrate aminotransferase | YP_982853 |
| 4-aminobutyrate aminotransferase | YP_583770 |

TABLE 1F

Suitable homologues for the GsaR$_{At2}$ protein (glutarate semialdehyde reductase, from *Aspergillus terreus* NIH2624, EC No. 1.1.1.61, which acts on glutarate semialdehyde (or succinic semialdehyde) to produce 5-hydroxyvalerate (or 4-hydroxybutyrate); Protein acc. no. XP_001210625 (Birren, The Broad Institute Genome Sequencing Platform, direct submission to NCBI))).

| Protein Name | Protein Accession No. |
| --- | --- |
| aflatoxin B1-aldehyde reductase GliO-like, putative | CBF89011 |
| aflatoxin B1-aldehyde reductase GliO-like | XP_752707 |
| aflatoxin B1-aldehyde reductase, putative | |
| aflatoxin B1-aldehyde reductase GliO-like, putative | XP_001264422 |
| aflatoxin B1 aldehyde reductase | XP_002375825 |
| hypothetical protein An08g06440 | EEH21318 |
| aflatoxin B1 aldehyde reductase member, putative | |
| | XP_001392759 |
| | EER27170 |
| Chain A, Mouse Succinic Semialdehyde Reductase, Akr7a5 | 2C91_A |
| Chain A, Structure Of The Aflatoxin Aldehyde Reductase In Complex with NADPH | 2BP1_A |

TABLE 1G

Suitable homologues for the GsaR$_{At}$ protein (glutarate semialdehyde reductase, from *Arabidopsis thaliana*, EC No. 1.1.1.61, which acts on glutarate semialdehyde (or succinic semialdehyde) to produce 5-hydroxyvalerate (or 4-hydroxybutyrate); Protein acc. no. AAK94781 (Breitkreuz et al., J. Biol. Chem. 278 (42), 41552-41556 (2003))).

| Protein Name | Protein Accession No. |
| --- | --- |
| hypothetical protein isoform 1 | XP_002266252 |

TABLE 1G-continued

Suitable homologues for the GsaR$_{At}$ protein (glutarate semialdehyde reductase, from *Arabidopsis thaliana*, EC No. 1.1.1.61, which acts on glutarate semialdehyde (or succinic semialdehyde) to produce 5-hydroxyvalerate (or 4-hydroxybutyrate); Protein acc. no. AAK94781 (Breitkreuz et al., J. Biol. Chem. 278 (42), 41552-41556 (2003))).

| Protein Name | Protein Accession No. |
| --- | --- |
| predicted protein | XP_002320548 |
| Os02g0562700 | NP_001047154 |
| succinic semialdehyde reductase isofom1 | BAG16485 |
| unknown | ACU22717 |
| hypothetical protein SORBIDRAFT_04g023180 | XP_002452295 |
| NAD-dependent 4-hydroxybutyrate dehydrogenase | AAC41425 |
| 1,3-propanediol dehydrogenase | ZP_00945634 |
| NAD-dependent 4-hydroxybutyrate dehydrogenase | AAA92348 |
| NAD-dependent 4-hydroxybutyrate dehydrogenase | NP_348201 |

TABLE 1H

Suitable homologues for the OrfZ protein (CoA-transferase, from *Clostridium kluyveri* DSM 555, EC No. 2.8.3.n, which acts on 5-hydroxyvalerate to produce 5-hydroxyvaleryl-CoA; protein acc. no. AAA92344 (Huisman et al., U.S. Pat. No. 7,229,804; Söhling and Gottschalk, J. Bacteriol. 178: 871-880 (1996))).

| Protein Name | Protein Accession No. |
| --- | --- |
| acetyl-CoA hydrotase/transferase | ZP_05395303 |
| acetyl-CoA hydrolase/transferase | YP_001309226 |
| 4-hydroxybutyrate coenzyme A transferase | ZP_05618453 |
| 4-Hydroxybutyrate CoA-transferase | CAB60036 |
| 4-hydroxybutyrate CoA-transferase | NP_904965 |
| 4-hydroxybutyrate CoA-transferase | ZP_05427217 |
| acetyl-CoA hydrolase/transferase | YP_002430388 |
| acetyl-CoA hydrolase/transferase | YP_001433830 |
| acetyl-CoA hydrolase/transferase | YP_002509648 |

TABLE 1I

Suitable homologues for AlkK protein (Acyl-CoA synthetase, from *Pseudomonas oleovorans*; EC No. 6.2.1.3, which acts on 5-hydroxyvalerate to produce 5-hydroxyvaleryl-CoA; protein acc. no. Q00594 (van Beilen et al., Mol. Microbiol. 6 (21), 3121-3136 (1992))).

| Protein Name | Protein Accession No. |
| --- | --- |
| AMP-dependent synthetase and ligase | YP_001185941 |
| medium-chain acyl-CoA synthetase | ABO21016 |
| acyl-CoA synthetase | CAB69080 |
| medium-chain acyl-CoA synthetase | ZP_06063626 |
| acyl-CoA synthetase | YP_523641 |
| AMP-dependent synthetase and ligase | ZP_03542412 |
| acyl-CoA synthetase | YP_726019 |
| medium-chain-fatty-acid-CoA ligase | ZP_06016304 |
| medium-chain-fatty-acid--CoA ligase | ZP_02145453 |

TABLE 1J

Suitable homologues for the PhaC protein (polyhydroxyalkanoate synthase, from *Ralstonia eutropha*, EC No. 2.3.1.n, which acts on (R)-3-hydroxybutyryl-CoA + [(R)-3-hydroxybutanoate]n to produce [(R)-3-hydroxybutanoate](n + 1) + CoA; Protein acc. no. YP_725940 (Peoples and Sinskey, J. Biol. Chem. 264: 15298-15303 (1989))).

| Protein Name | Protein Accession No. |
| --- | --- |
| polyhydroxyalkanoic acid synthase | YP_002005374 |
| PHB synthase | BAB96552 |
| PhaC | AAF23364 |
| Polyhydroxyalkanoate synthase protein PhaC | AAC83658 |
| polyhydroxybutyrate synthase | AAL17611 |
| poly(R)-hydroxyalkanoic acid synthase, class I | YP_002890098 |
| poly-beta-hydroxybutyrate polymerase | YP_159697 |
| PHB synthase | CAC41638 |
| PHB synthase | YP_001100197 |

TABLE 1K

Suitable homologues for the PhaE protein (PhaE subunit of PhaEC PHA synthase, from *Thiocapsa pfenigii*, which acts on (R)-3-hydroxybutyryl-CoA + [(R)-3-hydroxybutanoate]n to produce [(R)-3-hydroxybutanoate](n + 1) + CoA).

| Protein Name | Protein Accession No. |
| --- | --- |
| orf2 5' to phbC | AAC60429 |
| Uncharacterized 40.5 kDa protein in phbC-phbA intergenic region | P45372 |
| hypothetical protein 2 | S29275 |
| Uncharacterized 41.3 kDa protein in phbC-phbA intergenic region | P45367 |
| poly(R)-hydroxyalkanoic acid synthase, class III, PhaE subunit | ZP_04775558 |
| hypothetical protein Tgr7_1513 | YP_002513584 |
| PHA synthase subunit PhaE | AAG30260 |

TABLE 1K-continued

Suitable homologues for the PhaE protein (PhaE subunit of PhaEC PHA synthase, from *Thiocapsa pfenigii*, which acts on (R)-3-hydroxybutyryl-CoA + [(R)-3-hydroxybutanoate]n to produce [(R)-3-hydroxybutanoate](n + 1) + CoA).

| Protein Name | Protein Accession No. |
|---|---|
| poly(R)-hydroxyalkanoic acid synthase, class III, PhaE subunit | YP_865086 |
| PHA synthase | BAE20054 |
| PHA synthase subunit E | ABK60192 |

TABLE 1L

Suitable homologues for the PhaC protein (PhaC subunit of PhaEC PHA synthase, from *Thiocapsa pfenigii*, which acts on (R)-3-hydroxybutyryl-CoA + [(R)-3-hydroxybutanoate]n to produce [(R)-3-hydroxybutanoate](n + 1) + CoA).

| Protein Name | Protein Accession No. |
|---|---|
| poly(R)-hydroxyalkanoic acid synthase, class III, PhaC subunit | ZP_04774202 |
| Poly-beta-hydroxybutyrate polymerase | P45366 |
| PHA synthase subunit PhaC | AAG30259 |
| poly(R)-hydroxyalkanoic acid synthase, class III, PhaC subunit | YP_865087 |
| poly (3-hydroxybutyric acid) synthase | YP_200860 |
| poly(3-hydroxyalkanoate) synthase PhaC | YP_001660017 |
| PhaC | AAL76316 |
| poly(3-hydroxyalkanoate) synthase | NP_440750 |
| poly(R)-hydroxyalkanoic acid synthase, class III, PhaC subunit | YP_003151887 |
| poly(R)-hydroxyalkanoic acid synthase, class III, PhaC subunit | YP_001374365 |

TABLE 1M

Suitable homologues for the BktB (PhaA) protein (β-ketoacyl-CoA thiolase, from *Ralstonia eutropha* H16, EC No. 2.3.1.9, which acts on acetyl-CoA to produce acetoacetyl-CoA; Protein acc. no. CAJ92573 (Peoples & Sinskey, J Biol Chem. 1989 Sep 15; 264(26): 15293-7. Pohlmann et al., Nature Biotech 24 (10), 1257-1262 (2006))).

| Protein Name | Protein Accession No. |
|---|---|
| acetyl-CoA acetyltransferase | YP_002005375 |
| acetyl-CoA acetyltransferase | YP_558680 |
| acetyl-CoA acetyltransferase | BAB96553 |
| acetyl-CoA acetyltransferase | YP_001021062 |
| beta-ketothiolase | BAA33156 |
| acetyl-CoA acetyltransferase | YP_523809 |
| acetyl-CoA acetyltransferase | NP_250691 |
| beta-ketothiolase | YP_002802211 |
| acetyl-CoA acetyltransferase | YP_001919890 |

TABLE 1N

Suitable homologues for the PhaB protein (acetoacetyl-CoA reductase, from *Bacillus megaterium*, EC. No. 1.1.1.36, which acts on acetoacetyl-CoA to produce (R)-3-hydroxybutyryl-CoA; Protein acc. no. AAD05259 (McCool & Cannon, J. Bacteriol. 183 (14), 4235-4243 (2001))).

| Protein Name | Protein Accession No. |
|---|---|
| acetoacetyl-CoA reductase | NP_831099 |
| 3-ketoacyl-(acyl-carrier-protein) reductase | YP_645133 |
| 3-ketoacyl-(acyl-carrier-protein) reductase | ZP_01126888 |
| hypothetical protein DSY2660 | YP_518893 |
| 3-ketoacyl-(acyl-carrier-protein) reductase | YP_001865860 |
| 3-ketoacyl-(acyl-carrier-protein) reductase | YP_001658404 |
| 3-oxoacyl-(acyl-carrier-protein) reductase | YP_002949207 |
| 3-oxoacyl-(acyl-carrier protein) reductase | NP_371755 |
| 3-ketoacyl-(acyl-carrier-protein) reductase | YP_001385912 |

TABLE 1O

Suitable homologues for the DavD protein (glutarate-semialdehyde dehydrogenase, from *Pseudomonas putida* KT2440, EC No. 1.2.1.20, which acts on glutarate semialdehyde to produce glutarate; Protein acc. no. NP_742381 (Espinosa-Urgel and Ramos, Appl. Environ. Microbiol. 67 (11), 5219-5224 (2001))).

| Protein Name | Protein Accession No. |
|---|---|
| succinate-semialdehyde dehydrogenase I | YP_605978 |
| succinate-semialdehyde dehydrogenase I | YP_345920 |
| succinate-semialdehyde dehydrogenase I, NADP-dependent | NP_417147 |

TABLE 1O-continued

Suitable homologues for the DavD protein (glutarate-semialdehyde dehydrogenase, from *Pseudomonas putida* KT2440, EC No. 1.2.1.20, which acts on glutarate semialdehyde to produce glutarate; Protein acc. no. NP_742381 (Espinosa-Urgel and Ramos, Appl. Environ. Microbiol. 67 (11), 5219-5224 (2001))).

| Protein Name | Protein Accession No. |
| --- | --- |
| predicted aldehyde dehydrogenase | NP_416042 |
| succinate-semialdehyde dehydrogenase I | NP_461717 |
| Aldehyde dehydrogenase | YP_002801982 |
| succinic semialdehyde dehydrogenase | YP_002827846 |
| succinic semialdehyde dehydrogenase | YP_001228901 |
| succinate-semialdehyde dehydrogenase (NADP+) | YP_841054 |

TABLE 1P

Suitable homologues for the GabD protein (succinate semialdehyde dehydrogenase, NADP+-dependent, from *Escherichia coli* str. K-12 substr. MG1655, EC No. 1.2.1.20, which acts on glutarate semialdehyde (or succinic semialdehyde) to produce glutarate (or succinate); Protein acc. no. NP_417147 (Riley et al., Nucleic Acids Res. 34 (1), 1-9 (2006))).

| Protein Name | Protein Accession No. |
| --- | --- |
| succinate-semialdehyde dehydrogenase I | ZP_05433422 |
| succinate-semialdehyde dehydrogenase (NAD(P)(+)) | YP_001744810 |
| hypothetical protein CIT292_04137 | ZP_03838093 |
| succinate-semialdehyde dehydrogenase | YP_002638371 |
| succinate-semialdehyde dehydrogenase I | YP_001333939 |
| succinate-semialdehyde dehydrogenase I | NP_742381 |
| succinate-semialdehyde dehydrogenase [NADP+] (ssdh) | YP_002932123 |
| succinic semialdehyde dehydrogenase | YP_001951927 |
| succinate semialdehyde dehydrogenase | YP_298405 |

TABLE 1Q

Suitable homologues for the YneI (Sad) protein (succinate semialdehyde dehydrogenase, NAD+-dependent, from *Escherichia coli* str. K-12 substr. MG1655, EC No. 1.2.1.24, which acts on glutarate semialdehyde (succinic semialdehyde) to produce glutarate (succinate); Protein acc. no. NP_416042 (Fuhrer et al., J Bacteriol. 2007 Nov; 189(22): 8073-8. Dennis and Valentin, U.S. Pat. No. 6,117,658))).

| Protein Name | Protein Accession No. |
| --- | --- |
| succinate semialdehyde dehydrogenase | NP_805238 |
| putative aldehyde dehydrogenase | YP_002919404 |
| aldehyde dehydrogenase | NP_745295 |
| aldehyde dehydrogenase | ZP_03269266 |
| aldehyde dehydrogenase | ZP_05726943 |
| aldehyde dehydrogenase | YP_001906721 |
| hypothetical protein | BAF01627 |
| aldehyde dehydrogenase | ZP_03739186 |
| succinate-semialdehyde dehydrogenase | NP_637690 |

TABLE 1R

Suitable homologues for the PduP protein (CoA-dependent propionaldehyde dehydrogenase, from *Salmonella typhimurium* LT2, EC No. 1.2.1,3, which acts on 5-Hydroxyvaleryl-CoA to produce 5-Hydroxypentanal; Protein acc. no. NP_460996 (Leal et al., Arch. Microbiol. 180: 353-361 (2003), McClelland et al., Nature 413: 852-856 (2001))).

| Protein Name | Protein Accession No. |
| --- | --- |
| ethanolamine utilization protein EutE | YP_002216136 |
| PduP | ZP_04562531 |
| propanediol utilization protein | YP_002236771 |
| ethanolamine utilization protein EutE | NP_756394 |
| aldehyde dehydrogenase | YP_961823 |
| possible aldehyde dehydrogenase | ZP_04969437 |
| Ethanolamine utilization protein eutE | ZP_04637794 |
| Aldehyde Dehydrogenase | ZP_05373182 |
| ethanolamine utilization protein EutE | YP_002350444 |

TABLE 1S

Suitable homologues for the EutE protein (predicted aldehyde dehydrogenase, ethanolamine utilization protein, from *Escherichia coli* str. K-12 substr. MG1655, EC No. 1.2.1.3, which acts on 5-hydroxyvaleryl-CoAtp produce 5-hydroxypentanal, protein acc. no. NP_416950 (Riley et al., Nucleic Acids Res. 34 (1), 1-9 (2006))).

| Protein Name | Protein Accession No. |
| --- | --- |
| hypothetical protein SPAB_00490 | YP_001586756 |
| ethanolamine utilization protein | YP_001336429 |
| probable ethanolamine utilization protein (EutE) | ZP_01222600 |
| putative aldehyde dehydrogenase | ZP_03337600 |

TABLE 1S-continued

Suitable homologues for the EutE protein (predicted aldehyde dehydrogenase, ethanolamine utilization protein, from *Escherichia coli* str. K-12 substr. MG1655, EC No. 1.2.1.3, which acts on 5-hydroxyvaleryl-CoAtp produce 5-hydroxypentanal, protein acc. no. NP_416950 (Riley et al., Nucleic Acids Res. 34 (1), 1-9 (2006))).

| Protein Name | Protein Accession No. |
| --- | --- |
| ethanolamine utilization protein eutE | ZP_04573939 |
| CoA-dependent propionaldehyde dehydrogenase | ZP_00232619 |
| Aldehyde Dehydrogenase | YP_003261430 |
| EutE | YP_311399 |
| hypothetical protein CKO_00340 | YP_001451939 |
| ethanolamine utilization protein (EutE) | YP_066775 |

TABLE 1T

Suitable homologues for the DhaT protein (1,3-propanediol dehydrogenase, from *Klebsiella pneumoniae* 342, EC No. 1.1.1.202, which acts on 5-hydroxypentanal to produce 1,5-pentanediol; Protein acc. no. YP_002236499 (Fouts et al., PLoS Genet. 4 (7), E1000141 (2008))).

| Protein Name | Protein Accession No. |
| --- | --- |
| 1,3-propanediol dehydrogenase | ABD74004 |
| 1,3-propanediol dehydrogenase | YP_698334 |
| alcohol dehydrogenase | YP_001211060 |
| 1,3-propanediol dehydrogenase | YP_796272 |
| iron-containing alcohol dehydrogenase | YP_003192340 |
| conserved hypothetical protein | ZP_06063679 |
| hypothetical protein BB14905_12250 | ZP_01723545 |
| EutG protein | ZP_02497862 |
| 1,3-propanediol dehydrogenase | AAX12915 |
| 1,3-propanediol dehydrogenase | AAM54730 |

TABLE 1U

Suitable homologues for the EutG protein (predicted alcohol dehydrogenase in ethanolamine utilization, from *Escherichia coli* str. K-12 substr. W3110, EC. No. 1.1.1.202, which acts on 5-hydroxypentanalto produce 1,5-pentanediol; Protein acc. no. AP_003038 (Riley et al., Nucleic Acids Res. 34 (1), 1-9 (2006))).

| Protein Name | Protein Accession No. |
| --- | --- |
| ethanolamine utilization protein EutG | YP_001881244 |
| hypothetical protein CKO_00342 | YP_001451941 |
| hypothetical protein SPAB_00492 | YP_001586758 |
| putative transport protein in ethanolamine utilization | YP_002920649 |
| putative alchohol dehydrogenase | ZP_03365534 |
| Ethanolamine utilization protein eutG | ZP_02156849 |
| Ethanolamine utilization protein eutG | ZP_04637792 |
| eutG | AAA80211 |
| Iron-containing alcohol dehydrogenase | NP_634793 |
| ethanolamine utilization protein EutG | ZP_06015246 |

TABLE 1V

Suitable homologues for the ArgO (YggA) protein (arginine export protein, from *Escherichia coli* str. K-12 substr. MG1655, which acts on L-lysine (cytoplasm) and produces L-lysine (outside); Protein acc. no. NP_417398 (Nandineni and Gowrishankar, J. Bacteriol. 186: 3539-3546 (2004))).

| Protein Name | Protein Accession No. |
| --- | --- |
| arginine exporter protein | YP_409404 |
| unnamed protein product | CAA32607 |
| arginine exporter protein | ZP_04560344 |
| arginine exporter protein | NP_461982 |
| arginine exporter protein | YP_001336979 |
| Arginine exporter protein argO | YP_003211829 |
| Arginine exporter protein | YP_002649944 |
| Arginine exporter protein argO | ZP_04613777 |
| arginine exporter protein | NP_930824 |
| arginine exporter protein ArgO | ZP_01988459 |

TABLE 1W

Suitable homologues for the LysE protein (lysine efflux permease, from *Corynebacterium glutamicum* ATCC 13032, which acts on L-lysine (cytoplasm) to produce L-lysine (outside); Protein acc. no. NP_600485 (Tokyo Research Laboratories, Kogyo Co. Ltd., Japan, direct submission to NCBI)).

| Protein Name | Protein Accession No. |
| --- | --- |
| Lysine exporter protein | Q8RQM4 |
| arginine exporter protein ArgO | ZP_04835056 |
| lysine exporter protein | ZP_0393395 |
| lysine exporter protein | ZP_03931790 |
| L-lysine exporter | YP_002958101 |
| lysine exporter protein | ZP_05123881 |
| amino acid transporter LysE | NP_794117 |

TABLE 1W-continued

Suitable homologues for the LysE protein (lysine efflux permease, from *Corynebacterium glutamicum* ATCC 13032, which acts on L-lysine (cytoplasm) to produce L-lysine (outside); Protein acc. no. NP_600485 (Tokyo Research Laboratories, Kogyo Co. Ltd., Japan, direct submission to NCBI)).

| Protein Name | Protein Accession No. |
|---|---|
| arginine exporter protein | ZP_03832031 |
| hypothetical protein ECs3794 | ACI78466 |
| LysE family transporter | NP_353947 |

TABLE 1X

Suitable homologues for the LysP protein (LysP lysine APC transporter, from *Escherichia coli* str. K-12 substr. MG1655, which acts on L-lysine (outside) and produces L-lysine (cytoplasm); Protein acc. no. NP_416661 (Steffes et al., J Bacteriol 174(10): 3242-9 (1992))).

| Protein Name | Protein Accession No. |
|---|---|
| lysine transporter | YP_002383360 |
| hypothetical protein CIT292_03450 | ZP_03837490 |
| lysine transporter | YP_001336242 |
| Lysine-specific permease | YP_003211189 |
| lysine transporter | ZP_03383884 |
| lysine transporter | NP_930088 |
| Lysine-specific permease | ZP_04623004 |
| amino acid permease-associated region | YP_001565334 |
| lysine-specific permease; amino acid-polyamine-organocation (APC) superfamily | YP_002008821 |
| amino acid permease-associated region | YP_776515 |

TABLE 1Y

Suitable homologues for the CadA protein (lysine decarboxylase 1, from *Escherichia coli* str. K-12 substr. W3110, which acts on Lysine to produce Cadaverine; Protein acc. no. AP_004633 (Riley et al., Nucleic Acids Res. 34 (1), 1-9 (2006))).

| Protein Name | Protein Accession No. |
|---|---|
| Lysine decarboxylase | ZP_06166000 |
| hypothetical protein SARI_00317 | YP_001569398 |
| Orn/Lys/Arg decarboxylase family, putative | YP_002932309 |
| Arginine/lysine/ornithine decarboxylase | ZP_06179259 |
| lysine decarboxylase 1 | YP_205440 |
| Lysine decarboxylase | ZP_04636370 |
| lysine decarboxylase 2 | ZP_04559973 |
| lysine decarboxylase 2, constitutive | YP_002396273 |
| Lysine decarboxylase | ZP_04617787 |
| lysine decarboxylase, constitutive | YP_855733 |

TABLE 1Z

Suitable homologues for the LdcC protein (lysine decarboxylase 2, from *Escherichia coli* str. K-12 sub str. MG1655, which acts on Lysine to produce Cadaverine; Protein acc. no. NP_414728 (Riley et al., Nucleic Acids Res. 34 (1), 1-9 (2006))).

| Protein Name | Protein Accession No. |
|---|---|
| lysine decarboxylase 2 | NP_706131 |
| hypothetical protein CKO_03180 | YP_001454701 |
| lysine decarboxylase, constitutive | ZP_02686615 |
| lysine decarboxylase, constitutive | YP_002240326 |
| Lysine decarboxylase, constitutive | YP_003209178 |
| Lysine decarboxylase | YP_002647915 |
| Lysine decarboxylase | ZP_04621086 |
| lysine decarboxylase 1 | YP_003294813 |
| lysine decarboxylase 1 | YP_859739 |
| Orn/Lys/Arg decarboxylase family, putative | YP_002931768 |

TABLE 1AA

Suitable homologues for the YjeK protein (lysine 2,3-aminomutase, from *Escherichia coli* str. K-12 sub str. MG1655, which acts on L-lysine to produce (R)-b-Lysine; Protein acc. no. NP_418570 (Riley et al., Nucleic Acids Res. 34 (1), 1-9 (2006))).

| Protein Name | Protein Accession No. |
|---|---|
| hypothetical protein SFV_4304 | YP_691589 |
| putative lysine aminomutase | YP_002385208 |
| conserved hypothetical protein | ZP_04559561 |
| KamA family protein | YP_002240896 |
| putative aminomutase | NP_463197 |
| hypothetical protein ESA_00156 | YP_001436296 |
| lysine 2,3-aminomutase YodO family protein | YP_003019317 |
| hypothetical protein ETAE_0333 | YP_003294390 |
| Uncharacterized kamA family protein yjeK | ZP_04617468 |
| lysine 2,3-aminomutase | YP_002157135 |

One embodiment provides a transgenic or recombinant organism for producing P(5HV) or other PHAs containing 5HV monomers. The organism can be prokaryotic or eukaryotic. Suitable prokaryotes include but are not limited to bacteria, for example *E. coli*.

B. Methods and Materials for Producing Recombinant Organisms or Cells

1. Organisms or Cells to be Modified

Organisms or cells that can be modified for producing 5HV containing PHA biopolymers, 5-aminopentanoate (5AP), 5-hydroxyvalerate (5HV), glutarate, and 1,5-pentanediol (PDO) include eukaryotes and prokaryotes. Suitable prokaryotes include bacteria. A number of bacteria can be genetically engineered to produce polyhydroxyalkanoates. Examples include *E. coli, Alcaligenes latus, Alcaligenese eutrophus, Azotobacter, Pseudomonas putida, Ralstonia eutropha, Sal-* monella, *Klebsiella, Corynebacterium glutamicum, Rhodococcus*, and *Brevibacterium lactofermentum*. Additional prokaryotes include, but are not limited to, eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31.537); (ATCC 27,325) and K5772 (ATCC 53,635).

These include organisms that already produce polyhydroxyalkanoates, modified to utilize alternative substrates or incorporate additional monomers, or to increase production, and organisms that do not produce polyhydroxyalkanoates, but which express none to some of the enzymes required for production of polyhydroxyalkanoates. *R. eutropha* is an example of an organism which produces PHAs naturally. *E. coli* and *C. glutamicum* are examples of organisms where it would be necessary to introduce transgenes which encode the enzymes for PHA production.

For the production of the C5 chemicals 5-aminopentanoate (5AP), 5-hydroxyvalerate (5HV), glutarate, and 1,5-pentanediol where they are not polymerized to 5-hydroxyvalerate containing PHAs but secreted into the growth medium then it is useful to use industrial microorganisms which are used to manufacture lysine. *Corynebacterium glutamicum*, including its subspecies *Brevibacterium flavum, Brevibacterium lactofermentum, Corynebacterium lilium, Corynebacterium efficiens* and *Brevibacterium divaricatum*, which has been used for the industrial production of L-lysine (Microbial. Monogr. 5:39-70 (2007)), is an example of the microorganisms can be developed for the production of glutarate, 1,5-pentandiol, 5-hydroxyvalerate, and other products that can be produced from lysine via lysine degradation pathways described in this invention. Engineered *E. coli* have also been used for lysine production. The procedures to obtain *C. glutamicum* strains for the production of L-lysine such as random mutagenesis and subsequent selection of the mutant that resistant to toxic lysine analogues, like S-(2-aminoethyl) cysteine, and introduction of mutant alleles of the gene targets such as lysC and horn which encode aspartate kinase and homoserine dehydrogenase, respectively, are well-established and has been described (Curr Opin. Microbiol. 9:268-274 (2007)). Aspartate kinase is subject to a feedback inhibition by threonine and lysine, and the release of this enzyme from the feedback inhibition is regarded as one of the key features to develop a lysine producer strains. Another target of engineering for the development of the strains capable to produce chemicals derived from lysine degradation pathways is the lysine exporter such as LysE in *C. glutamicum*. Mutagenesis of lysE gene of L-lysine producing *C. glutamicum* strains will prevent the excretion of lysine from the cytoplasm and thus increase the yield of products via the pathway devised to convert lysine to the products. Methods for constructing *C. glutamicum* strains for the production of PHAs such as PHB are also known in the art (Jo, S-J et. Al, 2006. J. Bioscience and Bioengineering 102: 233-236).

Suitable eukaryotic organisms or cells include fungi such as filamentous fungi or yeast. *Saccharomyces cerevisiae* is a commonly used lower eukaryotic host microorganism.

2. Methods for Generating Transgenic Organisms
   i. Extrachromosal Transfection Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including chemical transformation such as calcium phosphate or calcium chloride co-precipitation, DEAE-dextran-mediated transfection, lipofection, or electroporation. Conventional transformation techniques are described in Sambrook et al., Molecular Cloning: A Laboratory Manual, Third Edition, Cold Spring Harbor Laboratory Press, Cold Spring Harbor, N.Y., 2001. Transformations into yeast are typically carried out according to the method of Van Solingen et al. *J. Bact.,* 130:946 (1977) and Hsiao et al., *Proc. Natl. Acad. Sci. (USA),* 76:3829 (1979).

ii. Chromosomal Integration

Methods for incorporating engineered gene constructs into the chromosomal DNA of gram negative and gram positive bacterial cells are well known to those skilled in the art. Typical integration mechanisms include homologous recombination using linearized DNA in recBC or recD strains followed by P1 transduction (Miller 1992, A Short Course in Bacterial Genetics: A Laboratory Manual & Handbook for *Escherichia coli* and Related Bacteria. Cold Spring Harbor laboratory Press, Cold Spring Harbor, N.Y.) special plasmids (Hamilton et al., *J. Bacteriol.* 171:4617 (1989); Metcalf et al., *Plasmid* 35:1 (1996); U.S. Pat. No. 5,470,727 to Mascarenhas et al.), or by random insertion using transposon based systems (Herrero et al. *J. Bacteriol.* 172:6557 (1990); Peredelchuk & Bennett, Gene 187:231 (1997); U.S. Pat. No. 5,595,889 to Richaud et al.; U.S. Pat. No. 5,102,797 to Tucker et al.). In general, the microbial strains containing an insertion are selected on the basis of an acquired antibiotic resistance gene that is supplied by the integrated construct. However, complementation of auxotrophic mutants can also be used. The same methods can be used to introduce any of the transgenes encoding the various metabolic pathways described herein. Some of these methods are described in more detail below with respect to the pha genes.

Expression of the genes of interest for chromosomal integration can be achieved by including a transcription-activating sequence (promoter) in the DNA construct to be integrated. Site-directed, homologous recombination can be combined with amplification of expression of the genes of interest, as described by U.S. Pat. No. 5,000,000 to Ingram et al.

Chromosomal integration can also be achieved by the methods of Datsenko and Wanner (Proc. Natl. Acad. Sci. USA. 97:6640-6645 (2000)), and as used in Example 7, below.

A series of expression cassettes have been developed for inserting heterologous genes into bacterial chromosomes. These cassettes are based on the transposon delivery systems described by Herrero et al., *J. Bacteriol.* 172:6557-67 (1990); de Lorenzo et al., *J. Bacteriol.* 172:6568 (1990). Although these systems specify RP4-mediated conjugal transfer and use only transposon Tn10 and Tn5, any combination of transposon ends and delivery system could be adapted for the technology described, resulting in sustained and homogeneous PHA production.

The following general approach is used for generating transgenic *E. coli* PHB producers: (1) a promoterless antibiotic resistance (abr) gene is cloned in the polylinker of a suitable plasmid such as pUC18NotI or pUC18SfiI so that the major part of the polylinker is upstream of abr; (2) pha genes, genes encoding a GABA transaminase, a succinic semi-aldehyde reductase, and a 4-hydroxybutyrate-CoA transferase are subsequently cloned upstream of and in the same orientation as the abr gene; (3) the pha-abr cassette is excised as a NotI or AvrII fragment (AvrII recognizes the SfiI site in pUC18SfiI) and cloned in the corresponding sites of any plasmid like those from the pUT- or pLOF-series; (4) the resulting plasmids are maintained in *E. coli* λ pir strains and electroporated or conjugated into the *E. coli* strain of choice in which these plasmids do not replicate; and (5) new strains in which the pha-abr cassette has successfully integrated in the chromosome are selected on selective medium for the host (e.g., naladixic acid when the host is naladixic acid resistant) and for the cassette (e.g., chloramphenicol, kanamycin, tetracyclin, mercury chloride, bialaphos). The resulting pha integrants are screened on minimal medium in the presence of glucose for growth and PHB formation.

Several modifications of this procedure can be made. If the promotorless antibiotic resistance marker is not used, the insertion of the PHA genes is selected based on a marker present in the vector and integrated strains producing the desired level of PHA are detected by screening for PHA production. The pha genes may have, but do not need, endogenous transcription sequences, such as upstream activating sequences, RNA polymerase binding site, and/or operator sequences. If the pha genes do not have such sequences, the described approach is limited to the use of vectors like the pUT series in which transcription can proceed through the insertion sequences. This limitation is due to the inability of RNA polymerase to read through the Tn10 flanking regions of the pLOF plasmids. The abr gene may carry its own expression sequences if so desired. Instead of an abr gene, the construct may be designed such that an essential gene serves as selective marker when the host strain has a mutation in the corresponding wild-type gene. Examples of genes useful for this purpose are generally known in the art. Different constructs can be integrated into one host, either subsequently or simultaneously, as long as both constructs carry different marker genes. Using multiple integration events, pha genes can be integrated separately, e.g., the PHB polymerase gene is integrated first as a phaC-cat cassette, followed by integration of the thiolase and reductase genes as a phaAB-kan cassette. Alternatively, one cassette may contain all pha genes whereas another cassette contains only some pha genes required to produce a desired PHA polymer.

In some cases a transposon integration vector such as pJMS11 (Panke et al. *Appl. Enviro. Microbiol.* 64: 748-751) may be used such that the selectable marker can be excised from the chromosome of the integrated strain. This is useful for a number of reasons including providing a mechanism to insert multiple transposon constructs using the same marker gene by excising the marker following each insertion event.

3. Sources of pha and Other Genes Involved in PHA Formation

A general reference for genes involved on PHA formation is Madison and Huisman, 1999, Microbiology and Molecular Biology Reviews 63: 21-53. The pha genes may be derived from different sources and combined in a single organism, or from the same source.

i. Reductase Encoding Genes

Reductase-encoding genes have been isolated from *A. latus, R. eutropha* (Peoples & Sinskey, *J. Biol. Chem.* 264 (26):15298-303 (1989); *Acinetobacter* sp. (Schembri, et al., *J. Bacteriol.* 177(15):4501-7 (1995)), *C. vinosum* (Liebergesell & Steinbuchel, *Eur. J. Biochem.* 209(1):135-50 (1992)), *P. acidophila, P. denitrificans* (Yabutani, et al., *FEMS Microbial. Lett.* 133 (1-2):85-90 (1995)), *R. meliloti* (Tombolini, et al., *Microbiology* 141:2553-59 (1995)), and *Z. ramigera* (Peoples, et al., *J. Biol. Chem.* 262(1):97-102 (1987)). U.S. Pat. No. 7,229,804 discloses transgenic organisms that produce P4HB using the 4hbD gene that encodes the 4-hydroxybutyrate dehydrogenase from *C. kluyveri* (Sohling and Gottschalk, *J. Bacteriol.* 178, 871 880 (1996)). 4hbD requires NADH. Preferred reductases include, but are not limited to, those that do not require NADH. Exemplary reductases include AKR7A5 from *Mus musculus* (GenInfo Identifier: 27659727)(Hinshelwood, A. et al. *FEBS Letters* 523:213-218 (2002), GHBDH from *Arabidopsis thaliana* (GI:145338934) (Breitkreuz, K. et al. *J. Biol. Chem.* 278:41552-41556, ATEG_00539 from *Aspergillus terreus* (GI:115491994).

ii. CoA Transferase and CoA Synthetase

Suitable CoA transferases (EC 2.8.3.n) include but are not limited to orfZ from *C. kluyveri*. The sequence of orfZ is provided in U.S. Pat. No. 7,229,804 to Huisman et al. and is incorporated by reference in its entirety. Another suitable CoA transferase includes abfT from *C. aminobutyricum* (Gerhardt et al., *Arch Microbiol* 74:189-199 (2000)). Other enzymes that could produce acyl-CoA include CoA synthetases (EC 6.2.1.3). These enzymes use ATP and free CoA to catalyze the covalent addition of CoA to the carboxylic acid and have been described in van Beilen et al. (*Molec Microbial* (1992) 6:3121-3136) and Aquin et al. (WO 02/40690 A2).

iii. PHA Polymerase-Encoding Genes

PHA polymerase-encoding genes have been isolated from *Aeromonas caviae* (Fukui & Doi, *J. Bacteriol.* 179(15):4821-30 (1997)), *A. latus, R. eutropha* (Peoples & Sinskey, *J. Biol. Chem.* 264(26):15298-303 (1989); *Acinetobacter* (Schembri, et al., *J. Bacteriol.* 177(15):4501-7 (1995)), *C. vinosum* (Liebergesell & Steinbuchel, *Eur. J. Biochem.* 209(1):135-50 (1992)), *Methylobacterium extorquens* (Valentin & Steinbuchel, *Appl. Microbiol. Biotechnol.* 39(3):309-17 (1993)), *Nocardia corallina* (GenBank Acc. No. AF019964), *Nocardia salmonicolor, P. acidophila, P. denitrificans* (Ueda, et al., *J. Bacterial.* 178(3):774-79 (1996)), *Pseudomonas aeruginosa* (Timm & Steinbuchel, *Eur. J. Biochem.* 209(1):15-30 (1992)), *Pseudomonas oleovorans* (Huisman, et al., *J. Biol. Chem.* 266:2191-98 (1991)), *Rhizobium etli* (Cevallos, et al., *J. Bacterial.* 178(6):1646-54 (1996)), *R. meliloti* (Tombolini, et al., *Microbiology* 141 (Pt 10):2553-59 (1995)), *Rhodococcus ruber* (Pieper & Steinbuchel, *FEMS Microbiol. Lett.* 96(1):73-80 (1992)), *Rhodospirrilum rubrum* (Hustede, et al., *FEMS Microbiol. Lett* 93:285-90 (1992)), *Rhodobacter sphaeroides* (Steinbuchel, et al., *FEMS Microbial. Rev.* 9(2-4):217-30 (1992); Hustede, et al., *Biotechnol. Lett.* 15:709-14 (1993)), *Synechocystis* sp. (Kaneko, DNA Res. 3(3):109-36 (1996)), *T. violaceae* (Liebergesell & Steinbuchel, *Appl. Microbiol. Biotechnol.* 38(4: 493-501 (1993)), and *Z. ramigera* (GenBank Acc. No. U66242).

Other genes that have not been implicated in PHA formation but which share significant homology with the pha genes and/or the corresponding gene products may be used as well. Genes with significant homology to the phaB gene encoding acetoacetyl CoA reductase have been isolated from several organisms, including *Azospirillum brasiliense* (NCBI Accession Nos. X64772, X52913) *Rhizobium* sp. (NCBI Accession Nos. U53327, Y00604), *E. coli* (NCBI Accession No. D90745), *Vibrio harveyi* (NCBI Accession No. U39441), *H. influenzae* (NCBI Accession No. U32701), *B. subtilis* (NCBI Accession No. U59433), *P. aeruginosa* (NCBI Accession No. U91631), *Synechocystis* sp. (NCBI Accession No. D90907), *H. pylori* (NCBI Accession No. AE000570), *Arabidopsis thaliana* (NCBI Accession No. X64464), *Cuphea lanceolata* (NCBI Accession No. X64566) and *Mycobacterium smegmatis* (NCBI Accession No. U66800).

III. Methods of Producing PHAs Containing 5HV and C5 Chemicals

Methods for producing polyhydroxyalkanoates using renewable carbon sources as feedstock are provided. In a preferred embodiment, bacteria are transformed or transfected with one or more nucleic acid constructs encoding the genes necessary for producing 5-aminopentanoate (5AP), 5-hydroxyvalerate (5HV), glutarate, and 1,5-pentanediol (PDO) and polymers thereof from renewable resources.

IV. Methods of Use

The disclosed transgenic organisms can be used to produce C5 chemicals such as 5-aminopentanoate (5AP), 5-hydroxyvalerate (5HV), glutarate, and 1,5-pentanediol (PDO) as well as PHA biopolymers comprising 5HV monomers. In the case of the production of the C5 chemicals the recombinant organism expressing the appropriate transgenes(s), optionally including having genes encoding competing pathweays inactiviated or deleted are grown on a renewable fermentation substrate. The substrate is selected from carbohydrates, lysine, proline vegetable oils, fatty acids or combinations thereof. A useful combination for some embodiments would be a mixture of glucose and lysine. Another suitable combination would be sucrose and lysine. Preferably the feedstock comprises predominantly one substrate, for example glucose or sucrose. Suitable carbohydrate substrates comprise one or more sugars selected from glucose, fructose, xylose, arabinose, sucrose, lactose and maltose. For the production of C5 chemicals, the recombinant organism is grown on the renewable substrate until the desired end product accumulates in the growth medium at which time the cells are removed by flocculation, settling, centrifugation or filtration and the product is recovery from the cell-free medium by standard procedures. Such procedures are known in the art for the recovery of other fermentation produced acids and diols such as lactic acid, succinic acid, 3-hydroxypropionic acid, 1,3-propanediol and 1,4-butanediol.

The recombinant organisms can be used for the fermentation production of 5HV containing PHA biopolymers including the homopolymer P5HV and 5HV containing PHA copolymers by culturing the organisms in the presence of renewable carbons sources such as glucose, lysine, etc. and other substrates selected to provide a desired polymer or copolymer. The recombinant organsims are grown on the substrates until the PHA polymers have accumulated inside the cells at which point the PHA polymers are extracted from the cells by methods known to those skilled in the art. The 5HV containing PHA polymers obtained from the organisms can be used in a wide range of industrial plastics applications such as for films, fibers, foams, injection molded goods, blow molded bottles, paper coating and the like. They can also be used for biomedical applications including tissue augmentation, to produce heart valves, as sutures, and to produce vascular grafts. Exemplary co-polymers include, but are not limited to, PHB5HV and p(3-hydroxypropionate-co-5-hydroxyvalerate) p(4-hydroxybutyrate-co-5-hydroxyvalerate). The recombinant organisms can be genetically engineered to include additional genes such as beta-ketothiolase and acetoacetyl-CoA reductase as needed for the production of copolymers.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Example 1

Biosynthesis of P(5HV) Homopolymer from Sodium 5-Hydroxyvalerate

As a first demonstration of the ability to synthesize 5HV-containing PHAs, sodium 5-hydroxyvalerate (Na5HV) was fed to *E. coli* strains expressing both a CoA transferase or CoA synthetase and a PHA synthase, in order to determine if the fed 5HV monomer would be accepted and incorporated directly into P(5HV) homopolymer. Na5HV was synthesized via base hydrolysis of δ-valerolactone (DVL). This procedure involved adding 0.1 mol NaOH to 50 mL methanol with stirring until dissolved. To this, 0.1 mol DVL was added with vigorous stirring. The resulting precipitate was dried, dissolved in water, pH-adjusted to 8.5, and filter-sterilized with a 0.2 µM filter. Analysis of the salt solution was performed on a Waters Alliance HPLC in order to confirm that all of the DVL had been saponified.

Different combinations of CoA transferase/synthetase and PHA synthase genes were tested in order to find the best combination suitable for P(5HV) production. The CoA transferases/synthetases tested were *C. kluyveri* orfZ and *P. oleovorans* alkK, and the PHA synthases were *R. eutropha* phaC and *T. pfenigii* phaEC (Table 1A). All strains used in this experiment were derived from MG1655 (Jensen, *J. Bacteria* 175(11):3401-3407 (1993)). Four expression plasmids (pFS92, pMS96, pMS93, and pMS102), each containing different combinations of CoA transferase/synthetase and PHA synthase, were constructed as described in the following paragraphs.

Plasmid Construction

Plasmid pFS30 was constructed by digesting pAET41 (Peoples and Sinskey, *J. Biol. Chem.* 264(26):15298-15303 (1989)) with XmaI and StuI in order to remove a fragment containing *R. eutropha* phaC and its native promoter ($P_{Re}$). Plasmid pAET41 is a pUC18 vector (Accession No. L08752) that contains a chromosomal fragment from *R. eutropha* H16 encompassing the phaC gene. Plasmid pFS16 (Skraly and Peoples, U.S. Pat. No. 6,323,010), which is a derivative of pTrc99a (Pharmacia, Uppsala, Sweden) containing the orfZ gene from *C. kluyveri* (Table 1A) under the $P_{Trc}$ promoter, was digested with BamHI, blunted with T4 polymerase, and digested a second time with XmnI prior to ligation with the $P_{Re}$-phaC XmaI-StuI fragment. The resulting plasmid was designated pFS30, and contained the phaC-orfZ operon fusion under the constitutively-expressed $P_{Re}$ promoter.

Plasmid pFS92 was made in a multi step process. First, *T. pfenigii* phaE was amplified from pMON25893 (Reiser et al., *Appl. Microbiol. Biotechnol.* 53(2):209-218 (2000)) with primers FS-E5' and FS-E3', which contain engineered EcoRI and Acc65I restriction sites. The phaE PCR product was then digested with restriction enzymes EcoRI and Acc65I and ligated to similarly digested pTrcN (Gerngross et al., *Biochemistry* 33:9311-9320 (1994)) to form pFS89. The primer sequence for FS-E5' is (5')-GGAATTCAGGAGGTTTTTAT-GAACGATACGGCCAACAAGACCAGC (SEQ ID NO:1) and the primer sequence for FS-E3' is (5')-GGGGTACCT-CACTGGCCGGTGGTGGGCTTGGTGGTCTTGCGGCG (SEQ ID NO:2). Next, *T. pfenigii* phaC was amplified from pMON25894 (Reiser et al., *Appl. Microbiol. Biotechnol.* 53(2):209-218 (2000)) with primers FS-05' and FS-C3', which contain engineered Acc65I and BamHI restriction sites. The phaC PCR product was then digested with restriction enzymes Acc65I and BamHI and ligated to similarly digested pTrcN to form pFS90. The primer sequence for FS-05' is (5')-GGGGTACCAGGAGGTTTTTATGTCCCCATTCCCGATCGACATCCG (SEQ ID NO:3) and the primer sequence for FS-C3' is (5')-CGGGATCCTCAGC-CGCGTTCGTTCAGCCAGCGGCCGATCGCCG (SEQ ID NO:4). After *T. pfenigii* phaE and phaC were individually cloned into pTrcN to form pFS89 and pFS90, respectively, phaE was cloned upstream of phaC by digesting pFS89 with MluI and Acc65I, isolating the phaE containing fragment, and ligating it to a similarly digested preparation of pFS90. The resulting plasmid, pFS91, contained the phaEC operon fusion under the $P_{Trc}$ promoter. Finally, pFS92 was created by ligating a MluI-BamHI fragment from pFS91 containing phaEC to pFS16 that had been digested with MluI and BamHIH. Plasmid pFS92 contains the phaEC-orfZ operon fusion under the $P_{Trc}$ promoter.

Plasmid pMS96 was made by cloning alkK (see Table 1A) into pFS91 downstream of phaEC. First, alkK was PCR amplified from *P. oleovorans* genomic DNA using primers K5-1 and K3-1, which were engineered to incorporate BamHI sites onto the ends of the PCR product. The sequence for primer K5-1 is (5')-GCTGAGGATCCAGGAGGTTTT-TATGTTAGGTCAGATGATGCGTAATC (SEQ ID NO:5) and the sequence for primer K3-1 is (5')-CTAGAGGATCCT-TATTCACAGACAGAAGAACTACTG (SEQ ID NO:6). Following amplification, the alkK PCR fragment and pFS91 (described in the paragraph above) were digested with BamHI and ligated to form pMS96. The orientation of alkK in pMS96 was verified to be in the same direction as phaEC by restriction enzyme digestion, thus ensuring the proper construction of a phaEC-alkK operon fusion under the $P_{Trc}$ promoter.

Plasmids pMS93 and pMS102 were constructed by first digesting pACYC177 (Accession #X06402) with BspHI in order to remove the kan marker and ligating it into the unique BspHI site of pFS30 to form pFS73, which contains phaC-orfZ under the control of tandem promoters $P_{Trc}$ and $P_{Re}$. The $P_{Re}$ promoter region was removed by replacing the EcoRI-BspEI fragment of pFS73 containing both $P_{Re}$ and 837 bp from the 5' end of the phaC CDS with an EcoRI-BspEI fragment from pKAS4 (Peoples et al., U.S. Pat. No. 5,480,794) that contained only the 837 bp from the 5' end of phaC. This resulting plasmid, which contains phaC-orfZ under only the $P_{Trc}$ promoter, was designated pMS93. To create pMS102, the orfZ gene was removed from pFS73 by digesting with DraI and self-ligating the plasmid backbone to form pMS74. The alkK gene was PCR-amplified from plasmid pTreN-A.eut-AlkK (described below) using primers K5-2 and K3-2. The sequence for primer K5-2 is (5')-AATTCAGGAG-GTTTTTATGTTAGGTCAGATGATGCGTAATC (SEQ ID NO:7) and the sequence for primer K3-2 is (5')-GATCCT-TATTCACAGACAGAAGAACTACTG (SEQ ID NO:8). Plasmid pMS74 was then digested with SpeI and SbfI and then made blunt-ended via Klenow fill-in and the alkK PCR fragment ligated to the blunted pMS74 backbone to form pMS92. Plasmid pMS92 thus contains the phaC-alkK operon fusion under the control of tandem promoters $P_{Trc}$ and $P_{Re}$. In order to express the operon exclusively from the IPTG-inducible $P_{Trc}$ promoter, the $P_{Re}$ promoter region was removed by replacing the EcoRI-BspEI fragment of pMS92 containing both $P_R$, and 837 bp from the 5' end of the phaC CDS with an EcoRI-BspEI fragment from pMS93 that contained only the 837 bp from the 5' end of phaC. This resulting plasmid, which contains phaC-alkK under only the $P_{Trc}$ promoter, was designated pMS102.

Plasmid pTrcN-A.eut-AlkK was created by first PCR-amplifying alkK from *P. oleovorans* genomic DNA using primers Posynrbs.c (5'-GGAATTCAGGAGGTTTTTATGTTAG-GTCAGATGATGCGTAATCAG) (SEQ ID NO:9) and Posynrbs.r (5'-CGGGATCCTTATTCACAGACAGAA-GAACTACTGCG) (SEQ ID NO:10). The resulting PCR product was digested with EcoRI and BamHI and ligated to similarly digested pTrcN to create pTrcN-AlkK. The $P_{Re}$ promoter was then PCR-amplified from *Ralstonia eutropha* genomic DNA using primers A.eut.PhaG.c (5'-GGAATTCG-GATCCCAAGTACCTTGCCGACATCTATGCGCTGGC) (SEQ ID NO:11) and A.eut.EcoRIs (5'-GGAATTCCCG-GCTCCGGGATTGCCCTGGCCGGACT) (SEQ ID NO:12). The resulting PCR product was digested with EcoRI and ligated to similarly-digested pTrcN-AlkK in order to create pTrcN-A.eut-AlkK.

Plasmids pFS92, pMS96, pMS93, and pMS102 were individually transformed into MG1655 (Jensen, *J. Bacterial.* 175 (10:3401-3407 (1993)) to create four plasmid-bearing strains that contained different combinations of CoA transferase/synthetase (orfZ or alkK) and PHA synthase (phaC or phaEC). These strains were grown in 250 mil, shake flasks to characterize P(5HV) homopolymer production, as described in the following section.

Media, Growth Conditions, and Testing for Production of P(5HV) Homopolymer in Shake Flask Cultures Each plasmid-bearing MG1655 strain was grown overnight in a test tube containing 3 mL LB (Sambrook and Russell, Molecular Cloning: A Laboratory Manual, Cold Spring Harbor Press (2001)) supplemented with appropriate antibiotic at 37° C. with 250 rpm shaking. Antibiotics appropriate for each strain are as follows: 100 µg/mL ampicillin was added to overnight cultures of pFS92- and pMS96-bearing MG1655 strains; and 50 µg/mL Km was added to overnight cultures of pMS93- and pMS102-bearing MG1655 strains. The next day, 0.5 mL of each overnight culture was used to inoculate a shake flask containing 50 mL of fresh LB supplemented with the appropriate antibiotic and grown at 37° C. with 250 rpm shaking. At 3.5 hours, 0.1 mM IPTG was added to the liquid cultures, and at 5 hours, the culture was spun down at 4150 rpm (Sorvall Legend RT benchtop centrifuge) and resuspended in 50 mL of production medium containing 0.1 mM IPTG and the same antibiotic. The production medium consists of 1×E2 minimal salts solution containing 10 g/L glucose, 2.5 g/L LB, 10 g/L Na5HV, 2 mM MgSO$_4$, and 1× Trace Salts Solution. 50×E2 stock solution consists of 1.275 M NaNH$_4$HPO$_4$.4H$_2$O, 1.643 M K$_2$HPO$_4$, and 1.36 M KH$_2$PO$_4$. 1000× stock Trace Salts Solution is prepared by adding per 1 L of 1.5 N HCL: 50 g FeSO$_4$.7H$_2$O, 11 g ZnSO$_4$.7H$_2$O, 2.5 g MnSO$_4$.4H$_2$O, 5 g CuSO$_4$.5H$_2$O, 0.5 g (NH$_4$)$_6$Mo$_7$O$_{24}$.4H$_2$O, 0.1 g Na$_2$B$_4$O$_7$, and 10 g CaCl$_2$.2H$_2$O. The resuspended cultures were transferred to 250 mL shake flasks and incubated at 30° C. for 24 to 72 hours with shaking. At the end of the experiment, cultures were spun down at 4150 rpm, washed once with distilled water, frozen at −80° C. for at least 30 minutes, and lyophilized overnight. The next day, a measured amount of lyophilized cell pellet was added to a glass tube, followed by 3 mL of butanolysis reagent that consists of an equal volume mixture of 99.9% n-butanol and 4.0 N HCl in dioxane with 2 mg/mL diphenylmethane as internal standard. After capping the tubes, they were vortexed briefly and placed on a heat block set to 93° C. for six hours with periodic vortexing. Afterwards, the tube was cooled down to room temperature before adding 3 mL distilled water. The tube was vortexed for approximately 10 s before spinning down at 620 rpm (Sorvall Legend RT benchtop centrifuge) for 2 min. 1 mL of the organic phase was pipetted into a GC vial, which was then analyzed by gas chromatography-flame ionization detection (GC-FID) (Hewlett-Packard 5890 Series II).

The quantity of P(5HV) homopolymer in the cell pellet was determined by comparing against standard curves that were made by adding defined amounts of DVL in separate butanolysis reactions. Three DVL standards ranging from 2-6 mg were used to create the standard curves.

Experimental Results

Table 2 shows that all constructs were able to generate P(5HV). However, MG1655 [pMS93] generated significantly more P(5HV) than any of the other strains demonstrating that the optimal gene combination to polymerize P(5HV) is phaC and orfZ.

TABLE 2

P(5HV) homopolymer production

| Strain [Plasmid] | Relevant genotype | P(5HV) (% dcw) |
|---|---|---|
| MG1655 [pMS93] | Ptrc-phaC-orfZ | 54.6 |
| MG1655 [pFS92] | Ptrc-phaEC-orfZ | 5.7 ± 1.2 |
| MG1655 [pMS96] | Ptrc-phaEC-alkK | 3.82 |
| MG1655 [pMS102] | Ptrc-phaC-alkK | 35.2 |

Example 2

Biosynthesis of P(3HB-Co-5HV) Copolymer from Sodium 5-Hydroxyvalerate

The next experiment was to demonstrate the production of P(3HB-co-5HV) copolymer in an *E. coli* strain capable of synthesizing the 3HB-CoA and 5HV-CoA monomers and incorporating them into PHA.

Strain Construction

The strain used in this example was MBX2641, which is an MG1655 derivative that contains an operon consisting of *R. eutropha* H16 bktB-*B. megaterium* phaB-kan randomly integrated into the chromosome. To carry out the operon integration, strain S17-1λpir (Miller and Mekalanos, *J. Bacteria.* 170(6):2575-2583 (1988)) containing pCJ022 (described below) was mated with MBX1987, which is a nalidixic acid-resistant mutant of MG1655, using a protocol taken from the literature (De Lorenzo and Timmis, *Methods Enzymol.* 235: 386-405 (1994)). Derivatives of MBX1987 carrying the bktB-phaB-kan cassette in the chromosome were selected on LB plates containing 30 µg/mL nalidixic acid (Nl) and 50 µg/mL kanamycin (Km). One such integrant displaying a $Nl^R$ $Km^R$ phenotype was saved as MBX2079. Then, phaEC-cat was randomly integrated into the chromosome of MBX2079 by mating with an S17-1λpir strain carrying the integration vector pUT-C16-cat (described below). Integrants of MBX2079 carrying the phaEC-cat cassette in the chromosome were selected on LB plates containing 25 µg/mL chloramphenicol (Cm). Several integrants possessing the $Nl^R$ $Km^R$ $Cm^R$ phenotype were pooled and subjected to nitrosoguanidine mutagenesis (Miller, *Experiments in Molecular Genetics*, Cold Spring Harbor Laboratory (1972)), with selection on LB plates containing 100 µg/mL Cm. One mutant was isolated and designated MBX2114. Finally, MBX2641 was created by raising a P1 lysate on MBX2114 and transducing into MG1655 as described by Miller (*Experiments in Molecular Genetics*, Cold Spring Harbor Laboratory (1972)) using $Km^R$ as selection. One such transductant was saved and designated MBX2641, which is MG1655 with the bktB-phaB-kan gene cassette randomly integrated into the genome.

Plasmids pFS92 (see Example 1), and pJB84 (construction described below) were individually transformed into MBX2641 that contains bktB-phaB-kan randomly integrated into the chromosome.

Plasmid Construction

Plasmid pCJ022 was made by creating a mini-Tn5 integration vector containing bktB-phaB upstream of a kan marker. To do this, the bktB-phaB operon was assembled on pSE380 (Invitrogen, Carlsbad, Calif.) by first PCR-amplifying bktB with primers MS069 and MS070 from pMON25765 (Slater et al., *J. Bacteriol.* 180(8):1979-1987 (1998)). The sequence for primer MS069 is (5')-GGTGGATCCTTAAGAGGAG-GTTTTTATGACGCGTGAAGTGGTAGTGG (SEQ ID NO:13) and the sequence for primer MS070 is (5')-GGT-GCTAGCTCAGATACGCTCGAAGATGGCG (SEQ ID NO:14). The resulting PCR fragment was digested with BamHI and NheI and ligated to pSE380 that had been cut with the same enzymes. The resulting plasmid was designated pSE380-bktB. Next, phaB was PCR-amplified from pGM10 (McCool and Cannon, *J. Bacteria* 181(2):585-592 (1999)) with primers MS071 and MS072. The sequence for primer MS071 is (5')-GGTCCTAGGTTAAGAGGAGGTTTTTAT-GACAACATTACAAGGTAAAG (SEQ ID NO:15)T and the sequence for primer MS072 is (5')-GGTGCGGCCGCTTA-CATGTATAAGCCGCCGTTAAT (SEQ ID NO:16). The resulting PCR fragment was digested with AvrII and NotI and ligated to pSE380-bktB that had been treated with the same enzymes. The resulting plasmid was designated pSE380-bktBphaB19. After the operon had been assembled, it was moved to pTrcN-kan (a derivative of pTrcN that had the bla gene replaced with the kan gene) by digesting pSE380-bkt-BphaB19 with EcoRI and SpeI and ligating the fragment containing bktB-phaB to pTrcN-kan that had been cut with EcoRI and XbaI. The resulting plasmid was designated pMS115. The bktB-phaB operon was then transferred from pMS115 to the pBSL118 integration vector (Alexeyev et al., *Can. J. Microbial.* 41:1053-1055 (1995)) by digesting pMS115 and pBSL118 with BamHI and ligating together to produce plasmid pCJ022, which was used to integrate bktB-phaB into the chromosome of MG1655.

Plasmid pUT-C16cat was made by removing phaEC from pFS91 with EcoRI and XbaI and blunting the sticky ends using Klenow. Integration vector pUT-cat (De Lorenzo and Timmis, *Methods Enzymol.* 235:386-405 (1994)) was digested with AvrII, blunted using Klenow fill-in, and then ligated to the phaEC fragment. After verifying that phaEC was in the same orientation as the downstream cat marker, the plasmid was designated pUT-C16cat.

Plasmid pJB84 was constructed by PCR-amplifying the aacC ($Gm^R$) marker from pBSL202 (Alexeyev et al., *Can. J. Microbial.* 41:1053-1055 (1995)) using primers JB123b and JB124a, which were engineered to include BspHI sites, on the 5' flanking ends. The sequence for primer JB123b is (5')-TTATTTCATGAACCCTCGAATTGACGCGCTC (SEQ ID NO:17) and the sequence for primer JB124a is (5')-TTATTTCATGAGCTTATCGATACCGTCGACC (SEQ ID NO:18). The resulting PCR fragment containing the aacC gene was digested with BspHI and ligated to pMS93 that had been digested with the same enzyme to form pJB84. Note that this last step was done to replace the original bla ($Ap^R$) marker on pMS93 with aacC ($Gm^R$) in the same orientation.

Experimental Results

MBX2641 strains carrying plasmids pFS92 (described in Example 1) or pJB84 were grown and prepared for GC-FID analysis as described in Example 1. MBX2641 [pJB84] made more copolymer (69.5% dcw) and incorporated more 5HV into copolymer (82.3% PHA) as shown in Table 3.

TABLE 3

P(3HB-co-5HV) production

| Strain [Plasmid] | Relevant Genes Expressed | Total PHA (% dcw) | 3HB Incorporation (% PHA) | 5HV Incorporation (% PHA) |
|---|---|---|---|---|
| MBX2641 [pFS92] | bktB-phaB; phaEC-orfZ | 7.8 | 46 | 54 |
| MBX2641 [pJB84] | bktB-phaB; phaC-orfZ | 69.5 | 18 | 82 |

Example 3

Tunable 5HV Monomer Composition in P(3HB-co-5HV) Copolymer and Effect on Material Properties The copolymer composition was modulated by altering the amounts of Na5HV and glucose added to the production medium. Alternate ways to accomplish this include (1) feeding different amounts of L-lysine to the growth medium to a recombinant cell that can produce 5HV from L-lysine as is shown in Example 6, or (2) deregulating L-lysine pathway genes in recombinant cells that can produce 5HV from glucose via L-lysine as shown in Example 9 and 10.

To demonstrate tunable 5HV monomer composition in P(3HB-co-5HV) copolymer, strain MBX2641 [pFS30] was used that expresses the enzymes for the 3HB pathway (bktB and phaB) in addition to the CoA-transferase (orfZ) and PHA synthase (phaC). Parallel cultures of MBX2641 [PFS30] were grown in either decreasing concentrations of glucose (10, 5, 1, 0.5, 0.1, 0 g/L) or Na5HV (10, 5, 1, 0.5, 0.1, 0 g/L) and analyzed for polymer content as described in Example 1. Table 4 shows that various amounts of 5HV can be incorporated into the P(3HB-co-5HV) copolymer.

TABLE 4

Effect of co-feed on 5HV incorporation into P(3HB-co-5HV)

| Glucose Feed (g/L) | Na5HV Feed (g/L) | Total PHA (% dcw) | 5HV Incorporation (% PHA) |
|---|---|---|---|
| 10 | 10 | 42.5 ± 4.6 | 50.0 ± 3.4 |
| 10 | 5 | 29.1 | 42.3 |
| 10 | 1 | 19.1 | 22.9 |
| 10 | 0.5 | 27.2 | 16.3 |
| 10 | 0.1 | 22.3 | 5.0 |
| 10 | 0 | 14.8 | 2.5 |
| 5 | 10 | 27.6 | 51.4 |
| 1 | 10 | 12.7 | 45.2 |
| 0.5 | 10 | 8.9 | 38.3 |
| 0.1 | 10 | 6.5 | 35.1 |
| 0 | 10 | 6.9 | 29.6 |

In another experiment, a total of 10 P(3HB-co-5HV) copolymer samples that had a wide range of 5HV compositions were generated and then extracted for differential scanning calorimetry (DSC) analysis. Table 5 shows that the glass transition temperature ($T_g$) decreased as the percent composition of 5HV increased in the P(3HB-co-5HV) copolymer. This demonstrates that a wide range of material properties can be obtained by modulating the 5HV comonomer composition.

TABLE 5

Material properties of extracted polymers

| Strain/Origin | Method | % 5HV | $T_g$ (° C.) |
|---|---|---|---|
| MBX648 [pMS93] | Shake flask | 100 | −58 |
| MBX2641 [pJB84] | Shake flask | 82 | −49 |
| MBX2641 [pFS30] | Shake flask | 52 | −34 |
| MBX2641 [pFS30] | Shake flask | 49 | −29 |
| MBX2641 [pFS30] | Shake flask | 47 | −27 |
| MBX2114 [pFS30] | Shake flask | 39 | −30 |
| MBX2641 [pFS30] | Shake flask | 39 | −24 |
| MBX2641 [pFS30] | Shake flask | 23 | −16 |
| MBX2641 [pFS30] | Shake flask | 16 | −9 |
| MBX2641 [pFS30] | Shake flask | 5 | 0 |

Example 4

Synthesis of 3-Hydroxypropionate from Na5HV Via the Fatty Acid Degradation System In order to determine if the fatty acid degradation (FAD) system of E. coli could break down SHY to acetyl-CoA and 3-hydroxypropionyl-CoA (3HP-CoA), plasmid pMS93 (expressing phaC-orfZ from a $P_{trc}$ promoter; see Example 1) was transformed into E. coli K12 strains that were either fadR+, atoC+ (repressed FAD) or fadR−, atoC$_{const}$ (derepressed FAD). MG1655 and LS5218 (Spratt et al., J. Bacteria 146(3): 1166-1169 (1981)) were used as the fadR+, atoC+ and fadR−, atoC$_{const}$ strains, respectively. MG1655 [pMS93] and LS5218 [pMS93] were tested by feeding Na5HV in shake flasks as described in Example 1. GC-FID and GC-Mass Spectroscopy (MS) analysis demonstrated that LS5218 [pMS93] produced P(5HV-co-3HP), whereas MG1655 [pMS93] did not (Table 6). This shows that active fatty acid degradation will produce 3HP from 5HV.

TABLE 6

Incorporation of 3HP into P(5HV-co-3HP)

| Strain [Plasmid] | Relevant Genotype | Total PHA (% dcw) | 5HV Incorporation (% PHA) | 3HP Incorporation (% PHA) |
|---|---|---|---|---|
| MG1655 [pMS93] | fadR+, atoC+ | 63.1 | 100 | 0 |
| LS5218 [pMS93] | fadR−, atoC$_{const}$ | 6.4 | 52 | 48 |

Example 5

Biosynthesis of P(5HV) Homopolymer from L-Lysine

Figure 2B:
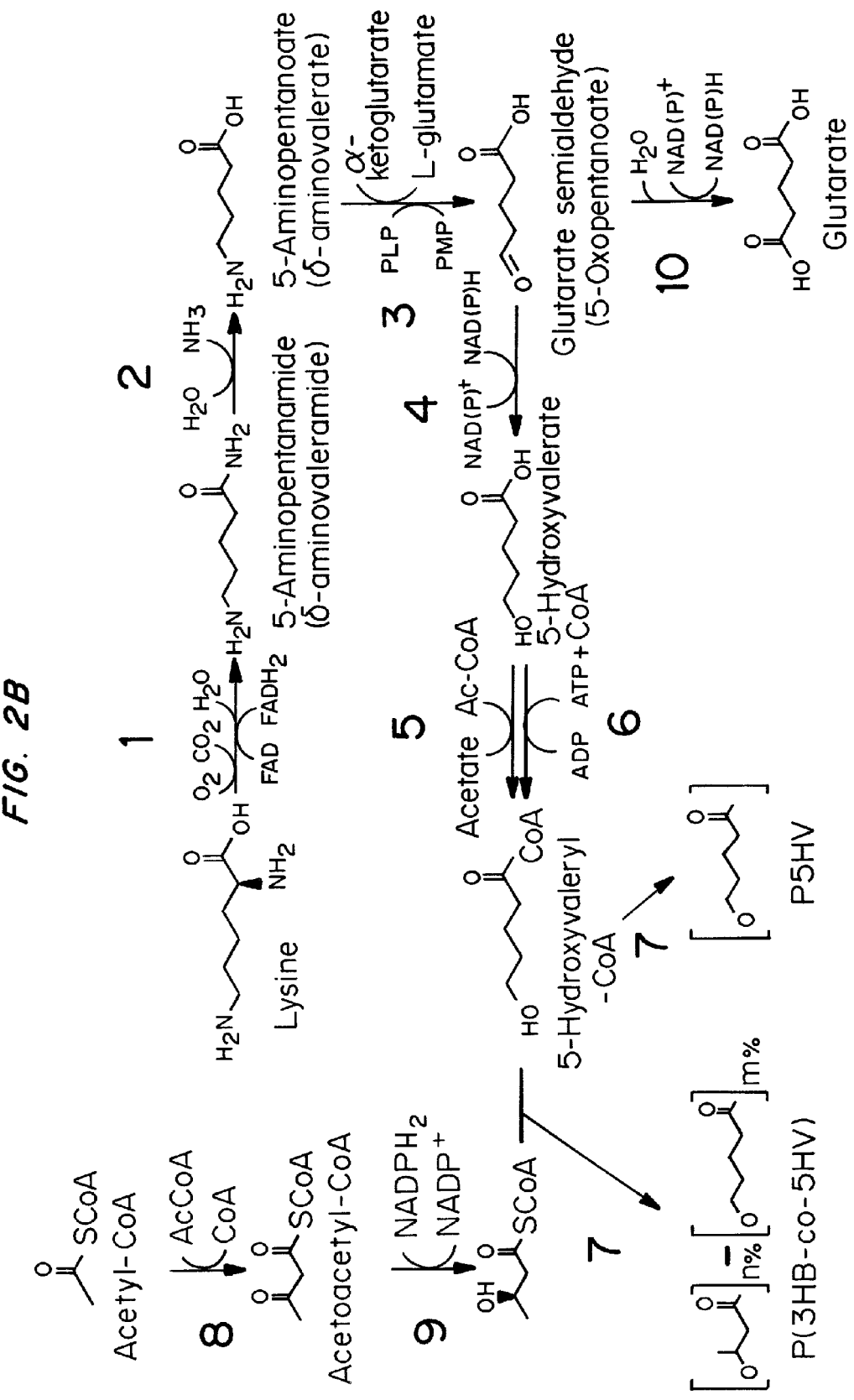

The pathway devised to convert L-lysine to P(5HV) is schematically diagrammed in FIG. 2B and requires six heterologous genes to be cloned and expressed in E. coli: P. putida davB, P. putida davA, P. putida davT, A. thaliana gsaR$_{At}$, C. kluyveri orfZ, and R. eutropha phaC (see Table 1A). A cloning strategy was designed such that the davBAT genes would be cloned into pACYC184 (Chang and Cohen, J. Bacteriol. 134:1141-1156 (1978)) and gsaR$_{At}$, orfZ, and phaC would be cloned into pSE380. These plasmids are designated pJB91 and pMZ28, respectively, and their assembly is described in the next section.

Plasmid Construction

The multiple cloning site of plasmid pSE380 was PCR-amplified with primers JB134 (5'-TGAGCGGATAA-CAATTTCAC) (SEQ ID NO:19) and JB135 (5'-AATAA-CACGTCAACGCAAAAAGGCCATCCGT) (SEQ ID NO:20). The resulting PCR product was digested with BmgBI and cloned into plasmid pACYC184 that was digested with EcoRV and NruI to create pJB78.

Plasmid pJB91 was constructed in a three step process. First, the davBA genes from *P. putida* were PCR-amplified from a genomic DNA preparation using primers JB136 and JB137, which were engineered to incorporate NdeI and BsrGI restriction sites, respectively, on the 5' and 3' ends of the davBA PCR product. The sequence for primer JB136 is (5')-TTTTTCATATGAGGAGGTTTTTATGAA-CAAGAAGAACCGCCA (SEQ ID NO:21) and the sequence for primer JB137 is (5')-TTTTTTGTACATCAGCCTT-TACGCAGGTGCA (SEQ ID NO:22). The resulting PCR product was digested with NdeI and BsrGI and ligated to pJB78 that had been treated with the same enzymes, to give plasmid pJB79. Next, the davT gene from *P. putida* was PCR-amplified from genomic DNA using primers JB138 and JB139, which were engineered to incorporate SpeI and ApaLI restriction sites, respectively, on the 5' and 3' ends of the davT PCR product. The sequence for primer JB138 is (5')-TATATACTAGTAGGAGGATAATATGAG-CAAAACCAACGAATC (SEQ ID NO:23) and the sequence for primer JB139 is (5')-TTTTTGTGCACTCAGGC-GATTTCAGCGAAGC (SEQ ID NO:24). The resulting PCR product was digested with SpeI and ApaLI and ligated to pJB79 that had been digested with the same enzymes, thus creating plasmid pJB80. Finally, the ompA promoter was PCR-amplified from *E. coli* K12 genomic DNA using primers JB141 and JB142, which were engineered to incorporate BmgBI and AseI restriction sites, respectively, on the 5' and 3' ends. The resulting PCR product was digested with BmgBI and AseI and ligated to pJB80 that had been digested with SnaBI and NdeI to form plasmid pJB82. Plasmid pJB91 was constructed by digesting a davBA PCR product created with primers JB136 and JB137 (as described above) with DraIII and ligating the 507 bp fragment to pJB82 that had been digested with the same enzyme, thus creating plasmid pJB91. This construction was done in order to correct a nonsense mutation that had been discovered in the davB CDS of pJB82. Plasmid pJB80 contains the davBAT operon under the constitutive $P_{tet}$ promoter, while plasmid pJB91 contains the same operon under the strong $P_{ompA}$ promoter.

Plasmid pMZ28 was constructed by digesting plasmid pJ31:7950, which is a construct created by DNA 2.0 (Menlo Park, Calif.) and contained gsaR$_{At}$ that is codon-optimized for expression in *E. coli* K12, with BsrGI. The resulting fragment containing gsaR$_{At}$ was ligated to pFS30 that had also been cut with BsrGI. After verifying that the orientation of gsaR$_{At}$ was in the same direction as phaC-org by restriction enzyme digestion, the resulting plasmid was designated pMZ28.

Experimental Results

MG1655 [pMZ28] that expresses an incomplete L-lysine to P(5HV) pathway and MG1655 [pMZ28, pJB91] that expresses the entire L-lysine to P(5HV) pathway were inoculated in a test tube containing 3 mL LB supplemented with appropriate antibiotic (25 µg/mL chloramphenicol for pJB91; 100 µg/mL ampicillin for pMZ28) and grown overnight at 37° C. with 250 rpm shaking. The next day, 0.5 mL of each overnight culture was used to inoculate a shake flask containing 50 mL of fresh LB supplemented with the appropriate antibiotic(s) and grown at 37° C. with 250 rpm shaking. At 3.5 hours, 0.1 mM IPTG was added to the liquid cultures, and at 5 hours, the cultures were spun down at 4150 rpm (Sorvall Legend RT benchtop centrifuge) and resuspended in 50 mL of production medium that consisted of 1×E2 minimal salts solution containing 10 g/L glucose, 2.5 g/L LB, 10 g/L L-lysine, 2 mM MgSO$_4$, 1× Trace Salts Solution, and 0.1 mM IPTG. The recipes for E2 salts and Trace Salts Solution are given in Example 1.

Shake flask growth conditions and the analysis protocol for PHA content are as described in Example 1. Table 7 shows that eight-fold more P(5HV) was produced after introduction of the davBAT operon.

TABLE 7

P(5HV) production from L-lysine

| Strain [Plasmid] | Relevant genotype | Total PHA (% dcw) |
| --- | --- | --- |
| MG1655 [pMZ28] | pMZ28: P$_{Trc}$-gsaR$_{At}$-P$_{Re}$-phaC-orfZ | 0.01 |
| MG1655 [pMZ28, pJB91] | pMZ28: P$_{Trc}$-gsaR$_{At}$-P$_{Re}$-phaC-orfZ<br>pJB91: P$_{ompA}$-davBAT | 0.08 |

Example 6

Biosynthesis of P(3HB-co-5HV) Copolymer from L-Lysine

The pathway devised to convert L-lysine to P(5HV) was also introduced into strain MBX2641 expressing bktB and phaB in order to produce P(3HB-co-5HV) copolymer from L-lysine and eventually glucose.

Plasmid Construction

The genes comprising the pathway in this example include: *P. putida* davB, *P. putida* davA, *P. putida* davT, *C. kluyveri* orfZ, *R. eutropha* phaC, and either *A. thaliana* gsaR$_{At}$ or *A. terreus* gsaR$_{At2}$ (see Table 1A).

Plasmid pJB90, which contains an alternate pathway consisting of the gsaR$_{At2}$, phaC, and orfZ genes, was created in the following manner. The *A. terreus* gsaR$_{At2}$ gene, codon-optimized for expression in *E. coli* K12, was PCR-amplified from pSG40 (a construct created by DNA 2.0 (Menlo Park, Calif.)) using primers JB145 and JB146. Both primers contained BglII sites at the 5' ends. The sequence for primer JB145 is (5')-TTTTTAGATCTAGGAGGTTTTTATGCT-GCGTGCTGCTTCTCG (SEQ ID NO:25) and the sequence of primer JB146 is (5')-TTTTTAGATCTTTAGCGGAAAT-AGTTTGGAC (SEQ ID NO:26). The resulting PCR fragment was digested with BglII and ligated into the corresponding site of pJB84 to create pJB90.

Experimental Results

Strains MBX2641 [pJB78, pJB84], MBX2641 [pJB91, pMZ28], and MBX2641 [pJB91, pJB90] were grown in shake flasks and analyzed for PHA content and composition as described in Example 1 and 2, in order to characterize the production of P(3HB-co-5HV) from L-lysine and glucose. MBX2641 [pJB78, pPB84], MBX2641 [pJB91, pMZ28], and MBX2641 [pJB91, pJB90] were inoculated in test tubes containing 3 mL LB supplemented with 25 µg/mL chloramphenicol and 100 µg/mL ampicillin and grown overnight at 37° C. with 250 rpm shaking. The next day, 0.5 mL of each overnight culture was used to inoculate a shake flask containing 50 mL of fresh LB supplemented with the same antibiotic and grown at 37° C. with 250 rpm shaking. At 3.5 hours, 0.1 mM IPTG was added to the liquid cultures, and at 5 hours, the cultures were spun down at 4150 rpm (Sorvall Legend RT benchtop centrifuge) and resuspended in 50 mL of production medium that consisted of 1×E2 minimal salts solution containing 10 g/L glucose, 2.5 g/L LB, 10 g/L L-lysine, 2 mM MgSO$_4$, 1× Trace Salts Solution, and 0.1 mM IPTG. The recipes for E2 salts and Trace Salts Solution are given in Example 1.

As shown in Table 8, strain MBX2641 [pJB78, pJB384], which does not have the genes that convert L-lysine to 5HV, was unable to produce 5HV from L-lysine and produced only P(3HB) homopolymer. Strains MBX2641 [pJB91, pMZ28] and MBX2641 [pJB91, pJB90], both of which contain the entire pathway from L-lysine to 5HV-CoA, incorporated 5HV to 2.5% wt and 5% wt, respectively, of the total copolymer. This demonstrates that the davBAT and gsaR genes need to be expressed in order to produce 5HV-containing copolymers from L-lysine.

TABLE 8

P(3HB-co-5HV) production from L-lysine

| Strain [Plasmid] | Relevant Plasmid Genotype | | Total PHA (% dcw) | 3HB Incorporation (% PHA) | 5HV Incorporation (% PHA) |
| --- | --- | --- | --- | --- | --- |
| | P$_{ompA}$-davBAT | P$_{Trc}$-phaC-gsaR$_x$-orfZ | | | |
| MBX2641 [pJB78, pJB84] | none | P$_{Trc}$-phaC-orfZ (no gsaR$_x$) | 38 ± 9 | 100 | 0 |
| MBX2641 [pJB91, pMZ28] | Present | P$_{Trc}$-phaC-gsaR$_{At}$-orfZ | 33 ± 11 | 97.5 ± 1.5 | 2.5 ± 1.5 |
| MBX2641 [pJB91, pJB90] | Present | P$_{Trc}$-phaC-gsaR$_{At2}$-orfZ | 41 ± 11 | 95.0 ± 2.3 | 5.0 ± 2.3 |

Example 7

Improved Biosynthesis of 5HV-Containing PHA Polymers from L-Lysine

Due to the fact that 5HV was incorporated at an unexpectedly low level, the existence of a competing pathway was considered. In order to see if glutarate could be produced from L-lysine, MG1655 [pJB91] expressing the davBAT genes from the plasmid was grown in LB medium containing 25 mg/L chloramphenicol at 30° C. with shaking for 6 h. Aliquots of 25 µL, mid-log phase cultures were inoculated into 475 µL E0 a minimum medium and incubated at 30° C. with shaking at 250 rpm for 48 h. The E0 minimum medium consisted of 10 g/L glucose, 4 g/L lysine, 58 mM K2HPO$_4$, 27 mM KH$_2$PO$_4$, 2 mM MgSO$_4$, 25 µg/mL chloramphenicol, 0.1 mM IPTG, and trace elements. Glutarate, present in the supernatant, was measured by GC-MS as outlined below: supernatants from fermentation broth were obtained by centrifugation and 1 µL of the sample was pipetted to a fresh Eppendorf tube containing 1 µL of 1 g/L 4-aminobutyrate (GABA) as internal standard. Samples were dried in a Labconco centrivap and resuspended in 100 µL acetonitrile (ACN): N-(t-butyldimethylsilyl)-N-methyltrifluoroacetamide (MTBSTFA) 1:1 solution by sonication for 3 h. Samples were then derivatized at 65° C. for 30 min, centrifuged to remove insoluble material and supernatants injected into an Agilent 5975 GC-MS equipped with a HP-5 ms column using the following acquisition parameters: carrier gas Helium flow rate 2 ml/min, scan mode m/z 65-700, solvent delay for 3.5 min, oven program: 150° C. for 2 mM, then ramp up to 280° C. at 3° C./min, ion source temperature 230° C., the quadrupole mass filter temperature 150° C.

Interestingly, 0.6 g/L glutarate was produced from L-lysine when the davBAT operon was overexpressed in MG1655. The davBAT operon expresses genes encoding enzymes that convert L-lysine to GSA. Glutarate may be produced by an endogenous E. coli gene whose encoded enzyme can oxidize GSA to glutarate.

Examination of probable enzymatic reactions from GSA to glutarate led to the identification of two likely endogenous E. coli GSA dehydrogenase genes, gabD and/or yneI (see Table 1A). These two genes have been identified earlier to oxidize succinic semialdehyde to succinic acid (Dennis and Valentin, U.S. Pat. No. 6,117,658) but have not been shown to oxidize GSA to glutarate. To test if a gabD- and yneI-negative strain still produces glutarate from L-lysine, the following strains were constructed.

Single null gabD and yneI mutants were constructed by the Red/ET Recombineering method described by Datsenko and Wanner (Proc. Natl. Acad. Sci. USA. 97:6640-6645 (2000)). The process of deleting gabD from the chromosome of MG1655 involved the replacement of gabD with an FRT-flanked kan marker via PCR-mediated homologous recombination. The FRT-flanked kan marker was PCR-amplified from plasmid pKD4 (Datsenko and Wanner, Proc. Natl. Acad. Sci. USA. 97:6640-6645 (2000)) by using primers RF314 5'-GCAAGCCAGAGTAACCCCGGACG-CACGCTGCGAGCGGCACGTAGTG TGGATGCCTTA-CACGCCGCATTTAATCAATAACCT-TGAGCGATTGTGT AGGCTGGAGCTGCTTC (SEQ ID NO:27) and RF315 5'-GAATTTGCCCAACGCCACGGG-GAATCGCCTGACTGCGGCGCTGCATT AACTCTT-TATTGCTGTTCATTCGCATTCTCCA-GATGGGAATTAGCCAT GGTCCATATGAATAT (SEQ ID NO:28).

The yneI gene was deleted from the chromosome of MG1655 by replacement with an FRT-flanked kan marker. This marker was PCR-amplified from plasmid pKD4 using primers MS220 5'-GCAAGAGTAAATCTGCGTATCT-TCATACCATGACTCATAAAGGAGAT ACCCCGGTG-TAGGCTGGAGCTGCTTC (SEQ ID NO:29) and MS217 5'-ACCGCAGGTCTGAAAAGACCTGCGAG-TATATCAGAGCTGAATATGTC GCGCATATGAATATC-CTCCTTAGT (SEQ ID NO:30) that introduced 50 bp flanking regions of homology to the gene to be deleted. Replacement of yneI with this DNA fragment did not work, and hence, another PCR fragment was created that had increased regions of homology for gene replacement. To accomplish this, an additional round of PCR was performed with the PCR fragment generated above as template and primers MS223 5'-TCGATTCGTGAATAAGTGGCT-TAATATTATTCATTTTAAAGCAAGAGT AAATCTGCG-TATC (SEQ ID NO:31) and MS224 5'-GCCACTTTC-TACTCCTGGACCGCAGGTCTGAAAAGACCTGCGAG- TAT ATCAGAGCTG (SEQ ID NO:32). Successful replacement of yneI with FRT-kan-FRT was achieved. The kan marker was then removed as described in Datsenko and Wanner (Proc. Natl. Acad. Sci. USA. 97:6640-6645 (2000)).

The MG1655 ΔgabD::FRT-kan-FRT, ΔyneI::FRT was constructed by P1-mediated transduction from MG1655ΔgabD::FRT-kan-FRT to MG1655ΔyneI::FRT, and the remaining kan marker was further removed using the same method as described above. The resulting strain MG1655 ΔgabD::FRT, ΔyneI::FRT was transformed with pJB91 and analyzed for glutarate production from L-lysine in an experiment analogous to the one described above with MG1655 [pJB91] expressing the davBAT genes from the plasmid.

In contrast to MG1655 [pJB91] that produced 0.6 g/L glutarate from L-lysine, strain MG1655 ΔgabD::FRT, ΔyneI::FRT [pJB91] did not produce any glutarate from L-lysine demonstrating that either the E. coli endogenous gabD and/or yneI were responsible for converting GSA to glutarate.

Improved Production of P(3HB-co-5HV) Copolymers from L-Lysine

Improved 5HV flux from L-lysine was accomplished by deleting the endogenous GSA dehydrogenase encoding genes gabD and yneI in a strain that produced the 3HB-co-5HV copolymer.

MBX2855 was constructed by transforming plasmids pJB91 and pJB90 into strain MBX2641. This strain has all the genes to produce P(3HB-co-5HV) from glucose and L-lysine.

MG1655 ΔgabD::FRT, ΔyneI::FRT was P1-transduced with donor strain MBX2114 that conferred PHB producing capabilities as described in Example 2. This strain was further transformed with pJB90 and pJB91, which expressed the L-lysine to P(5HV) pathway genes as described in Examples 6 and 5, respectively. The resulting strain was designated as MBX3378 and has all the genes to produce P(3HB-co-5HV) from glucose and L-lysine but unlike MBX2855 has both the gabD and yneI genes removed from the genome.

A shake-plate fermentation was conducted using strain MBX2855 and its GSA dehydrogenase-deficient counterpart MBX3 378. Cells were incubated and analyzed under the same conditions as described above (shaking at 300 rpm at 30° C.). The E0 minimum medium consisted of 10 g/L glucose, 2 g/L L-lysine, 58 mM K2HPO$_4$, 27 mM KH$_2$PO$_4$, 2 mM MgSO$_4$, 25 µg/mL chloramphenicol, 5 µg/mL gentamicin, 0.1 mM IPTG, and trace elements as described in a previous example. The carbon flux from L-lysine to 5HV was dramatically improved in the GSA dehydrogenase-deficient strain MBX3378 as compared to MBX2855 that contained wild-type GSA dehydrogenase activity as shown in Table 9. In order to significantly improve production of SHY containing PHA, GSA dehydrogenase genes such as gabD and yneI need to be removed from the genome of production hosts.

Example 8

Biosynthesis of L-Lysine from Glucose

Allosteric feedback regulation occurs in the L-lysine pathway through the genes lysC and dapA. Therefore, this control needs to be eliminated in order to enable increased L-lysine production from glucose. The procedure to do this is well-established and has been described for both genes (Kojima et al., U.S. Pat. No. 6,040,160). E. coli mutants possessing deregulated lysC and dapA can be obtained first by deleting metL and thrA from E. coli. LysC, MetL and ThrA are isozymes that all catalyze the same aspartate kinase reaction, so it will be necessary to eliminate the latter two before mutations in lysC can be positively selected. Once a ΔmetL ΔthrA strain has been made, it can be mutated with N-methyl-N'-nitro-N-nitrosoguanidine (NTG). The resulting mutant pool would then be grown in a minimal medium containing S-2-aminoethylcysteine (AEC), a non-metabolizable analog of L-lysine, in order to put pressure on lysC and dapA. Since metL and thrA are missing, only mutations that desensitize lysC and dapA to L-lysine (or its AEC analog) will allow the cell to synthesize L-lysine, threonine, and methionine, and thus survive. Further manipulations can be carried out by overexpressing deregulated lysC, deregulated dapA, and other pathway genes from a recombinant promoter in order to increase flux capacity and to eliminate transcriptional regulation.

Example 9

Biosynthesis of P(5HV) Homopolymer from Glucose

P(5HV) was produced from glucose as the sole carbon source in an E. coli strain capable of synthesizing the 5HV-CoA monomers from glucose and incorporating them into PHA. For that, a strain was constructed that expressed not only the genes required to produce P(5HV) homopolymer from L-lysine, but which also expressed a mutated dapA gene called dapA$^{fbr}$ that encodes a L-lysine feedback-resistant dihydrodipicolinate synthase. The first part of this example will describe the construction of the plasmids required to demonstrate this ability.

Plasmids Construction

In E. coli, allosteric regulation occurs in the L-lysine pathway through aspartate kinase III and dihydrodipicolinate synthase encoded by the lysC and dapA genes, respectively (FIG. 6). In order to increase production of L-lysine and eventually P(5HV) homopolymer from glucose, the allosteric regulation needs to be reduced or entirely eliminated. The procedure to do this is well-established and has been described for both genes (Kojima et al., U.S. Pat. No. 6,040,160). An L-lysine feed-back resistant dapA$^{fbr}$ gene was constructed that had the

TABLE 9

Improved P(3HB-co-5HV) production from L-lysine

| Strain [Plasmid] | Relevant Genes Expressed | Relevant Gene Knock-outs | Total PHA (% dcw) | 3HB Incorporation (% PHA) | 5HV Incorporation (% PHA) |
|---|---|---|---|---|---|
| MBX2855 | P$_{ompA}$-davBAT, P$_{Trc}$-phaC-gsaR$_{At2}$-orfZ | none | 17.3 | 98.6 | 1.4 |
| MBX3378 | P$_{ompA}$-davBAT, P$_{Trc}$-phaC-gsaR$_{At2}$-orfZ | gabD$^-$, yneI | 24.7 | 64.9 | 35.1 |

352$^{th}$ nucleotide residue changed from cytosine to thymine (dapA$^{C352t}$). This was obtained by PCR amplification of the chromosomal *E. coli* dapA gene generating two DNA fragments using primers that introduced the desired base change, followed by splicing by overlap extension PCR (SOE-PCR) to fuse the two DNA fragments. The SOE-PCR method has been described earlier (Ho et al., *Gene* 77(1):51-9 (1989). In detail, one DNA fragment contained the 1$^{st}$ to 366$^{th}$ nucleotide pairs of the dapA gene that was amplified with primers DE081 (5'-AAAAGAATTCTTAATTAATTCTAGAAGGAGGTTTCATATGTTCACGG GAAGTATT GTC) (SEQ ID NO:33) and DE082 (5'-AGCGATGGCTTTGAAATACTGATACAAACCTTC) (SEQ ID NO:34), and the other DNA fragment contained the 337$^{th}$ to 879$^{th}$ nucleotide pairs of dapA amplified with primers DE083 (5'-GAAGGTTTGTATCAGTATTTCAAAGCCATCGCT) (SEQ ID NO:35) and DE084 (5'-CCCGAGCTCGTTTAAACTTAATTAAGACTAGTTTTACAGCAAACCGG CATGCTT) (SEQ ID NO:36). The primers DE082 and DE083 are reverse complementary and were designed to introduce the cytosine to thymine base change at the 352$^{th}$ nucleotide residue. The two DNA fragments from the first round of PCRs were fused by SOE-PCR using primers DE081 and DE084. The resulting PCR product was digested with XbaI and SacI and ligated to pDE031 that had been digested with SpeI and SacI, thus creating plasmid pDE035. Plasmid pDE031, containing a synthetic constitutive promoter (P$_{syn1}$) was constructed by digesting a synthesized 63 bp double-stranded DNA fragment (5'-TTTTTCTAGATTGACAGCTAGCTCAGTCCTAGGTATAATGCTAGCACT AGTGTTTAAACCCCC) (SEQ ID NO:37) with XbaI and PmeI and ligated into the same restriction enzyme sites of a pBluescript II SK(+) plasmid (Stratagene, La Jolla, Calif.) that was previously engineered to contain these sites. The P$_{syn1}$-dapA$^{C352T}$ gene construct in pDE035 was digested with XhoI and PmeI, which was followed by ligation with the plasmid pJB90 (described in Example 6) that had been digested with BsrGI, blunted with Mung Bean nuclease, and digested a second time with XhoI to generate plasmid pJG22 that expressed phaC-gsaR$_{At}$-orfZ operon from the P$_{trc}$ promoter and the dapA$^{C352T}$ gene from the P$_{syn1}$ promoter.

Experimental Results

Plasmid pJG22 was transformed along with plasmids pJB91 (described in Example 5) into strain MBX3342 (MG1655 ΔgabD::FRT ΔyneI::FRT) to form strain MBX3342 [pJB91, pJG22]. Plasmids pSE380 and pACYC184, the empty vectors used to construct pJG22 and pJB91, respectively, were also transformed into strain MBX3342 to create the negative control strain MBX3342 [pSE380, pACYC184]. These strains were incubated for 48 h shaking at 300 rpm at 30° C. in 2×E2 medium and analyzed as described in the earlier examples. The medium consisted of 15 g/L glucose, 52 mM NaNH$_4$HPO$_4$, 66 mM K2HPO$_4$, 54 mM KH$_2$PO$_4$, 2 mM MgSO$_4$, 0.1 mM IPTG, and trace elements as described above. For the culture media for MBX3342 [pJB91, pJG22], 25 μg/mL chloramphenicol and 5 μg/mL gentamicin were supplemented, while 25 μg/mL chloramphenicol and 100 μg/mL ampicillin were added for MBX3342 [pSE380, pACYC184]. The data in Table 10 shows that MBX3342 [pJB9, pJG22] produced 2.60% dry cell weight (DCW) P(5HV) homopolymer while strain MBX3342 [pSE380, pACYC184] did not produce any PHA. These results demonstrate that a strain expressing the feedback resistant dapA gene in addition to the L-lysine to P(5HV) pathway genes can produce P(5HV) from glucose as the sole carbon source.

TABLE 10

P(5HV) production from glucose

| Strain [Plasmid] | Relevant Plasmid Genotype | Total PHA (% dcw) |
|---|---|---|
| MBX3342 [pSE380, pACYC184] | pSE380: empty vector control pACYC184: empty vector control | 0.0 |
| MBX3342 [pJG22, pJB91] | pJG22: P$_{Trc}$-phaC-gsaR$_{At}$-orfZ P$_{syn1}$-dapA$^{C352T}$ pJB91: P$_{ompA}$-davBAT | 2.60 |

Example 10

Biosynthesis of P(3HB-co-5HV) Copolymer from Glucose

The next experiment was to demonstrate the production of P(3HB-co-5HV) copolymer from glucose in an *E. coli* strain capable of synthesizing the 3HB-CoA and 5HV-CoA monomers and incorporating them into PHA.

Experimental Results

The btkB-phaB-kan genes from strain MBX2114 were P1-transduced into MBX3342 generating strain MBX3344. MBX3344 was transformed with plasmids pJB91 and pJG22 to create strain MBX3344 [p. 11391, pJG22]. The plasmids pSE380 and pACYC184, the empty vectors used to construct pJG22 and pJB91, respectively, were also transformed into MBX3344 to create a negative control strain, MBX3344 [pSE380, pACYC184]. These strains were incubated for 48 h shaking at 300 rpm at 30° C. in 2×E2 medium and analyzed as described in the earlier examples. The medium consisted of 15 g/L glucose, 52 mM NaNH$_4$HPO$_4$, 66 mM K2HPO$_4$, 54 mM KH$_2$PO$_4$, 2 mM MgSO$_4$, 0.1 mM IPTG, and trace elements as described above. For the culture media for MBX3344 [pJB91, pJG22], 25 μg/mL chloramphenicol and 5 μg/mL gentamicin were supplemented while 25 μg/mL chloramphenicol and 100 μg/mL ampicillin were added for MBX3344 [pSE380, pACYC184]. The culture broth was supplemented with 10 g/L glucose after 24 hours incubation. Table 11 shows that 5HV could be incorporated into the strain containing all the P(3HB-co-5HV) metabolic pathway genes from glucose as the sole carbon source.

TABLE 11

P(3HB-co-5HV) production from glucose

| Strain [Plasmid] | Relevant Plasmid Genotype | Total PHA (% dcw) | 3HB Incorporation (% PHA) | 5HV Incorporation (% PHA) |
|---|---|---|---|---|
| MBX3344 [pSE380, pACYC184] | pSE380: empty vector control pACYC184: empty vector control | 0 | 100 | 0 |

TABLE 11-continued

P(3HB-co-5HV) production from glucose

| Strain [Plasmid] | Relevant Plasmid Genotype | Total PHA (% dcw) | 3HB Incorporation (% PHA) | 5HV Incorporation (% PHA) |
|---|---|---|---|---|
| MBX3344 [pJG22, pJB91] | pJG22: $P_{Trc}$-phaC-gsa$R_{At}$-orfZ $P_{syn1}$-dapA$^{C352T}$ pJB91: $P_{ompA}$-davBAT | 42 | 92 | 8.0 |

Next, strain MBX3824 (W3110 ΔgabD::FRT ΔyneI::FRT ΔcadA::FRT ΔldcC::FRT ΔargO::FRT bktB-phaB-kan) was tested as the host strain to produce P(3HB-co-5HV) copolymer from glucose. In this strain, the competing pathways that may divert L-lysine away from the 5HV-CoA co-monomer were removed from the E. coli genome.

The first competing pathway may convert L-lysine to cadaverine and consists of two L-lysine decarboxylase enzymes (EC number 4.1.1.18) encoded by cadA (Meng and Bennett, J. Bacteriol. 174(8):2659-2669 (1992); EcoCyc accession number: EG10131) and ldcC (see Table 1A; Yamamoto et al., Genes Genet. Syst. 72(3):167-72 (1997); EcoCyc accession number: G6094).

A second competing pathway may export L-lysine out of the microbial cell. In Corynebacterium glutamicum, the L-lysine export protein has been identified as LysE (see Table 1A; Vrljic et al., Mol. Microbiol. 22 (5): 815-826 (1996)). In order to identify putative L-lysine exporter genes in E. coli, several literature and patent searches as well as BLAST and Psi-BLAST searches using C. glutamicum LysE as the query were conducted. Six proteins were found to be targets for removal from the E. coli genome in order to prevent L-lysine export outside of the cell. They include: (1) ArgO (a.k.a. YggA, Nandineni and Gowrishankar, J. Bacteriol. 186:3539-3546 (2004)), (2) YfiK (a.k.a. EamB; Franke et al., J. Bacteriol. 185:1161-1166 (2003)), (3) RhtB (formerly called YigK; Zakataeva et al., FEBS Lett. 452(3):228-32 (1999)), (4) YahN (Kutukova et al., Mol. Biol. (Mosk.) 39(3); 374-378 (2005)), (5) RhtC (formerly called YigJ; Zakataeva et al., FEBS Lett. 452(3):228-32 (1999)), and (6) YeaS (a.k.a. LeuE; Kutukova et al., FEBS Lett. 579(21):4629-34 (2005)). ArgO appeared to be the most likely candidate to export L-lysine out of E. coli cells based on its lowest e-value of 2e-22 in BLASTP searches using LysE from C. glutamicum as the query, the closest clustered with LysE in a Neighbor Join Tree after ClustalX (Thompson et al., Nucleic Acids Res. 25: 4876-4882 (1997)) with C. glutamicum LysE and the six E. coli homologues, and the reported 3-fold increased resistance to L-lysine as well as a 38% higher L-lysine accumulation when argO was overexpressed as compared to vector-only control strains (Livshits et al., U.S. Pat. No. 6,979,560). However, the other identified proteins may export L-lysine too and therefore are also targets for gene deletion.

Another competing pathway may convert L-lysine to (R)-β-lysine which is catalyzed by lysine 2,3-aminomutase (EC number 5.4.3.-) encoded by yjeK of E. coli (EcoCyc accession number: G7836; Behshad et al., Biochemistry 45(42): 12639-46 (2006)).

Single null cadA and ldcC mutants were constructed by the Red/ET Recombineering method from Gene Bridges as described previously using the following primers: DE118 (5'-TGTCCCATGTGTTGGGAGGGGCCTTTTT-TACCTGGAGATATGACTGTG TAGGCTGGAGCT-GCTTC) (SEQ ID NO:38) and DE119 (5'-GAG-CAAAAAAGGGAAGTGGCAAGCCACTTCCCTTGTA-CGAGCTAAA TGGGAATTAGCCATGGTCC) (SEQ ID NO:39) for a ΔcadA::FRT-kan-FRT mutation and DE122 (5'-GTTTGAGCAGGCTATGATTAAGGAAG-GATTTTCCAGGAGGAACACGT GTAGGCTGGAGCT-GCTTC) (SEQ ID NO:40) and DE123 (5'-TATTTGTTAA-CAGCACGTTACTCGCCCGGAAGCCGCTCTGGCAA-GAT GGGAATTAGCCATGGTCC) (SEQ ID NO:41) for ΔldcC::FRT-cat-FRT mutation. A single null argO mutation was constructed by the Red/ET Recombineering method using primers DE106 (5'-GTGTTTTCTTATTACTTTC-AAGGTCTTGCACTTGGGGCGGCTATGGTG TAG-GCTGGAGCTGCTTC) (SEQ ID NO:42) and DE107 (5'-CTAACTGAACAAGGCTTGTGCATGAG-CAATACCGTCTCTCGCCAG ATGGGAATTAGCCATGGTCC) (SEQ ID NO:43). The W3110 ΔgabD::FRT ΔyneI::FRT ΔcadA::FRT ΔldcC::FRT ΔargO::FRT was constructed by iterative P1-mediated transductions of ΔgabD::FRT-kan-FRT, ΔyneI::FRT-kan-FRT, ΔcadA::FRT-kan-FRT, ΔldcC::FRT-cat-FRT, ΔcadA::FRT-kan-FRT cassettes into strain W3110 (Bachmann, Bacterial. Rev., 36 (4):525-557 (1972)), which was followed by removal of kan or cat markers after each P1-mediated transduction as described in earlier examples. The resulting strain MBX3818 was P1-transduced with donor strain MBX2114 to finish the construction of MBX3824. The plasmids pJG22 and pJB91 were transformed into MBX3824 and the resulting strain MBX3824 [pJG22, pJB91] was tested for the production of P(3HB-co-5HV) copolymer along with MBX3344 [pJG22, pJB91]. These strains were incubated for 48 h shaking at 300 rpm at 30° C. in 1.5×E2 medium and analyzed as described in the earlier examples. The medium consisted of 15 g/L glucose, 39 mM NaNH$_4$HPO$_4$, 49.5 mM K$_2$HPO$_4$, 40.5 mM KH$_2$PO$_4$, 2 mM MgSO$_4$, 0.1 mM IPTG, and trace elements as described above. The culture media were supplemented with 25 μg/mL chloramphenicol and 5 μg/mL gentamicin. Table 12 shows that various strains with different genetic backgrounds have the ability to produce P(3HB-co-5HV) from glucose with different compositions of 5HV in the polymer. In particular, removing competing pathways that divert carbon away from 5HV-CoA, such as removing the L-lysine export protein argO or the two lysine decarboxylase genes cadA and ldcC, increase 511V incorporation into PHA.

TABLE 12

P(3HB-co-5HV) production from glucose

| Strain [Plasmid] | Relevant Genotype | Total PHA (% dcw) | 3HB Incorporation (% PHA) | 5HV Incorporation (% PHA) |
|---|---|---|---|---|
| MBX3344 [pJG22, | MBX3344: MG1655 ΔgabD::FRT ΔyneI::FRT bktB-phaB-kan | 47 | 89 | 11 |

TABLE 12-continued

P(3HB-co-5HV) production from glucose

| Strain [Plasmid] | Relevant Genotype | Total PHA (% dcw) | 3HB Incorporation (% PHA) | 5HV Incorporation (% PHA) |
|---|---|---|---|---|
| pJB91] | pJG22: $P_{Trc}$-phaC-gsaR$_{At}$-orfZ $P_{syn1}$-dapA$^{C352T}$ pJB91: $P_{ompA}$-davBAT | | | |
| MBX3824 [pJG22, pJB91] | MBX3824: W3110 ΔgabD::FRT ΔyneI::FRT ΔcadA::FRT ΔldcC::FRT ΔargO::FRT bktB-phaB-kan pJG22: $P_{Trc}$-phaC-gsaR$_{At}$-orfZ $P_{syn1}$-dapA$^{C352T}$ pJB91: $P_{ompA}$-davBAT | 33 | 81 | 19 |

Example 11

Biosynthesis of P(4HB-co-5HV) Copolymer from Sodium 4-hydroxybutyrate and sodium 5-hydroxyvalerate The next experiment was to demonstrate the production of P(4HB-co-5HV) copolymer in an *E. coli* strain capable of synthesizing the 4HB-CoA and 5HV-CoA monomers and incorporating them into PHA. Methods for engineering 4HB co-monomers in recombinant organisms have been described in detail in U.S. Pat. No. 6,117,658, U.S. Pat. No. 6,316,262, U.S. Pat. No. 6,689,589, U.S. Pat. No. 7,081,357, U.S. Pat. No. 7,229,804, U.S. Pat. No. 6,759,219, and U.S. Pat. App. Pub. 2004/0253693, which are hereby incorporated by reference in their entirety. In an experiment similar to the one described in Example 1, sodium 5-hydroxyvalerate (Na5HV) was fed to strain MG1655 [pMS93] along with sodium 4-hydroxybutyrate (Na4HB). Strain MG1655 [pMS93] contains the genes orfZ and phaC, both of which are required to generate 4HB-CoA and 5HV-CoA from Na4HB and Na5HV, respectively, as well as to polymerize the precursors to the P(4HB-co-5HV) copolymer. Na4HB for use as substrate was prepared analogous to the method described for preparation of Na5HV in Example 1 with use of γ-butyrolactone (GBL) in place of DVL. The culture conditions used for copolymer production was also the same as that described in Example 1 with the difference that 4 g/L of Na4HB was added to the production medium. Following the PHA production period, analysis of polymer content of the MG1655 [pMS93] culture proceeded as described in Example 1 except that a standard curve for determining 4HB content was made using GBL standards in addition to the standard curve made for determining the 5HV content. This analysis showed that the MG1655 [pMS93] culture cofed Na4HB and Na5HV generated P(4HB-co-5HV) copolymer that comprised 67% dcw and had a composition that was 67% 4HB and 33% 5HV. An extracted sample of this polymer was analyzed using DSC and was determined to have a Tg of −54.9° C. and no detectable Tm.

Example 12

Biosynthesis of Glutarate from Glucose

In order to differentiate which of the two gene products were the primary GSA dehydrogenase as identified in Example 7, wild-type strain MG1655 [pJB91], MG1655ΔyneI::FRT [pJB91], and MG1655ΔgabD::FRT [pJB91] were compared for their ability to produce glutarate from 5-aminopentanoate, an intermediate metabolite between L-lysine and GSA (see FIG. 2). All three strains contain plasmid pJB91 which express davBAT from the $P_{ompA}$ promoter as described in Example 5. The three strains were grown in E0 minimum medium containing 2 g/L 5-aminopentanoate as described earlier and glutarate was measured by a GC-MS method from culture supernatants. The incubation method and conditions were the same as described in Example 7.

Unlike the other two strains, MG1655ΔgabD [pJB91] did not accumulate any detectable glutarate. Thus, the dehydrogenase encoded by gabD has the major activity towards GSA. Therefore, if high amounts of glutarate is to be produced, production hosts need to express gabD or homologues (see Table 1P) thereof. However, since MG1655ΔyneI [pJB91] accumulated slightly lower amounts of glutarate from 5-aminopentanoate as compared to MG1655 [pJB91], 0.75 g/L versus 1.0 g/L glutarate, respectively, the dehydrogenase encoded by yneI also has moderate activity towards GSA. Thus, overexpression of yneI or homologues (see Table 1Q) thereof, may also yield high amounts of glutarate from GSA, L-lysine or glucose.

The two best GabD homologues present in *Corynebacterium glutamicum* include (1) the NAD-dependent aldehyde dehydrogenase (Accession No. NP_599302) and (2) the hypothetical protein cgR_0068 (Accession No. YP_001136931). Unexpectedly, these two *C. glutamicum* proteins were also identified as the two closest homologues to *E. coli* YneI.

Next, glutarate was produced from glucose. To provide an L-lysine-overproducing strain, plasmid pDE033 which contains the L-lysine feed-back resistant dapA$^{C352T}$ gene was constructed as follows: the product of SOE-PCR for the fabrication of dapA$^{C352T}$ gene described in Example 9 was digested with EcoRI and SacI, followed by ligation with pSE380 that had been digested with the same enzymes, thus creating plasmid pDE033. The dapA$^{C352T}$ gene in pDE033 is under the IPTG-inducible promoter $P_{trc}$. Plasmids pDE033 and pJB91 (described above) were transformed into MG1655 strain to create strain MG1655 [pDE033, pJB91]. The strains MG1655 and MG1655 [pDE033, pJB91] were incubated for 48 h with shaking at 300 rpm at 30° C. in a medium that contained 25 g/L glucose, 16 g/L $(NH_4)_2SO_3$, 1 g, $KH_2PO_4$, 1 g/L $MgSO_4$, 2 g/L yeast extract, 30 g/L $CaCO_3$, 0.1 mM IPTG, and trace elements as described above. The culture media for MG1655 [pDE033, pJB91] was supplemented with 100 μg/mL ampicillin and 25 μg/mL chloramphenicol. Glutarate was measured as described in Example 7. The data shown in Table 13 demonstrates that MG1655 [pDE033, pJB91] secreted 0.7 g/L glutarate into the medium while the negative control strain MG1655 did not produce any glutarate. This result clearly shows that using a feedback-resistant dapA gene to accumulate L-lysine, together with the davBAT operon to convert L-lysine to GSA in a host cell that encodes a GSA dehydrogenase, is sufficient to produce glutarate from glucose as the sole carbon source.

TABLE 13

Glutarate production from glucose

| Strain [Plasmid] | Relevant Plasmid Genotype | Glutarate (g/L) |
|---|---|---|
| MG1655 | | 0 |
| MG1655 [pDE033, pJB91] | pDE33: $P_{Trc}$-dapA$^{C352T}$ pJB91: $P_{ompA}$-davBAT | 0.7 |

Example 13

Biosynthesis of 1,5-Pentanediol from Sodium 5-hydroxyvalerate

Strain Construction

Strain MBX3017 (LS5218 ΔadhE::FRT, ΔldhA::FRT, ΔackA-pta::FRT) and K-12 strain MG1655 were used as a host strain to assess if 1,5-pentanediol (PDO) could be accumulated and secreted into the medium. Each single deletion strain was constructed by the Red/ET method from Gene Bridges. Primers for constructing knock-out cassettes for the three pathways are listed in Table 14. Briefly, the following primers were used for the construction of the various chromosomal deletions: MS286 and MS287 for the ΔadhE cassette; MS289 and MS290 for the ΔackA-pla cassette; and MS292 and MS293 for the ΔldhA cassette. The LS5218 ΔadhE::FRT, ΔldhA::FRT, ΔackA-pta::FRT was obtained by iteratively P1 transducing each single null mutation into LS5218 and removing the marker as described in an earlier example.

TABLE 14

Primer used for PDO studies

| Primer | Sequence (5' → 3') | Comment |
|---|---|---|
| MS286 | CGGTTTATGTTGCCAGACAGCGCTACTGATTAAGCGGATTTT TTCGCTTTCATATGAATATCCTCCTTAGT (SEQ ID NO: 44) | ΔadhE cassette |
| MS287 | CGAGCAGATGATTTACTAAAAAAGTTTAACATTATCAGGAG AGCATTATGGTGTAGGCTGGAGCTGCTTC (SEQ ID NO: 45) | ΔadhE cassette |
| MS289 | TGGCTCCCTGACGTTTTTTTAGCCACGTATCAATTATAGGTA CTTCCATGGTGTAGGCTGGAGCTGCTTC (SEQ ID NO: 46) | ΔackA-pta cassette |
| MS290 | GCAGCGCAAAGCTGCGGATGATGACGAGATTACTGCTCCTG TGCAGACTGCATATGAATATCCTCCTTAGT (SEQ ID NO: 47) | ΔackA-pta cassette |
| MS292 | CTCCCCTGGAATGCAGGGGAGCGGCAAGATTAAACCAGTTC GTTCGGGCACATATGAATATCCTCCTTAGT (SEQ ID NO: 48) | ΔldhA cassette |
| MS293 | TATTTTTAGTAGCTTAAATGTGATTCAACATCACTGGAGAA AGTCTTATGGTGTAGGCTGGAGCTGCTTC (SEQ ID NO: 49) | ΔldhA cassette |
| FS011 | TCCCCTAGGATTCAGGAGGTTTTTATGGAGTGGGAAGAGAT ATATAAAG (SEQ ID NO: 50) | 5' of orfZ |
| FS008 | CCTTAAGTCGACAAATTCTAAAATCTCTTTTTAAATTC (SEQ ID NO: 51) | 3' of orfZ |
| JRG047 | TTCAGGATCCTGCGCATGCTAGCTATAGTTCTAGAGGTA (SEQ ID NO: 52) | 5' of pduP |
| JRG048 | CATACGATAGCTCATAAAAACCTCCTCGCAGTTAGCGAATA GAAAAGCCGTTGG (SEQ ID NO: 53) | 3' of pduP |
| JRG049 | GAGGAGGTTTTTATGAGCTATCGTATGAGCTATCGTATGTTT GATTATCTGGTGC (SEQ ID NO: 54) | 5' of dhaT |
| JRG050 | TCTTTCATGAACTCAGAATGCCTGGCGGAAAATCG (SEQ ID NO: 55) | 3' of dhaT |

The CoA-dependent propionaldehyde dehydrogenase encoding pduP from *S. typhimurium* (see Table 1A; Leal, Arch. Microbiol. 180:353-361 (2003)) was amplified by primers JRG47 and JRG4S. The 1,3-propanediol dehydrogenase encoding dhaT from *Klebsiella pneumoniae* (see Table 1A; Tong et al., Appl. Environ. Microbiol. 57(12):3541-3546 (1991)) was amplified with primers JRG49 and JRG50. The two genes were fused together by SOE-PCR using primers JRG47 and JRG50. The resulting DNA fragment was cloned into pJB78 via BamHI and BspHI sites, and the resulting plasmid was designated as pJG10.

Strain MBX3017 or MG1655 harboring pFS16 or pSE380 and pJG10 or pJB78 were used for PDO studies.

Strains were grown under oxygen limited conditions in 5HV-containing E2 medium for 40 h. The medium consisted of: 10 g/L glucose, 2 g/L 5HV, 26 mM $NaNH_4HPO_4$, 33 mM $K2HPO_4$, 27 mM $KH_2PO_4$, 2 mM $MgSO_4$, 25 µg/mL chloramphenicol, 100 µg/mL ampicillin, 0.1 mM IPTG, and trace elements as described above. Overnight cultures were inoculated into a sealed culture tube containing fresh medium to a final $OD_{600}$ of approximately 0.2, the headspace for the culture tube was small to ensure oxygen limitation of the culture. The cultures were incubated at 30° C. After 48 h of incubation, 100 µl, sample was removed, centrifuged, and the resulting supernatant was spiked with 1,4-butanediol (0.1 µ/L) as internal standard, dried in a Labconco centrivap and resuspended in 100 µL acetonitrile (ACN) by sonication for 3 h. The acetonitrile solution was centrifuged to remove insoluble material, and the supernatant was injected into an Agilent 5975 GC-MS equipped with a DB-225 ms column using the following acquisition parameters: carrier gas Helium flow rate 1 ml/min, scan mode m/z 30-400, oven program: 40° C. for 2 min, then ramp up to 220° C. at 10° C./min, ion source temperature 230° C., the quadrupole mass filter temperature 150° C.

Figure 8A:
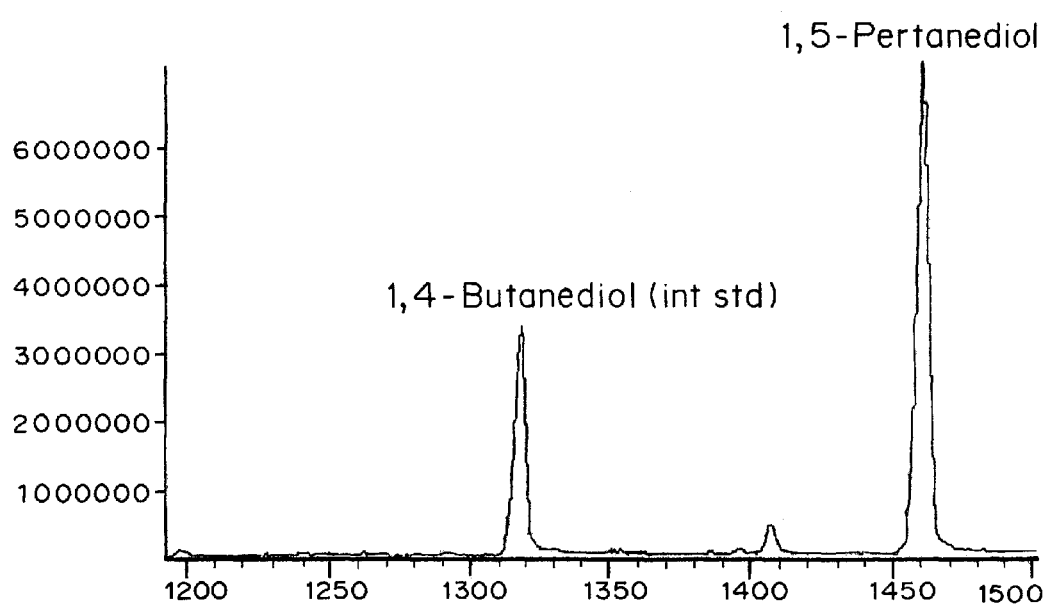
FIG. 8A is chromatogram showing time (minutes) versus total ion abundance of processed cell culture from strain 3291.
Figure 8B:
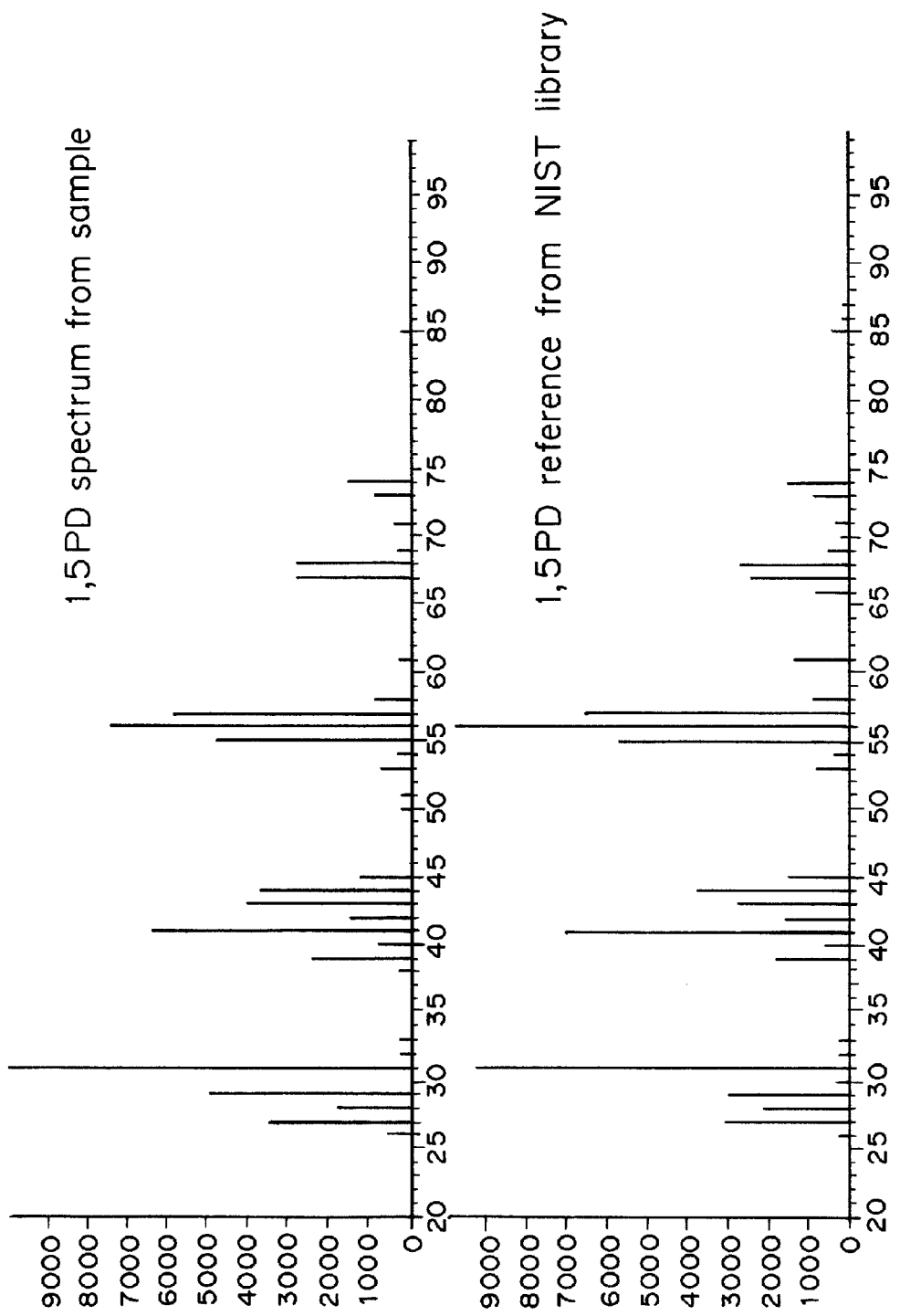
FIG. 8B is an ion spectrum of processed cell culture from strain 3291 showing mass-to-charge ratio "m/z" versus its ion abundance (relative units).

The measured PDO results are shown in Table 14. The combination of host strain MBX3017 and overexpression of orfZ-dhaT-pduP gave the highest PDO yield of 0.32 g/L. Strain MG1655 harboring these three genes gave a lower yield of 0.22 g/L, possibly due to its active ethanol, acetate and lactate pathway, which are known electron acceptors (Clark, FEMS Microbiol. Rev. 5:223-34 (1989)) and could compete with the 5HV pathway for NAD(P)H. Interestingly, MG1655 harboring just orfZ also produced small amounts of PDO, while the MBX3017 host did not yield any detectable PDO (Table 15). This indicates that a endogenous alcohol dehydrogenase, e.g. adhE, has weak activity towards 5HV-CoA. The measured PDO was confirmed by GC-MS against the PDO standard and NIST library PDO reference spectrum as shown in FIG. 8. These results demonstrate that PDO can be produced from Na5HV when the orfZ gene is expressed to generate 5HV-CoA and the pduP-dhaT genes are expressed converting 5HV-CoA to 5-hydroxypentenal and to PDO.

TABLE 15

PDO titer of strains grown in 5HV containing medium[a]

| Plasmids and Genes Expressed | PDO (g/L) MG1655 | PDO (g/L) MBX3017 |
|---|---|---|
| pFS16: $P_{trc}$-orfZ pJB78: empty vector | 0.08 | 0 |
| pJG10: $P_{tet}$-pduP-dhaT pSE380: empty vector | 0 | 0 |
| pFS16: $P_{trc}$-orfZ pJG10: $P_{tet}$-pduP-dhaT | 0.22 | 0.32 |
| pJB78: empty vector pSE380: empty vector | 0 | 0 |

[a]Results are the average of three independent replicated experiments

Gene ID 001 Nucleotide Sequence: *Aspergillus terreus* NIH2624 glutarate semialdehyde reductase gene $gsaR_{At2}$

```
(SEQ ID NO: 56)
ATGCCACTGGTTGCTCAAAATCCACTCCCACGTGCTATTCTGGGTCTGAT

GACTTTCGGTCCGAGCGAAAGCAAAGGTGCGCGTATCACTTCCCTGGATG

AGTTTAACAAGTGCCTGGATTACTTCCAGCAGCAGGGCTTCCAGGAAATC

GATACCGCGCGCATCTACGTCGGCGGTGAACAGGAGGCATTCACGGCGCA

GGCAAAGTGGAAAGAACGCGGCCTGACGCTGGCGACTAAGTGGTATCCGC

AGTACCCGGGTGCGCACAAACCGGATGTCCTGCGTCAGAACCTGGAGCTG

TCCCTGAAAGAACTGGGCACGAACCAGGTCGATATCTTCTATCTGCACGC

CGCGGATCGTTCTGTGCCGTTCGCGGAAACTCTGGAAACTGTTAACGAAC

TGCACAAAGAAGGCAAATTTGTTCAGCTGGGTCTGTCTAACTACACCGCT

TTCCAAGTAGCTGAAATCGTGACCCTGTGTAACGAGCGTGGTTGGGTTCG

TCCGACTATCTACCAGGCGATGTATAACGCTATCACCCGTAACATCGAAA

CTGAACTGATCCCGGCGTGCAAGCGTTACGGTATTGACATTGTTATCTAC

AACCCACTGGCGGGTGGCCTGTTCAGCGGCAAATACAAAGCACAGGACAT

CCCGGCTGAAGGTCGTTACAGCGACCAATCTTCCATGGGCCAGATGTACC

GCAACCGTTACTTTAAGGACGCAACCTTTGACGCTCTGCGCCTGATCGAA

CCGGTTGTTGCGAAGCACGGCCTGACGATGCCGGAAACCGCGTTCCGCTG

GGTCCACCACCACTCCGCACTGAACATGGAAGATGGCGGCCGTGACGGCA

TCATTCTGGGTGTAAGCAGCCTGGCTCAGCTGGAAAACAACCTGAAAGAC

ATTCAGAAAGGTCCGCTGCCGCAGGAGGTTGTAGACGTCCTGGATCAGGC

TTGGCTGGTGGCTAAGCCGACGGCTCCAAACTACTGGCATCTGGACCTGA

AATACACGTACGACACCCAGGAAGCTCTGTTCAAACCGAAATCTAAGGCG

TAA
```

Gene ID 001 Amino Acid Sequence: *Aspergillus terreus* NIH2624 glutarate semialdehyde reductase gene $gsaR_{At2}$

```
(SEQ ID NO: 57)
MPLVAQNPLPRAILGLMTFGPSESKGARITSLDEFNKCLDYFQQQGFQEI

DTARIYVGGEQEAFTAQAKWKERGLTLATKWYPQYPGAHKPDVLRQNLEL

SLKELGTNQVDIFYLHAADRSVPFAETLETVNELHKEGKFVQLGLSNYTA

FEVAEIVTLCNERGWVRPTIYQAMYNAITRNIETELIPACKRYGIDIVIY

NPLAGGLFSGKYKAQDIPAEGRYSDQSSMGQMYRNRYFKDATFDALRLIE

PVVAKHGLTMPETAFRWVHHHSALNMEDGGRDGIILGVSSLAQLENNLKD

IQKGPLPQEVVDVLDQAWLVAKPTAPNYWHLDLKYTYDTQEALFKPKSKA
```

Gene ID 002 Nucleotide Sequence: *Arabidopsis thaliana* glutarate semialdehyde reductase gene gsaR$_{At}$ (SEQ ID NO: 58)
ATGGAAGTAGGTTTTCTGGGTCTGGGCATTATGGGTAAAGCTATGTCCAT
GAACCTGCTGAAAAACGGTTTCAAAGTTACCGTGTGGAACCGCACTCTGT
CTAAATGTGATGAACTGGTTGAACACGGTGCAAGCGTGTGCGAGTCTCCG
GCTGAGGTGATCAAGAAATGCAAATACACGATCGCGATGCTGAGCGATCC
GTGTGCAGCTCTGTCTGTTGTTTTCGATAAAGGCGGTGTTCTGGAACAGA
TCTGCGAGGGTAAGGGCTACATCGACATGTCTACCGTCGACGCGAAACT
AGCCTGAAAATTAACGAAGCGATCACGGGCAAAGGTGGCCGTTTTGTAGA
AGGTCCTGTTAGCGGTTCCAAAAAGCCGGCAGAAGACGGCCAGCTGATCA
TCCTGGCAGCAGGCGACAAAGCACTGTTCGAGGAATCCATCCCGGCCTTT
GATGTACTGGGCAAACGTTCCTTTTATCTGGGTCAGGTGGGTAACGGTGC
GAAAATGAAACTGATTGTTAACATGATCATGGGTTCTATGATGAACGCGT
TTAGCGAAGGTCTGGTACTGGCAGATAAAAGCGGTCTGTCTAGCGACACG
CTGCTGGATATTCTGGATCTGGGTGCTATGACGAATCCGATGTTCAAAGG
CAAAGGTCCGTCCATGACTAAATCCAGCTACCCACCGGCTTTCCCGCTGA
AACACCAGCAGAAGACATGCGTCTGGCTCTGGCTCTGGGCGACGAAAAC
GCTGTTAGCATGCCGGTCGCTGCGGCTGCGAACGAAGCCTTCAAGAAAGC
CCGTAGCCTGGGCCTGGGCGATCTGGACTTTTCTGCTGTTATCGAAGCGG
TAAAATTCTCTCGTGAATAA Gene ID 002 Amino Acid Sequence: *Arabidopsis thaliana* glutarate semialdehyde reductase gene gsaR$_{At}$ (SEQ ID NO: 59)
MEVGFLGLGIMGKAMSMNLLKNGFKVTVWNRTLSKCDELVEHGASVCESP
AEVIKKCKYTIAMLSDPCAALSVVFDKGGVLEQICEGKGYIDMSTVDAET
SLKINEAITGKGGRFVEGPVSGSKKPAEDGQLIILAAGDKALFEESIPAF
DVLGKRSFYLGQVGNGAKMKLIVNMIMGSMMNAFSEGLVLADKSGLSSDT
LLDILDLGAMTNPMFKGKGPSMTKSSYPPAFPLKHQQKDMRLALALGDEN
AVSMPVAAAANEAFKKARSLGLGDLDFSAVIEAVKFSRE Gene ID 003 Nucleotide Sequence: *Pseudomonas putida/Zoogloea ramigera* polyhydroxyalkanoate synthase fusion gene phaC3/C5

(SEQ ID NO: 60)
ATGAGTAACAAGAACAACGATGAGCTGCAGTGGCAATCCTGGTTCAGCAA
GGCGCCCACCACCGAGGCGAACCCGATGGCCACCATGTTGCAGGATATCG
GCGTTGCGCTCAAACCGGAAGCGATGGAGCAGCTGAAAAACGATTATCTG
CGTGACTTCACCGCGTTGTGGCAGGATTTTTTGGCTGGCAAGGCGCCAGC
CGTCAGCGACCGCCGCTTCAGCTCGGCAGCCTGGCAGGGCAATCCGATGT
CGGCCTTCAATGCCGCATCTTACCTGCTCAACGCCAAATTCCTCAGTGCC
ATGGTGGAGGCGGTGGACACCGCACCCCAGCAAAAGCAGAAAATACGCTT
TGCCGTGCAGCAGGTGATTGATGCCATGTCGCCCGCGAACTTCCTCGCCA
CCAACCCGGAAGCGCAGCAAAAACTGATTGAAACCAAGGGCGAGAGCCTG
ACGCGTGGCCTGGTCAATATGCTGGGCGATATCAACAAGGGCCATATCTC
GCTGTCGGACGAATCGGCCTTTGAAGTGGGCCGCAACCTGGCCATTACCC
CGGGGCACCGTGATTTACGAAAATCCGCTGTTCCAGCTGATCCAGTACACG
CCGACCACGCCGACGGTCAGCCAGCGCCCGCTGTTGATGGTGCCGCCGTG
CATCAACAAGTTCTACATCCTCGACCTGCAACCGGAAAATTCGCTGGTGC
GCTACGCGGTGGAGCAGGGCAACACCGTGTTCCTGATCTCGTGGAGCAAT
CCGGACAAGTCGCTGGCCGGCACCACCTGGGACGACTACGTGGAGCAGGG
CGTGATCGAAGCGATCCGCATCGTCGAGGACGTCAGCGGCCAGGACAAGC
TGAACATGTTCGGCTTCTGCGTGGGCGGCACCATCGTTGCCACCGCACTG
GCGGTACTGGCGGCGTGGCCAGCACCCGGCGGCCAGCCTGACCCTGCT
GACCACCTTCCTCGACTTCAGCGACACCGGCGTGCTCGACGTCTTCGTCG
ATGAAACCCAGGTCGCGCTGCGTGAACAGCAATTGCGCGATGGCGGCCTG
ATGCCGGGCCGTGACCTGGCCTCGACCTTCTCGAGCCTGCGTCCGAACGA
CCTGGTATGGAACTATGTGCAGTCGAACTACCTCAAAGGCAATGAGCCGG
CGGCGTTTGACCTGCTGTTCTGGAATTCGGACAGCACCAATTTGCCGGGC
CCGATGTTCTGCTGGTACCTGCGCAACACCTACCTGGAAAACAGCCTGAA
AGTGCCGGGCAAGCTGACGGTGGCCGGCGAAAAGATCGACCTCGGCCTGA
TCGACGCCCCGGCCTTCATCTACGGTTCGCGCGAAGACCACATCGTGCCG
TGGATGTCGGCGTACGGTTCGCTCGACATCCTCAACCAGGGCAAGCCGGG
CGCCAACCGCTTCGTGCTGGGCGCGTCCGGCCATATCGCCGGCGTGATCA
ACTCGGTGGCCAAGAACAAGCGCAGCTACTGGATCAACGACGGTGGCGCC
GCCGATGCCCAGGCCTGGTTCGATGGCGCGCAGGAAGTGCCGGGCAGCTG
GTGGCCGCAATGGGCCGGGTTCCTGACCCAGCATGGCGGCAAGAAGGTCA
AGCCCAAGGCCAAGCCCGGCAACGCCCGCTACACCGCGATCGAGGCGGCG
CCCGGCCGTTACGTCAAAGCCAAGGGCTGA

Gene ID 003 Amino Acid Sequence: *Pseudomonas putida/Zoogloea ramigera* polyhydroxyalkanoate synthase fusion gene PhaC3/C5

(SEQ ID NO: 61)
MSNKNNDELQWQSWFSKAPTTEANPMATMLQDIGVALKPEAMEQLKNDYL
RDFTALWQDFLAGKAPAVSDRRFSSAAWQGNPMSAFNAASYLLNAKFLSA
MVEAVDTAPQQKQKIRFAVQQVIDAMSPANFLATNPEAQQKLIETKGESL
TRGLVNMLGDINKGHISLSDESAFEVGRNLAITPGTVIYENPLFQLIQYT
PTTPTVSQRPLLMVPPCINKFYILDLQPENSLVRYAVEQGNTVFLISWSN
PDKSLAGTTWDDYVEQGVIEAIRIVQDVSGQDKLNMFGFCVGGTIVATAL
AVLAARGQHPAASLTLLTTFLDFSDTGVLDVFVDETQVALREQQLRDGGL
MPGRDLASTFSSLRPNDLVWNYVQSNYLKGNEPAAFDLLFWNSDSTNLPG
PMFCWYLRNTYLENSLKVPGKLTVAGEKIDLGLIDAPAFIYGSREDHIVP

```
-continued
WMSAYGSLDILNQGKPGANRFVLGASGHIAGVINSVAKNKRSYWINDGGA

ADAQAWFDGAQEVPGSWWPQWAGFLTQHGGKKVKPKAKPGNARYTAIEAA

PGPYVKAKG
```

Gene ID 004 Nucleotide Sequence: *Thiocapsa phenigii* polyhydroxyalkanoate synthase subunit phaE

```
                                      (SEQ ID NO: 62)
ATGGCTGGTGACCACGTCGTGGAATGCCTTCGAATTCAGGAGGTTTTTAT

GAACGATACGGCCAACAAGACCAGCGACTGGCTGGACATCCAAGGCAAGT

ACTGGGAGACCTGGTCGGAGCTCGGCCGCAAGACCTTGGGTCTGGAGAAG

AGCCCGGCCAATCCTTGGGCCGGCGCCCTCGATCATTGGTGGCAGACGGT

CTCGCCCGCCGCCCCAACGACCTGGTTCGCGACTTCATGGAGAAGCTCG

CCGAGCAGGGCAAGGCCTTCTTCGGCCTCACCGACTACTTCACGAAGGGC

CTCGGCGGCAGTAGCGGTACGCAGGGCTGGGACACCCTCTCGAAGACCAT

CGACGACATGCAAAAGGCCTTCGCCAGCGGCCGGATCGAAGGCGACGAGA

CCTTCCGCCGCCTGATGGCCTTCTGGGAGATGCCGCTCGACAACTGGCAC

GGCACCATGTCCTCGCTGTCCCCGGTGCCCGGCGACCTGCTGCGCAACAT

GCCGCACGACCAAGTCAGGGACAGCGTCGACCGCATCCTCTCGGCACCCG

GGCTCGGCTACACGCGCGAGGAGCAGGCCCGCTACCAGGATCTGATCCGC

CGCTCGCTGGAGTACCAGTCGGCCCTGAACGAATACAACGGCTTCTTCGG

CCAGCTCGGTGTCAAGTCCCTCGAGCGGATGCGCGCCTTCCTGCAGGGAC

AGGCCGAGAAGGGCGTCGCCATCGAGTCGGCGCGCACCCTCTACGACGCC

TGGGTCGGCTGCTGCGAAGAGGTCTATGCCGAGGAGGTCAGCTCCGCCGA

CTACGCGCACATCCACGGCCGCCTCGTCAACGCCCAGATGGCCCTCAAGC

AGCGCATGTCGACCATGGTCGACGAGGTCCTCGGCGCGATGCCGCTGCCG

ACCCGCAGCGAGCTGCGCACGCTCCAGGATCGGCTCCAGGAGTCGCGCGG

CGAGGGCAAGCGCCAGCGCCAAGAGATCGAGACGCTGAAGCGGCAGGTCG

CGGCCTTGGCCGGCGGCGCCCAGCCCGCGCCCCAGGCCTCCGCCCAGCCC

AGCACCCGGCCCGCGCCGGCGACGGCCCCGGCGGCGAGCGCGGCGCCCAA

GCGCAGCACCACGACCCGCCGCAAGACCACCAAGCCCACCACCGGCCAGT

GA
```

Gene ID 004 Amino Acid Sequence: *Thiocapsa phenigii* polyhydroxyalkanoate synthase subunit PhaE

```
                                      (SEQ ID NO: 63)
MNDTANKTSDWLDIQRKYWETWSELGRKTLGLEKTPANPWAGALDHWWQT

VSPAAPNDLVRDFMEKLAEQGKAFFGLTDYFTKGLGGSSGTQGWDTLSKT

IDDMQKAFASGRIEGDETFRRLMAFWEMPLDNWQRTMSSLSPVPGDLLRN

MPHDQVRDSVDRILSAPGLGYTREEQARYQDLIRRSLEYQSALNEYNGFF

GQLGVKSLERMRAFLQGQAEKGVAIESARTLYDAWVGCCEEVYAEEVSSA

DYAHIHGRLVNAQMALKQRMSTMVDEVLGAMPLPTRSELRTLQDRLQESR

GEGKRQRQEIETLKRQVAALAGGAQPAPQASAQPSTRPAPATAPAASAAP

KRSTTTRRKTTKPTTGQ
```

Gene ID 005 Nucleotide Sequence: *Thiocapsa phenigii* polyhydroxyalkanoate synthase subunit phaC

```
                                      (SEQ ID NO: 64)
ATGTCCCCATTCCCGATCCACATCCGGCCCGACAAGCTGACCGAGGAGAT

GCTGGAGTACAGCCGCAAGCTCGGCGAGGGTATGCAGAACCTGCTCAAGG

CCGACCAGATCGACACAGGCGTCACCCCCAAGGACGTCGTCCACCGCGAG

GACAAGCTGGTCCTCTACCGCTACCGGCGCCCGGCGCAGGTGGCGACCCA

GACGATCCCGCTGCTGATCGTCTACGCCCTCGTCAATCGGCCCTACATGA

CCGACATCCAGGAGGATCGCTCGACGATCAAGGGCCTGCTCGCCACCGGT

CAGGACGTCTATCTGATCGACTGGGGCTACCCGGATCAGGCCGACCGGGC

GCTGACCCTCGATGACTACATCAACGGCTACATCGACCGCTGCGTCGACT

ACCTGCGCGAGACCCACGGCGTCGACCAGGTCAACCTGCTCGGGATCTGC

CAGGGCGGGGCCTTCAGCCTCTGCTACACGGCCCTGCACTCCGAGAAGGT

CAAAAACCTCGTCACCATGGTCACGCCGGTCGACTTCCAGACCCCGGGCA

ACCTGCTCTCGGCCTGGGTCCAGAACGTCGACGTCGACCTGGCCGTCGAC

ACCATGGGCAACATCCCGGGCGAACTGCTCAACTGGACCTTCCTGTCGCT

CAAGCCCTTCAGCCTGACCGGCCAGAAGTACGTCAACATGGTCGACCTGC

TCGACGACGAGGACAAGGTCAAGAACTTCCTGCGGATGGAGAAGTGGATC

TTCGACAGCCCGGACCAGGCCGGCGAGACCTTCCGCCAGTTCATCAAGGA

CTTCTACCAGCGCAACGGCTTCATCAACGGCGGCGTCCTGATCGGCGATC

AGGAGGTCGACCTGCGCAACATCCGCTGCCCGGTCCTGAACATCTACCCG

ATGCAGGACCACCTGGTGCCGCCGGATGCCTCCAAGGCCCTCGCGGGACT

GACCTCCAGCGAGGACTACACGGAGCTCGCCTTCCCCGGCGGGCACATCG

GCATCTACGTCAGCGGCAAGGCGCAGGAAGGAGTCACCCCGGCGATCGGC

CGCTGGCTGAACGAACGCGGCTGA
```

Gene ID 005 Amino Acid Sequence: *Thiocapsa phenigii* polyhydroxyalkanoate synthase subunit PhaC

```
                                      (SEQ ID NO: 65)
MSPFPIDIRPDKLTEEMLEYSRKLGEGMQNLLKADQIDTGVTPKDVVHRE

DKLVLYRYRRPAQVATQTIPLLIVYALVNRPYMTDIQEDRSTIKGLLATG

QDVYLIDWGYPDQADRALTLDDYINGYIDRCVDYLRETHGVDQVNLLGIC

QGGAFSLCYTALHSEKVKNLVTMVTPVDFQTPGNLLSAWVQNVDVDLAVD

TMGNIPGELLNWTFLSLKPFSLTGQKYVNMVDLLDDEDKVKNFLRMEKWI

FDSPDQAGETFRQFIKDFYQRNGFINGGVLIGDQEVDLRNIRCPVLNIYP

MQDHLVPPDASKALAGLTSSEDYTELAFPGGHIGIYVSGKAQEGVTPAIG

RWLNERG
```

We claim:

1. A recombinant organism genetically engineered to convert glutarate semialdehyde into a 5-hydroxyvalerate monomer, polymer or copolymer thereof,
    wherein the recombinant organism expresses at least two or more heterologous genes encoding two or more enzymes selected from the group consisting of: lysine 2-monooxygenase, EC 1.13.12.2; 5-aminopentanamidase (δ-aminovaleramidase), EC 3.5.1.30; 5-aminovalerate transaminase, EC 2.6.1.48; lysine decarboxylase, EC 4.1.1.18; glutarate semialdehyde reductase, EC 1.1.1.61; 4-hydroxybutyrate dehydrogenase, EC 1.1.1.61; CoA-transferase, EC 2.8.3.14 and EC 2.8.3.n; Acyl-CoA synthetase, EC 6.2.1.3; PHA synthase, EC 2.3.1.n; β-ketoacyl-CoA thiolase, EC 2.3.1.9; acetoacetyl-CoA reductase, EC 1.1.1.36; propionaldehyde dehydrogenase, EC 1.2.1.3; alcohol dehydrogenase, EC 1.1.1.1; and 1,3-propanediol dehydrogenase EC 1.1.1.202;
    wherein the recombinant organism produces more 5-aminopentanoate than an unmodified organism; and
    wherein the 5-aminopentanoate is converted into the 5-hydroxyvalerate monomer, polymer or copolymer thereof by the recombinant organism wherein the 5-hydroxyvalerate monomer, polymer or copolymer thereof is isolatable.

2. The recombinant organism of claim 1 wherein the organism produces 1,5 pentanediol.

3. The recombinant organism of claim 1 wherein the polymer or copolymer comprises polyhydroxyalkanoate.

4. The recombinant organism of claim 1 wherein the recombinant organism converts 5-aminopentanoate into glutarate semialdehyde.

5. The recombinant organism of claim 1 wherein the recombinant organism converts lysine into 5-aminopentanoate.

6. The recombinant organism of claim 5 wherein the lysine is fed to the organism.

7. The recombinant organism of claim 1 wherein the organism used to construct the recombinant organism has been modified to overproduce lysine relative to an unmodified organism.

8. The recombinant organism of claim 1 wherein the recombinant organism is resistant to the toxic lysine analog S-(2-aminoethyl) cysteine.

9. The recombinant organism of claim 1 wherein the recombinant organism expresses a lysine feedback-resistant dihydrodipicolinate synthase.

10. The recombinant organism of claim 1 wherein the recombinant organism expresses a lysine feedback-resistant aspartate kinase III.

11. The recombinant organism of claim 1 wherein the organism is fed a renewable carbon substrate.

12. The recombinant organism of claim 1 wherein the recombinant organism is further engineered to inhibit or block lysine export.

13. The recombinant organism of claim 1 wherein the organism has been modified to reduce or eliminate glutarate semialdehyde dehydrogenase activity.

14. The recombinant organism of claim 13 wherein the glutarate semialdehyde dehydrogenase is reduced or eliminated by deleting or disrupting one or more genes selected from the group consisting of davD, yneI, and gabD or their homologs.

15. The recombinant organism of claim 1 wherein the recombinant organism releases 5-hydroxyvalerate into the extracellular environment.

16. The recombinant organism of claim 13 wherein the recombinant organism releases 5-hydroxyvalerate in the extracellular environment and the 5-hydroxyvalerate is in equilibrium with delta-valerolactone.

17. The recombinant organism of any of claim 1 wherein the recombinant organism converts 5-hydroxyvalerate into 5-hydroxyvalerate CoA.

18. The recombinant organism of claim 1 wherein the recombinant organism converts 5-hydroxyvalerate-CoA into a polyhydroxyalkanoate.

19. The recombinant organism of claim 1 wherein the recombinant organism converts 5-hydroxvalerate into 1,5 pentanediol.

20. The recombinant organism of claim 1 wherein the recombinant organism converts 5-hydroxyvalerate into poly (5-hydroxyvalerate) or a copolymer thereof.

21. The recombinant organism of claim 20 wherein the copolymer is selected from the group consisting of poly(3-hydroxypropionate-co-5HV), poly(3-hydroxybutyrate-co-5HV) and poly(4-hydroxybutyrate-co-5HV).

22. The recombinant organism of claim 1 wherein the recombinant organism is prokaryotic.

23. The recombinant organism of claim 1 wherein the recombinant organism is *E. coli*.

24. The recombinant organism of claim 1 wherein the recombinant organism is a eukaryotic microorganism.

25. A recombinant organism for producing polymers from lysine
    wherein the recombinant organism is genetically engineered to express at least two heterologous enzymes selected from the group consisting of: lysine 2-monooxygenase, EC 1.13.12.2; 5-aminopentanamidase (δ-aminovaleramidase), EC 3.5.1.30; 5-aminovalerate transaminase, EC 2.6.1.48; lysine decarboxylase, EC 4.1.1.18; glutarate semialdehyde reductase, EC 1.1.1.61; 4-hydroxybutyrate dehydrogenase, EC 1.1.1.61; CoA-transferase, EC 2.8.3.14 and EC 2.8.3.n; Acyl-CoA synthetase, EC 6.2.1.3; PHA synthase, EC 2.3.1.n, to produce a polyhydroxyalkanoate comprising 5-hydroxyvalerate monomers,
wherein the recombinant organism produces more 5-aminopentanoate than an unmodified organism, and
wherein the recombinant organism can convert 5-aminopentanoate into the 5-hydroxyvalerate wherein the 5-hydroxyvalerate monomer, polymer or copolymer thereof is isolatable.

26. The recombinant organism of claim 25 wherein the recombinant organism does not produce lysine.

27. The recombinant organism of claim 25 wherein the recombinant organism does not express a functional glutarate semialdehyde dehydrogenase enzyme activity.

28. A method for producing polymers from lysine comprising feeding the recombinant organism of claim 1 with lysine and other renewable carbon feedstock such that the polymer is produced.

29. A method for producing 5-carbon based monomers, polymers or co-polymers thereof comprising
providing lysine or other renewable carbon feedstock to genetically engineered cells according to claim 1,
wherein the genetically engineered cells are engineered to produce more 5-aminopentanoate than unmodified cells, and wherein the 5-aminopentanoate is converted by the genetically engineered cells into a 5 carbon monomer, polymer or copolymer thereof.

30. The method of claim 29 wherein the renewable carbon feedstock is selected from starch, sucrose, glucose, lactose, fructose, xylose, maltose and arabinose, or combinations thereof.

31. The method of claim 29 wherein the monomer is selected from the group consisting of glutarate, 1,5-pentanediol, and 5-hydroxyvalerate.

32. The method of claim 29 wherein the polymer comprises a polyhydroxyalkanoate.

33. The method of claim 32 wherein the polyhydroxyalkanoate comprises 5-hydroxyvalerate.

34. The method of claim 33 wherein the polyhydroxyalkanoate is selected from the group consisting of poly(5-hydroxyvalerate), poly(3-hydroxypropionate-co-5HV), poly(3-hydroxybutyrate-co-5HV) and poly(4-hydroxybutyrate-co-5HV).

35. The method of claim 32 further comprising recovering the polyhydroxyalkanoate polymer.

36. The method of claim 35 wherein polyhydroxyalkanote polymer or copolymers are recovered by solvent extraction or aqueous processing.

* * * * *